US011304804B2

(12) United States Patent
Hariton et al.

(10) Patent No.: US 11,304,804 B2
(45) Date of Patent: Apr. 19, 2022

(54) PROSTHETIC VALVE WITH CONNECTING STRUTS OF VARIABLE SIZE AND TISSUE ANCHORING LEGS OF VARIABLE SIZE THAT EXTEND FROM JUNCTIONS

(71) Applicant: CARDIOVALVE LTD., Or Yehuda (IL)

(72) Inventors: Ilia Hariton, Zichron Yaackov (IL); Meni Iamberger, Kfar Saba (IL); Aviram Baum, Tel Aviv (IL); Boaz Harari, Ganey Tikva (IL)

(73) Assignee: CARDIOVALVE, LTD., Or Yehuda (IL)

( * ) Notice: Subject to any disclaimer, the term of this patent is extended or adjusted under 35 U.S.C. 154(b) by 0 days.

(21) Appl. No.: 16/135,599

(22) Filed: Sep. 19, 2018

(65) Prior Publication Data

US 2019/0083244 A1  Mar. 21, 2019

Related U.S. Application Data

(60) Provisional application No. 62/560,384, filed on Sep. 19, 2017.

(51) Int. Cl.
*A61F 2/24* (2006.01)

(52) U.S. Cl.
CPC ............ *A61F 2/2427* (2013.01); *A61F 2/243* (2013.01); *A61F 2/2436* (2013.01);
(Continued)

(58) Field of Classification Search
CPC ........ A61F 2/2418; A61F 2/2463; A61F 2/24; A61F 2/2409; A61F 2/852
See application file for complete search history.

(56) References Cited

U.S. PATENT DOCUMENTS

| 3,874,388 A | 4/1975 | King et al. |
| 4,222,126 A | 9/1980 | Boretos et al. |

(Continued)

FOREIGN PATENT DOCUMENTS

| CA | 2822801 A1 | 8/2006 |
| CN | 103974674 A | 8/2014 |

(Continued)

OTHER PUBLICATIONS

International Search Report dated Dec. 5, 2011, by the United States Patent and Trademark Office in PCT/IL2011/000582 (3 pages).

(Continued)

*Primary Examiner* — Yashita Sharma
*Assistant Examiner* — Amanda M Barkan
(74) *Attorney, Agent, or Firm* — Finnegan, Henderson, Farabow, Garrett & Dunner, LLP

(57) ABSTRACT

An expandable prosthetic valve for implantation within a native mitral valve may be provided. The prosthetic valve may include an expandable valve body having an atrial end, a ventricular end opposite the atrial end, and an intermediate portion extending between the atrial end and the ventricular end. The valve body may include a plurality of struts intersecting at junctions. The prosthetic valve may also include a plurality of tissue anchoring legs extending from junctions within the intermediate portion of the valve body. At least one of the tissue anchoring legs may have a cross-sectional area which is larger by at least 20% than a cross-sectional area of a strut extending between the at least one tissue anchoring leg and an adjacent tissue anchoring leg.

27 Claims, 21 Drawing Sheets

(52) U.S. Cl.
CPC .......... *A61F 2/2445* (2013.01); *A61F 2/2454* (2013.01); *A61F 2/2463* (2013.01); *A61F 2/246* (2013.01); *A61F 2/2409* (2013.01); *A61F 2/2418* (2013.01); *A61F 2/2466* (2013.01); *A61F 2210/0014* (2013.01); *A61F 2220/0008* (2013.01); *A61F 2250/007* (2013.01)

(56) References Cited

U.S. PATENT DOCUMENTS

| | | |
|---|---|---|
| 4,340,091 A | 7/1982 | Skelton et al. |
| 4,972,494 A | 11/1990 | White et al. |
| 5,201,757 A | 4/1993 | Heyn et al. |
| 5,713,948 A | 2/1998 | Uflacker |
| 5,716,417 A | 2/1998 | Girard et al. |
| 5,741,297 A | 4/1998 | Simon |
| 5,776,140 A | 7/1998 | Cottone |
| 5,957,949 A | 9/1999 | Leonhardt et al. |
| 5,961,549 A | 10/1999 | Nguyen et al. |
| 6,010,530 A | 1/2000 | Goicoechea |
| 6,126,686 A | 10/2000 | Badylak et al. |
| 6,165,183 A | 12/2000 | Kuehn et al. |
| 6,254,609 B1 | 7/2001 | Vrba et al. |
| 6,312,465 B1 | 11/2001 | Griffin et al. |
| 6,346,074 B1 | 2/2002 | Roth |
| 6,402,780 B2 | 6/2002 | Williamson, IV et al. |
| 6,458,153 B1 | 10/2002 | Bailey et al. |
| 6,669,724 B2 | 12/2003 | Park et al. |
| 6,733,525 B2 | 5/2004 | Yang et al. |
| 6,752,813 B2 | 6/2004 | Goldfarb et al. |
| 6,755,857 B2 | 6/2004 | Peterson et al. |
| 6,926,715 B1 | 8/2005 | Hauck et al. |
| 6,939,370 B2 | 9/2005 | Hartley et al. |
| 7,074,236 B2 | 7/2006 | Rabkin et al. |
| 7,201,772 B2 | 4/2007 | Schwammenthal et al. |
| 7,226,467 B2 | 6/2007 | Lucatero et al. |
| 7,261,686 B2 | 8/2007 | Couvillon, Jr. |
| 7,288,097 B2 | 10/2007 | Séguin |
| 7,442,204 B2 | 10/2008 | Schwammenthal et al. |
| 7,556,632 B2 | 7/2009 | Zadno |
| 7,563,267 B2 | 7/2009 | Goldfarb et al. |
| 7,563,273 B2 | 7/2009 | Goldfarb et al. |
| 7,608,091 B2 | 10/2009 | Goldfarb et al. |
| 7,635,329 B2 | 12/2009 | Goldfarb et al. |
| 7,655,015 B2 | 2/2010 | Goldfarb et al. |
| 7,736,388 B2 | 6/2010 | Goldfarb et al. |
| 7,753,949 B2 | 7/2010 | Lamphere et al. |
| 7,811,296 B2 | 10/2010 | Goldfarb et al. |
| 7,837,727 B2 | 11/2010 | Goetz et al. |
| 7,959,672 B2 | 6/2011 | Salahieh et al. |
| 8,052,592 B2 | 11/2011 | Goldfarb et al. |
| 8,057,493 B2 | 11/2011 | Goldfarb et al. |
| 8,070,802 B2 | 12/2011 | Lamphere et al. |
| D652,927 S | 1/2012 | Braido et al. |
| D653,341 S | 1/2012 | Braido et al. |
| 8,109,996 B2 | 2/2012 | Stacchino et al. |
| D660,433 S | 5/2012 | Braido et al. |
| D660,967 S | 5/2012 | Braido et al. |
| 8,216,256 B2 | 7/2012 | Raschdorf, Jr. et al. |
| 8,313,525 B2 | 11/2012 | Tuval et al. |
| 8,403,983 B2 | 3/2013 | Quadri et al. |
| 8,414,644 B2 | 4/2013 | Quadri et al. |
| 8,449,599 B2 | 5/2013 | Chau et al. |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,585,755 B2 | 11/2013 | Chau et al. |
| 8,628,571 B1 | 1/2014 | Hacohen et al. |
| 8,652,203 B2 | 2/2014 | Quadri et al. |
| 8,657,872 B2 | 2/2014 | Seguin |
| 8,728,155 B2 | 5/2014 | Montorfano et al. |
| 8,747,460 B2 | 6/2014 | Tuval et al. |
| 8,784,481 B2 | 7/2014 | Alkhatib et al. |
| 8,852,272 B2 | 10/2014 | Gross et al. |
| 8,870,948 B1 | 10/2014 | Erzberger et al. |
| 8,870,950 B2 | 10/2014 | Hacohen |
| 8,961,595 B2 | 2/2015 | Alkhatib |
| 8,986,375 B2 | 3/2015 | Garde et al. |
| 8,992,604 B2 | 3/2015 | Gross et al. |
| 8,998,982 B2 | 4/2015 | Richter et al. |
| 9,017,399 B2 | 4/2015 | Gross et al. |
| D730,520 S | 5/2015 | Braido et al. |
| D730,521 S | 5/2015 | Braido et al. |
| 9,023,100 B2 | 5/2015 | Quadri et al. |
| D732,666 S | 6/2015 | Nguyen et al. |
| 9,050,188 B2 | 6/2015 | Schweich, Jr. et al. |
| 9,060,858 B2 | 6/2015 | Thornton et al. |
| 9,072,603 B2 | 7/2015 | Tuval et al. |
| 9,095,434 B2 | 8/2015 | Rowe |
| 9,119,719 B2 | 9/2015 | Zipory et al. |
| 9,125,740 B2 | 9/2015 | Morriss et al. |
| 9,132,009 B2 | 9/2015 | Hacohen et al. |
| 9,173,659 B2 | 11/2015 | Bodewadt et al. |
| 9,180,009 B2 | 11/2015 | Majkrzak et al. |
| 9,232,995 B2 | 1/2016 | Kovalsky et al. |
| 9,241,790 B2 | 1/2016 | Lane et al. |
| 9,241,791 B2 | 1/2016 | Braido et al. |
| 9,241,792 B2 | 1/2016 | Benichou et al. |
| 9,248,014 B2 | 2/2016 | Lane et al. |
| 9,277,994 B2 | 3/2016 | Miller et al. |
| 9,295,551 B2 | 3/2016 | Straubinger et al. |
| 9,295,552 B2 | 3/2016 | McLean et al. |
| 9,320,591 B2 | 4/2016 | Bolduc |
| D755,384 S | 5/2016 | Pesce et al. |
| 9,345,573 B2 | 5/2016 | Nyuli et al. |
| 9,358,107 B2 | 6/2016 | Nguyen et al. |
| 9,387,078 B2 | 7/2016 | Gross et al. |
| 9,393,110 B2 | 7/2016 | Levi et al. |
| 9,439,757 B2 | 9/2016 | Wallace et al. |
| 9,445,893 B2 | 9/2016 | Vaturi |
| 9,463,102 B2 | 10/2016 | Kelly |
| 9,492,273 B2 | 11/2016 | Wallace et al. |
| 9,532,870 B2 | 1/2017 | Cooper et al. |
| 9,554,897 B2 | 1/2017 | Lane et al. |
| 9,554,899 B2 | 1/2017 | Granada et al. |
| 9,561,103 B2 | 2/2017 | Granada et al. |
| 9,566,152 B2 | 2/2017 | Schweich, Jr. et al. |
| 9,572,665 B2 | 2/2017 | Lane et al. |
| 9,597,182 B2 | 3/2017 | Straubinger et al. |
| 9,629,716 B2 | 4/2017 | Seguin |
| 9,662,203 B2 | 5/2017 | Sheahan et al. |
| 9,681,952 B2 | 6/2017 | Hacohen et al. |
| 9,717,591 B2 | 8/2017 | Chau et al. |
| 9,763,657 B2 | 9/2017 | Hacohen et al. |
| 9,770,256 B2 | 9/2017 | Cohen et al. |
| D800,908 S | 10/2017 | Hariton et al. |
| 9,788,941 B2 | 10/2017 | Hacohen |
| 9,895,226 B1 | 2/2018 | Harari et al. |
| 9,974,651 B2 | 5/2018 | Hariton et al. |
| 10,010,414 B2 | 7/2018 | Cooper et al. |
| 10,076,415 B1 | 9/2018 | Metchik et al. |
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,143,552 B2 | 12/2018 | Wallace et al. |
| 10,149,761 B2 | 12/2018 | Granada et al. |
| 10,154,906 B2 | 12/2018 | Granada et al. |
| 10,159,570 B1 | 12/2018 | Metchik et al. |
| 10,182,908 B2 | 1/2019 | Tubishevitz et al. |
| 10,226,341 B2 | 3/2019 | Gross et al. |
| 10,231,837 B1 | 3/2019 | Metchik et al. |
| 10,238,493 B1 | 3/2019 | Metchik et al. |
| 10,245,143 B2 | 4/2019 | Gross et al. |
| 10,245,144 B1 | 4/2019 | Metchik et al. |
| 10,299,927 B2 | 5/2019 | McLean et al. |
| 10,321,995 B1 | 6/2019 | Christianson et al. |
| 10,322,020 B2 | 6/2019 | Lam et al. |
| 10,327,895 B2 | 6/2019 | Lozonschi et al. |
| 10,335,278 B2 | 7/2019 | McLean et al. |
| 10,357,360 B2 | 7/2019 | Hariton et al. |
| 10,376,361 B2 | 8/2019 | Gross et al. |
| 10,390,952 B2 | 8/2019 | Hariton et al. |

(56) References Cited

U.S. PATENT DOCUMENTS

| | | |
|---|---|---|
| 10,426,610 B2 | 10/2019 | Hariton et al. |
| 10,463,487 B2 | 11/2019 | Hariton et al. |
| 10,463,488 B2 | 11/2019 | Hariton et al. |
| 10,507,105 B2 | 12/2019 | Hariton et al. |
| 10,507,108 B2 | 12/2019 | Delgado et al. |
| 10,507,109 B2 | 12/2019 | Metchik et al. |
| 10,512,456 B2 | 12/2019 | Hacohen et al. |
| 10,517,719 B2 | 12/2019 | Miller et al. |
| 10,524,792 B2 | 1/2020 | Hernandez et al. |
| 10,524,903 B2 | 1/2020 | Hariton et al. |
| 10,531,872 B2 | 1/2020 | Hacohen et al. |
| 10,548,731 B2 | 2/2020 | Lashinski et al. |
| 10,575,948 B2 | 3/2020 | Iamberger et al. |
| 10,595,992 B2 | 3/2020 | Chambers |
| 10,595,997 B2 | 3/2020 | Metchik et al. |
| 10,610,358 B2 | 4/2020 | Vidlund et al. |
| 10,646,342 B1 | 5/2020 | Marr et al. |
| 10,667,908 B2 | 6/2020 | Hariton et al. |
| 10,682,227 B2 | 6/2020 | Hariton et al. |
| 10,695,177 B2 | 6/2020 | Hariton et al. |
| 10,702,385 B2 | 7/2020 | Hacohen |
| 10,722,360 B2 | 7/2020 | Hariton et al. |
| 10,758,342 B2 | 9/2020 | Chau et al. |
| 10,758,344 B2 | 9/2020 | Hariton et al. |
| 10,799,345 B2 | 10/2020 | Hariton et al. |
| 10,813,760 B2 | 10/2020 | Metchik et al. |
| 10,820,998 B2 | 11/2020 | Marr et al. |
| 10,842,627 B2 | 11/2020 | Delgado et al. |
| 10,849,748 B2 | 12/2020 | Hariton et al. |
| 10,856,972 B2 | 12/2020 | Hariton et al. |
| 10,856,975 B2 | 12/2020 | Hariton et al. |
| 10,856,978 B2 | 12/2020 | Straubinger et al. |
| 10,864,078 B2 | 12/2020 | Hariton et al. |
| 10,874,514 B2 | 12/2020 | Dixon et al. |
| 10,881,511 B2 | 1/2021 | Hariton et al. |
| 10,888,422 B2 | 1/2021 | Hariton et al. |
| 10,888,644 B2 | 1/2021 | Ratz et al. |
| 10,905,548 B2 | 2/2021 | Hariton et al. |
| 10,905,549 B2 | 2/2021 | Hariton et al. |
| 10,905,552 B2 | 2/2021 | Dixon et al. |
| 10,905,554 B2 | 2/2021 | Cao |
| 10,918,483 B2 | 2/2021 | Metchik et al. |
| 10,925,595 B2 | 2/2021 | Hacohen et al. |
| 10,945,844 B2 | 3/2021 | McCann et al. |
| 10,973,636 B2 | 4/2021 | Hariton et al. |
| 10,993,809 B2 | 5/2021 | McCann et al. |
| 11,083,582 B2 | 8/2021 | McCann et al. |
| 11,147,672 B2 | 10/2021 | McCann et al. |
| 2001/0005787 A1 | 6/2001 | Oz et al. |
| 2001/0021872 A1 | 9/2001 | Bailey et al. |
| 2002/0013571 A1 | 1/2002 | Goldfarb et al. |
| 2002/0032481 A1 | 3/2002 | Gabbay |
| 2003/0050694 A1 | 3/2003 | Yang et al. |
| 2003/0074059 A1 | 4/2003 | Nguyen et al. |
| 2004/0030382 A1 | 2/2004 | St. Goar et al. |
| 2004/0186558 A1 | 9/2004 | Pavcnik et al. |
| 2004/0210304 A1 | 10/2004 | Seguin et al. |
| 2004/0236354 A1 | 11/2004 | Seguin |
| 2004/0249433 A1 | 12/2004 | Freitag |
| 2005/0027348 A1 | 2/2005 | Case et al. |
| 2005/0080474 A1 | 4/2005 | Andreas et al. |
| 2005/0085900 A1 | 4/2005 | Case et al. |
| 2005/0137681 A1 | 6/2005 | Shoemaker et al. |
| 2005/0137691 A1 | 6/2005 | Salahieh et al. |
| 2005/0137692 A1 | 6/2005 | Haug et al. |
| 2005/0137697 A1 | 6/2005 | Salahieh et al. |
| 2005/0203618 A1 | 9/2005 | Sharkawy et al. |
| 2005/0240200 A1 | 10/2005 | Bergheim |
| 2005/0256566 A1 | 11/2005 | Gabbay |
| 2006/0004469 A1 | 1/2006 | Sokel |
| 2006/0020275 A1 | 1/2006 | Goldfarb et al. |
| 2006/0020327 A1 | 1/2006 | Lashinski et al. |
| 2006/0030863 A1 | 2/2006 | Fields et al. |
| 2006/0052867 A1 | 3/2006 | Revuelta et al. |
| 2006/0184203 A1 | 8/2006 | Martin et al. |
| 2006/0195183 A1 | 8/2006 | Navia et al. |
| 2006/0216404 A1 | 9/2006 | Seyler et al. |
| 2006/0229708 A1 | 10/2006 | Powell et al. |
| 2006/0259137 A1 | 11/2006 | Artof et al. |
| 2006/0282150 A1 | 12/2006 | Olson et al. |
| 2007/0016286 A1 | 1/2007 | Herrmann et al. |
| 2007/0038293 A1 | 2/2007 | St. Goar et al. |
| 2007/0056346 A1 | 3/2007 | Spenser et al. |
| 2007/0078510 A1 | 4/2007 | Ryan |
| 2007/0197858 A1 | 8/2007 | Goldfarb et al. |
| 2007/0198077 A1 | 8/2007 | Cully et al. |
| 2007/0213810 A1 | 9/2007 | Newhauser et al. |
| 2007/0219630 A1 | 9/2007 | Chu |
| 2007/0239273 A1 | 10/2007 | Allen |
| 2007/0244546 A1 | 10/2007 | Francis |
| 2008/0065011 A1 | 3/2008 | Marchand et al. |
| 2008/0071361 A1 | 3/2008 | Tuval et al. |
| 2008/0071369 A1 | 3/2008 | Tuval et al. |
| 2008/0082166 A1 | 4/2008 | Styrc et al. |
| 2008/0132989 A1 | 6/2008 | Snow et al. |
| 2008/0147182 A1 | 6/2008 | Righini et al. |
| 2008/0200980 A1 | 8/2008 | Robin et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2009/0005863 A1 | 1/2009 | Goetz et al. |
| 2009/0125098 A1 | 5/2009 | Chuter |
| 2009/0157175 A1 | 6/2009 | Benichou |
| 2009/0259306 A1 | 10/2009 | Rowe |
| 2009/0281619 A1 | 11/2009 | Le et al. |
| 2010/0022823 A1 | 1/2010 | Goldfarb et al. |
| 2010/0023120 A1 | 1/2010 | Holecek et al. |
| 2010/0049313 A1 | 2/2010 | Alon et al. |
| 2010/0100167 A1 | 4/2010 | Bortlein et al. |
| 2010/0161036 A1 | 6/2010 | Pintor et al. |
| 2010/0256737 A1 | 10/2010 | Pollock et al. |
| 2010/0312333 A1 | 12/2010 | Navia et al. |
| 2010/0331971 A1 | 12/2010 | Keranen et al. |
| 2011/0004227 A1 | 1/2011 | Goldfarb et al. |
| 2011/0004299 A1 | 1/2011 | Navia et al. |
| 2011/0029072 A1 | 2/2011 | Gabbay |
| 2011/0066233 A1 | 3/2011 | Thornton et al. |
| 2011/0137397 A1 | 6/2011 | Chau et al. |
| 2011/0144742 A1 | 6/2011 | Madrid et al. |
| 2011/0208283 A1 | 8/2011 | Rust |
| 2011/0224785 A1 | 9/2011 | Hacohen |
| 2011/0245911 A1 | 10/2011 | Quill et al. |
| 2011/0264196 A1 | 10/2011 | Savage et al. |
| 2011/0282439 A1 | 11/2011 | Thill et al. |
| 2011/0306916 A1 | 12/2011 | Nitzan et al. |
| 2011/0307049 A1 | 12/2011 | Kao |
| 2011/0313515 A1 | 12/2011 | Quadri et al. |
| 2011/0319989 A1 | 12/2011 | Lane et al. |
| 2012/0016468 A1 | 1/2012 | Robin et al. |
| 2012/0022629 A1 | 1/2012 | Perera et al. |
| 2012/0022639 A1 | 1/2012 | Hacohen et al. |
| 2012/0059458 A1 | 3/2012 | Buchbinder |
| 2012/0065464 A1 | 3/2012 | Ellis et al. |
| 2012/0078237 A1 | 3/2012 | Wang et al. |
| 2012/0078353 A1 | 3/2012 | Quadri et al. |
| 2012/0089223 A1 | 4/2012 | Nguyen et al. |
| 2012/0101571 A1 | 4/2012 | Thambar et al. |
| 2012/0165930 A1 | 6/2012 | Gifford, III et al. |
| 2012/0296418 A1 | 11/2012 | Bonyuet et al. |
| 2012/0300063 A1 | 11/2012 | Majkrzak et al. |
| 2012/0310328 A1 | 12/2012 | Olson et al. |
| 2012/0323316 A1 | 12/2012 | Chau et al. |
| 2013/0018458 A1 | 1/2013 | Yohanan et al. |
| 2013/0046373 A1 | 2/2013 | Cartledge et al. |
| 2013/0066342 A1 | 3/2013 | Dell et al. |
| 2013/0144381 A1 | 6/2013 | Quadri et al. |
| 2013/0178930 A1 | 7/2013 | Straubinger et al. |
| 2013/0190861 A1 | 7/2013 | Chau et al. |
| 2013/0231735 A1 | 9/2013 | Deem et al. |
| 2013/0253643 A1 | 9/2013 | Rolando et al. |
| 2013/0261738 A1 | 10/2013 | Clague et al. |
| 2013/0274870 A1 | 10/2013 | Lombardi et al. |
| 2013/0282059 A1 | 10/2013 | Ketai et al. |
| 2013/0289711 A1 | 10/2013 | Liddy et al. |

(56) References Cited

U.S. PATENT DOCUMENTS

| | | |
|---|---|---|
| 2013/0289740 A1 | 10/2013 | Liddy et al. |
| 2013/0304200 A1 | 11/2013 | McLean et al. |
| 2014/0000112 A1 | 1/2014 | Braido et al. |
| 2014/0018915 A1 | 1/2014 | Biadillah et al. |
| 2014/0067050 A1 | 3/2014 | Costello et al. |
| 2014/0142688 A1 | 5/2014 | Duffy et al. |
| 2014/0172077 A1 | 6/2014 | Bruchman et al. |
| 2014/0172082 A1 | 6/2014 | Bruchman et al. |
| 2014/0194981 A1 | 7/2014 | Menk et al. |
| 2014/0207231 A1 | 7/2014 | Hacohen et al. |
| 2014/0222136 A1 | 8/2014 | Geist et al. |
| 2014/0222142 A1 | 8/2014 | Kovalsky et al. |
| 2014/0236287 A1 | 8/2014 | Clague et al. |
| 2014/0236289 A1 | 8/2014 | Alkhatib |
| 2014/0249622 A1 | 9/2014 | Carmi et al. |
| 2014/0257467 A1 | 9/2014 | Lane et al. |
| 2014/0277409 A1 | 9/2014 | Bortlein et al. |
| 2014/0277411 A1 | 9/2014 | Bortlein et al. |
| 2014/0277418 A1 | 9/2014 | Miller |
| 2014/0277422 A1 | 9/2014 | Ratz et al. |
| 2014/0277427 A1 | 9/2014 | Ratz et al. |
| 2014/0296969 A1 | 10/2014 | Tegels et al. |
| 2014/0324164 A1 | 10/2014 | Gross et al. |
| 2014/0343670 A1 | 11/2014 | Bakis et al. |
| 2014/0358222 A1 | 12/2014 | Gorman, III et al. |
| 2014/0358224 A1 | 12/2014 | Tegels et al. |
| 2015/0018944 A1 | 1/2015 | O'Connell et al. |
| 2015/0032205 A1 | 1/2015 | Matheny |
| 2015/0142100 A1 | 5/2015 | Morriss et al. |
| 2015/0142103 A1 | 5/2015 | Vidlund |
| 2015/0157457 A1 | 6/2015 | Hacohen |
| 2015/0157458 A1 | 6/2015 | Thambar et al. |
| 2015/0173896 A1 | 6/2015 | Richter et al. |
| 2015/0173897 A1 | 6/2015 | Raanani et al. |
| 2015/0196390 A1 | 7/2015 | Ma et al. |
| 2015/0196393 A1 | 7/2015 | Vidlund et al. |
| 2015/0216661 A1 | 8/2015 | Hacohen et al. |
| 2015/0238313 A1 | 8/2015 | Spence et al. |
| 2015/0245934 A1 | 9/2015 | Lombardi et al. |
| 2015/0250588 A1 | 9/2015 | Yang et al. |
| 2015/0272730 A1 | 10/2015 | Melnick et al. |
| 2015/0272734 A1 | 10/2015 | Sheps et al. |
| 2015/0320556 A1 | 11/2015 | Levi et al. |
| 2015/0327994 A1 | 11/2015 | Morriss et al. |
| 2015/0328000 A1 | 11/2015 | Ratz et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0351906 A1 | 12/2015 | Hammer et al. |
| 2015/0359629 A1 | 12/2015 | Ganesan et al. |
| 2015/0359631 A1 | 12/2015 | Sheahan et al. |
| 2016/0030169 A1 | 2/2016 | Shahriari |
| 2016/0030171 A1 | 2/2016 | Quijano et al. |
| 2016/0089482 A1 | 3/2016 | Siegenthaler |
| 2016/0100939 A1 | 4/2016 | Amstrong et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0158497 A1 | 6/2016 | Tran et al. |
| 2016/0175095 A1 | 6/2016 | Dienno et al. |
| 2016/0184098 A1 | 6/2016 | Vaturi |
| 2016/0262885 A1 | 9/2016 | Sandstrom et al. |
| 2016/0270911 A1 | 9/2016 | Ganesan et al. |
| 2016/0310268 A1 | 10/2016 | Oba et al. |
| 2016/0317305 A1 | 11/2016 | Pelled et al. |
| 2016/0324633 A1 | 11/2016 | Gross et al. |
| 2016/0324635 A1 | 11/2016 | Vidlund et al. |
| 2016/0331525 A1 | 11/2016 | Straubinger et al. |
| 2016/0331526 A1 | 11/2016 | Schweich, Jr. et al. |
| 2016/0338706 A1 | 11/2016 | Rowe |
| 2016/0374801 A1 | 12/2016 | Jimenez et al. |
| 2016/0374802 A1 | 12/2016 | Levi et al. |
| 2017/0042678 A1 | 2/2017 | Ganesan et al. |
| 2017/0049435 A1 | 2/2017 | Sauer et al. |
| 2017/0056166 A1 | 3/2017 | Ratz et al. |
| 2017/0056171 A1 | 3/2017 | Cooper et al. |
| 2017/0065411 A1 | 3/2017 | Grundeman et al. |
| 2017/0128205 A1 | 5/2017 | Tamir et al. |
| 2017/0135816 A1 | 5/2017 | Lashinski et al. |
| 2017/0189174 A1 | 7/2017 | Braido et al. |
| 2017/0209264 A1 | 7/2017 | Chau et al. |
| 2017/0224323 A1 | 8/2017 | Rowe et al. |
| 2017/0231757 A1 | 8/2017 | Gassier |
| 2017/0231759 A1 | 8/2017 | Geist et al. |
| 2017/0231766 A1 | 8/2017 | Hariton et al. |
| 2017/0239048 A1 | 8/2017 | Goldfarb et al. |
| 2017/0325948 A1 | 11/2017 | Wallace et al. |
| 2017/0333183 A1 | 11/2017 | Backus |
| 2017/0333187 A1 | 11/2017 | Hariton et al. |
| 2017/0367823 A1 | 12/2017 | Hariton et al. |
| 2018/0000580 A1 | 1/2018 | Wallace et al. |
| 2018/0021129 A1 | 1/2018 | Peterson et al. |
| 2018/0028215 A1 | 2/2018 | Cohen |
| 2018/0049873 A1 | 2/2018 | Manash et al. |
| 2018/0055630 A1 | 3/2018 | Patel et al. |
| 2018/0098850 A1 | 4/2018 | Rafiee et al. |
| 2018/0116843 A1 | 5/2018 | Schreck et al. |
| 2018/0125644 A1 | 5/2018 | Conklin |
| 2018/0153689 A1 | 6/2018 | Maimon et al. |
| 2018/0206983 A1 | 7/2018 | Noe et al. |
| 2018/0214263 A1 | 8/2018 | Rolando et al. |
| 2018/0250126 A1 | 9/2018 | O'Connor et al. |
| 2018/0250130 A1 | 9/2018 | Hariton et al. |
| 2018/0250147 A1 | 9/2018 | Syed |
| 2018/0256323 A1 | 9/2018 | Hariton et al. |
| 2018/0256325 A1 | 9/2018 | Hariton et al. |
| 2018/0271654 A1 | 9/2018 | Hariton et al. |
| 2018/0271655 A1 | 9/2018 | Hariton et al. |
| 2018/0289479 A1 | 10/2018 | Hariton et al. |
| 2018/0296336 A1 | 10/2018 | Cooper et al. |
| 2018/0338829 A1 | 11/2018 | Hariton et al. |
| 2018/0338830 A1 | 11/2018 | Hariton et al. |
| 2018/0338831 A1 | 11/2018 | Hariton et al. |
| 2018/0344457 A1 | 12/2018 | Gross et al. |
| 2018/0353294 A1 | 12/2018 | Calomeni et al. |
| 2018/0360457 A1 | 12/2018 | Ellis et al. |
| 2019/0015093 A1 | 1/2019 | Hacohen et al. |
| 2019/0053896 A1 | 2/2019 | Adamek-Bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0083242 A1 | 3/2019 | Hariton et al. |
| 2019/0083243 A1 | 3/2019 | Hariton et al. |
| 2019/0083246 A1 | 3/2019 | Hariton et al. |
| 2019/0083247 A1 | 3/2019 | Hariton et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0192295 A1 | 6/2019 | Spence et al. |
| 2019/0328519 A1 | 10/2019 | Hariton et al. |
| 2019/0336280 A1 | 11/2019 | Naor et al. |
| 2019/0343627 A1 | 11/2019 | Hariton et al. |
| 2019/0350701 A1 | 11/2019 | Adamek-Bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2019/0388223 A1 | 12/2019 | Hariton et al. |
| 2020/0000449 A1 | 1/2020 | Goldfarb et al. |
| 2020/0000579 A1 | 1/2020 | Manash et al. |
| 2020/0015964 A1 | 1/2020 | Noe et al. |
| 2020/0030098 A1 | 1/2020 | Delgado et al. |
| 2020/0046497 A1 | 2/2020 | Hariton et al. |
| 2020/0054335 A1 | 2/2020 | Hernandez et al. |
| 2020/0054451 A1 | 2/2020 | Hariton et al. |
| 2020/0060818 A1 | 2/2020 | Geist et al. |
| 2020/0069424 A1 | 3/2020 | Hariton et al. |
| 2020/0113677 A1 | 4/2020 | McCann et al. |
| 2020/0113689 A1 | 4/2020 | McCann et al. |
| 2020/0113692 A1 | 4/2020 | McCann et al. |
| 2020/0129294 A1 | 4/2020 | Hariton et al. |
| 2020/0138567 A1 | 5/2020 | Marr et al. |
| 2020/0146671 A1 | 5/2020 | Hacohen et al. |

(56) References Cited

U.S. PATENT DOCUMENTS

| | | |
|---|---|---|
| 2020/0163761 A1 | 5/2020 | Hariton et al. |
| 2020/0214832 A1 | 7/2020 | Metchik et al. |
| 2020/0237512 A1 | 7/2020 | McCann et al. |
| 2020/0246136 A1 | 8/2020 | Marr et al. |
| 2020/0246140 A1 | 8/2020 | Hariton et al. |
| 2020/0253600 A1 | 8/2020 | Darabian |
| 2020/0261094 A1 | 8/2020 | Goldfarb et al. |
| 2020/0315786 A1 | 10/2020 | Metchik et al. |
| 2020/0337842 A1 | 10/2020 | Metchik et al. |
| 2021/0085455 A1 | 3/2021 | Bateman et al. |
| 2021/0093449 A1 | 4/2021 | Hariton et al. |
| 2021/0113331 A1 | 4/2021 | Quadri et al. |

FOREIGN PATENT DOCUMENTS

| | | |
|---|---|---|
| EP | 1264582 A2 | 12/2002 |
| EP | 1637092 A2 | 3/2006 |
| EP | 2349124 B1 | 10/2018 |
| EP | 3583922 A1 | 12/2019 |
| EP | 3270825 B1 | 4/2020 |
| EP | 2485795 B1 | 9/2020 |
| WO | WO 2003/020179 A1 | 3/2003 |
| WO | WO 2004/028399 A2 | 4/2004 |
| WO | WO 2006/007389 A1 | 1/2006 |
| WO | WO 2006/086434 A1 | 8/2006 |
| WO | WO 2006/116558 A2 | 11/2006 |
| WO | WO 2006/128193 A2 | 11/2006 |
| WO | WO 2007/047488 A2 | 4/2007 |
| WO | WO 2008/029296 A2 | 3/2008 |
| WO | WO 2009/091509 A1 | 7/2009 |
| WO | WO 2010/006627 A1 | 1/2010 |
| WO | WO 2010/027485 A1 | 3/2010 |
| WO | WO 2010/045297 A2 | 4/2010 |
| WO | WO 2010/057262 A1 | 5/2010 |
| WO | WO 2011/144351 A2 | 11/2011 |
| WO | WO 2012/011108 A2 | 1/2012 |
| WO | WO 2012/036740 A2 | 3/2012 |
| WO | WO 2012/048035 A2 | 4/2012 |
| WO | WO 2013/059747 A1 | 4/2013 |
| WO | WO 2013/072496 A1 | 5/2013 |
| WO | WO 2013/078497 A1 | 6/2013 |
| WO | WO 2013/114214 A2 | 8/2013 |
| WO | WO 2013/175468 A2 | 11/2013 |
| WO | WO 2014/115149 A2 | 7/2014 |
| WO | WO 2014/144937 A2 | 9/2014 |
| WO | WO 2014/164364 A1 | 10/2014 |
| WO | WO 2016/016899 A1 | 2/2016 |
| WO | WO 2016/098104 A2 | 6/2016 |
| WO | WO 2016/125160 A1 | 8/2016 |
| WO | WO 2018/025260 A1 | 2/2018 |
| WO | WO 2018/025263 A2 | 2/2018 |
| WO | WO 2018/029680 A1 | 2/2018 |
| WO | WO 2018/039631 A1 | 3/2018 |
| WO | WO 2018/112429 A1 | 6/2018 |
| WO | WO 2018/118717 A1 | 6/2018 |
| WO | WO 2018/131042 A1 | 7/2018 |
| WO | WO 2018/131043 A1 | 7/2018 |
| WO | WO 2019/027507 A1 | 2/2019 |
| WO | WO 2019/195860 A2 | 10/2019 |
| WO | WO 2020/167677 A1 | 8/2020 |

OTHER PUBLICATIONS

International Search Report dated Mar. 27, 2018, by the European Patent Office in PCT/IL2017/050849 (5 pages).
International Search Report dated May 30, 2016, by the European Patent Office in PCT/IL2016/050125 (6 pages).
International Search Report dated Nov. 24, 2017, by the European Patent Office in PCT/IL2017/050873 (5 pages).
International Search Report dated Oct. 27, 2015, by the European Patent Office in PCT/IL2015/050792 (3 pages).
International Search Report dated Sep. 4, 2014, by the European Patent Office in PCT/IL2014/050087 (6 pages).

Written Opinion of the International Searching Authority issued by the United States Patent and Trademark Office in PCT/IL2011/000582 (12 pages).
Written Opinion of the International Searching Authority issued by the European Patent Office in PCT/IL2017/050849 (10 pages).
Written Opinion of the International Searching Authority issued by the European Patent Office in PCT/IL2016/050125 (7 pages).
Written Opinion of the International Searching Authority issued by the European Patent Office in PCT/IL2014/050087 (10 pages).
Written Opinion of the International Searching Authority issued by the European Patent Office in PCT/IL2015/050792 (5 pages).
Written Opinion of the International Searching Authority issued by the European Patent Office in PCT/IL2017/050873 (12 pages).
Sündermann, Simon H. et al., *Feasibility of the Engager™ aortic transcatheter valve system using a flexible over-the-wire design*, 42 European Journal of Cardio-Thoracic Surgery, Jun. 27, 2012, at e48 (5 pages).
Symetis S.A., Clinical Investigation Plan for Acurate Neo™ TA Delivery System, Protocol 2015-01, ver. 2, ClinicalTrials.gov Identifier NCT02950428, Sep. 8, 2015 (76 pages).
Tchetche, Didier et al., *New-generation TAVI devices: description and specifications*, 10 EuroIntervention (Supplement), Sep. 2014, at U90 (11 pages).
Batista, Randas J. V. et al., *Partial Left Ventriculectomy to Treat End-Stage Heart Disease*, 64 Annals Thoracic Surgery 634-38 (1997) (5 pages).
Beall, Jr., Arthur C. et al., *Clinical Experience with a Dacron Velour-Covered Teflon-Disc Mitral-Valve Prosthesis*, 5 Annals Thoracic Surgery 402-10 (1968) (9 pages).
Fucci, Carlo et al., *Improved Results with Mitral Valve Repair Using New Surgical Techniques*, 9 Eur. J. Cardiothoracic Surgery 621-27 (1995) (7 pages).
Maisano, Francesco et al., *The Edge-To-Edge Technique: A Simplified Method to Correct Mitral Insufficiency*, 13 Eur. J. Cardiothoracic Surgery 240-46 (1998) (7 pages).
Stone, Gregg W. et al., *Clinical Trial Design Principles and Endpoint Definitions for Transcatheter Mitral Valve Repair and Replacement: Part 1: Clinical Trial Design Principles*, 66 J. Am. C. Cardiology 278-307 (2015) (30 pages).
*Edwards Lifesciences Corp. v. Cardiovalve Ltd.*, IPR2021-00383, Exhibit 1014: Transcript of proceedings held May 20, 2021 (May 26, 2021) (21 pages).
*Edwards Lifesciences Corp. v. Cardiovalve Ltd.*, IPR2021-00383, Exhibit 1015: Facilitate, Merriam-Webster.com, https://www. www.merriam-webster.com/dictionary/facilitate (accessed May 27, 2021) (5 pages).
*Edwards Lifesciences Corp. v. Cardiovalve Ltd.*, IPR2021-00383, Paper 12: Petitioners' Authorized Reply to Patent Owner's Preliminary Response (May 27, 2021) (9 pages).
*Edwards Lifesciences Corp. v. Cardiovalve Ltd.*, IPR2021-00383, Paper 13: Patent Owner's Authorized Surreply to Petitioner's Reply to Patent Owner's Preliminary Response (Jun. 4, 2021) (8 pages).
*Edwards Lifesciences Corp. v. Cardiovalve Ltd.*, IPR2021-00383, Paper 16: Institution Decision (Jul. 20, 2021) (51 pages).
Poirier, Nancy et al., *A Novel Repair for Patients with Atrioventricular Septal Defect Requiring Reoperation for Left Atrioventricular Valve Regurgitation*, 18 Eur. J. Cardiothoracic Surgery 54-61 (2000) (8 pages).
Ando, Tomo et al., *Iatrogenic Ventricular Septal Defect Following Transcatheter Aortic Valve Replacement: A Systematic Review*, 25 Heart, Lung, and Circulation 968-74 (2016) (7 pages).
Urina, Marina et al., *Transseptal Transcatheter Mitral Valve Replacement Using Balloon-Expandable Transcatheter Heart Valves*, JACC: Cardiovascular Interventions 1905-19 (2017) (15 pages).
*Edwards Lifesciences Corp. v. Cardiovalve Ltd.*, IPR2021-00383, Exhibit 2009: Percutaneous Mitral Leaflet Repair: MitraClip Therapy for Mitral Regurgitation (Aug. 17, 2012) (8 pages).
*Edwards Lifesciences Corp. v. Cardiovalve Ltd.*, IPR2021-00383, Exhibit 2010: Deposition of Dr. Ivan Vesely, Ph.D. (Sep. 27, 2021) (170 pages).
*Edwards Lifesciences Corp. v. Cardiovalve Ltd.*, IPR2021-00383, Exhibit 2014: Second Declaration of Dr. Michael Sacks (Oct. 13, 2021) (28 pages).

(56) References Cited

OTHER PUBLICATIONS

*Edwards Lifesciences Corp. v. Cardiovalve Ltd.*, IPR2021-00383, Patent Owner's Contingent Motion to Amend Under 37 C.F.R. § 42.121 (Oct. 13, 2021) (35 pages).

*Edwards Lifesciences Corp. v. Cardiovalve Ltd.*, IPR2021-00383, Patent Owner's Response Pursuant to 37 C.F.R. § 42.120 (Oct. 13, 2021) (75 pages).

Fann, James I. et al., *Beating Heart Catheter-Based Edge-to-Edge Mitral Valve Procedure in a Porcine Model: Efficacy and Healing Response*, 110 Circulation, Aug. 2004, at 988 (6 pages).

Feldman, Ted et al., *Percutaneous Mitral Repair With the MitraClip System: Safety and Midterm Durability in the Initial EVEREST Cohort*, 54 J. Am. Coll. Cardiology, Aug. 2009, at 686 (9 pages).

Feldman, Ted et al., *Percutaneous Mitral Valve Repair Using the Edge-to-Edge Technique: Six-Month Results of the EVEREST Phase I Clinical Trial*, 46 J. Am. Coll. Cardiology, Dec. 2005, at 3134 (7 pages).

Maisano, Francesco et al., *The Evolution From Surgery to Percutaneous Mitral Valve Interventions: The Role of the Edge-to-Edge Technique*, 58 J. Am. Coll. Cardiology, Nov. 2011, at 2174 (9 pages).

*Edwards Lifesciences Corp. v. Cardiovalve Ltd.*, IPR2021-00383, Paper 10: Decision Granting Institution Of Inter Partes Review (Dec. 10, 2021) (42 pages).

*Edwards Lifesciences Corp. v. Cardiovalve Ltd.*, IPR2021-00383, Petitioners' Opposition to Patent Owner's Contingent Motion to Amend (Jan. 5, 2022) (32 pages).

*Edwards Lifesciences Corp. v. Cardiovalve Ltd.*, IPR2021-00383, Petitioners' Reply to Patent Owner's Response (Jan. 5, 2022) (41 pages).

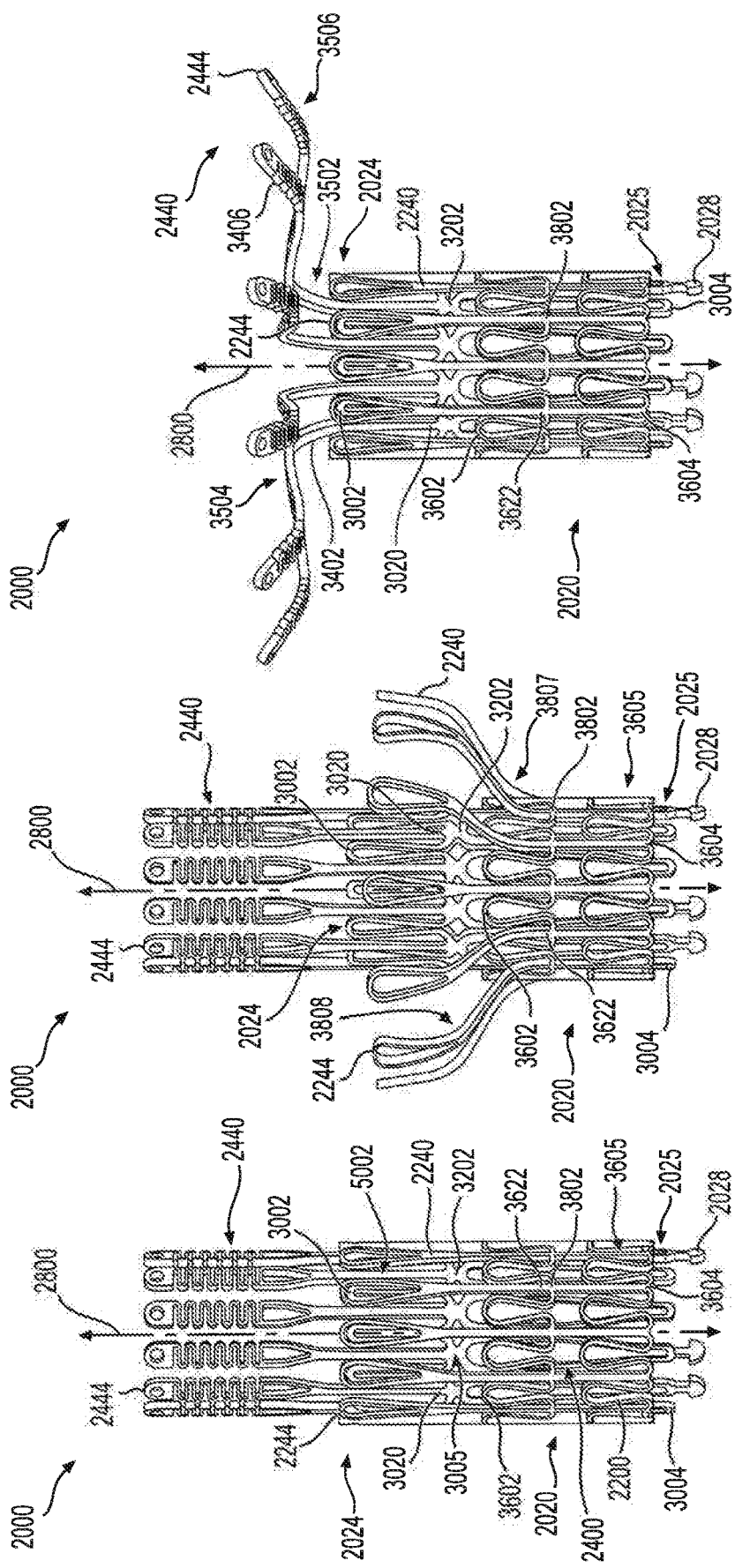

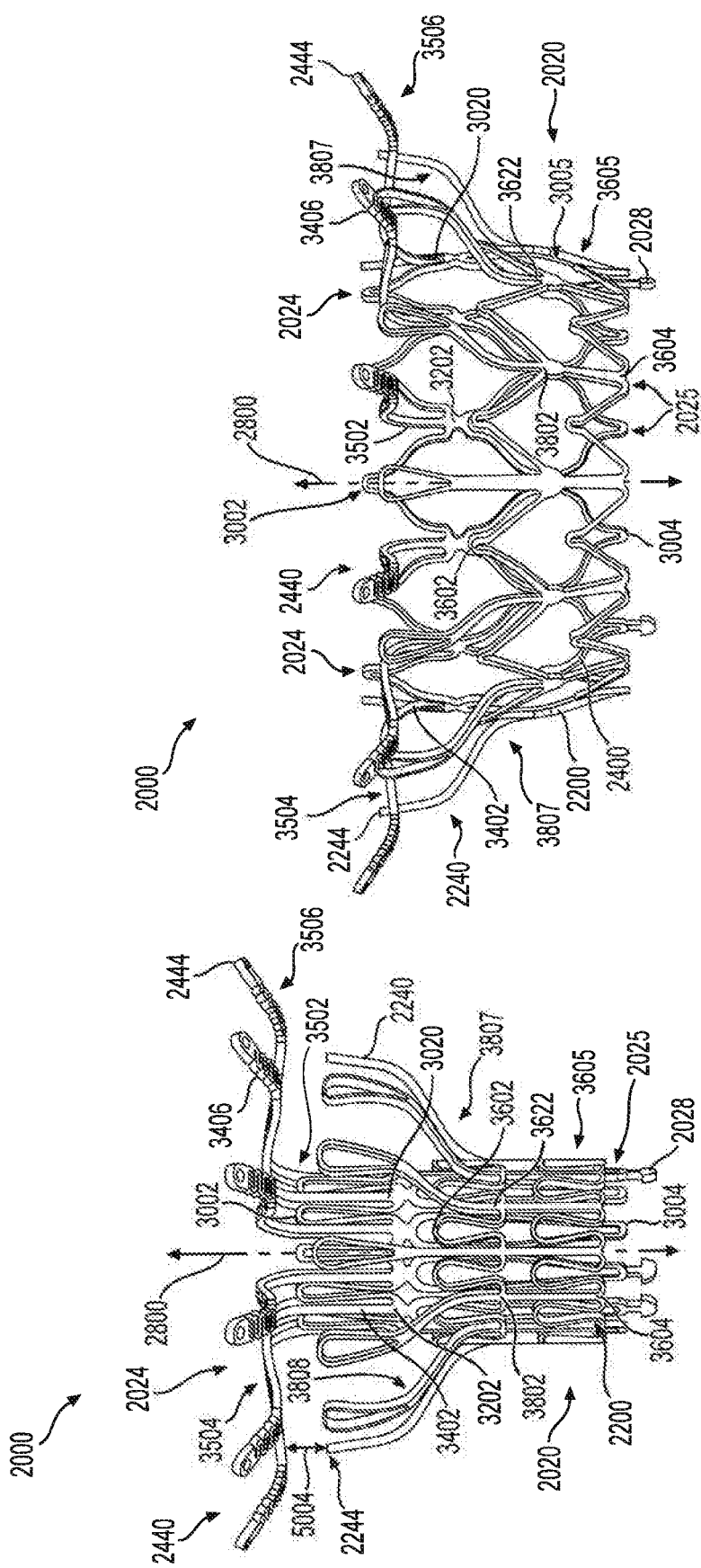

PROSTHETIC VALVE WITH CONNECTING STRUTS OF VARIABLE SIZE AND TISSUE ANCHORING LEGS OF VARIABLE SIZE THAT EXTEND FROM JUNCTIONS

CROSS-REFERENCE TO RELATED APPLICATION

This application claims priority from U.S. Provisional Patent Application No. 62/560,384, filed Sep. 19, 2017, which is hereby incorporated by reference in its entirety.

TECHNICAL FIELD

This disclosure relates generally to prosthetic valves and delivery systems for prosthetic valves. More specifically, this disclosure relates to prosthetic heart valves and methods thereof.

BACKGROUND

The native heart valves (the tricuspid valve, pulmonary valve, mitral valve, and aortic valve) play an important role in regulating flow of blood through the cardiovascular system. However, the native heart valves may become damaged or impaired due to, for example, cardiovascular diseases, infections, or congenital malformations, thus limiting the ability of the native heart valves to regulate blood flow. This deficiency may result in reduced cardiovascular function or even death.

To treat these conditions, prosthetic heart valves may be implanted at or near the site of a damaged or impaired native valve. A prosthetic heart valve may assist or replace the functionality of an impaired native valve, leading to better regulation of blood flow and improved cardiovascular function. However, many existing prosthetic heart valves require implantation via an open heart procedure, which is highly-invasive and may cause life-threatening complications. Other prosthetic valves may be collapsed within a prosthetic valve delivery system and advanced into the heart, at which point the prosthetic valve may be removed from the delivery system and expanded at the native valve site. However, many of these prosthetic valves are large in size and therefore difficult to deliver into the heart without causing damage to healthy tissue along the implantation route. In addition, once these prosthetic valves are situated within the heart, they may be difficult to securely implant at the native valve site due to their complex structure and the limited maneuverability of existing prosthetic valve delivery systems within the heart. Moreover, many prosthetic valves are so large that they may protrude several centimeters into surrounding heart chambers once they are implanted, impairing cardiac filling and causing injury to the anatomy within the heart.

Thus, there remains a need for prosthetic heart valves that are smaller in size but that are still configured to assist or replace the functionality of a diseased or damaged native heart valve. In addition, there remains a need for prosthetic heart valves that are more easily maneuvered into the heart and securely implanted at the site of a native heart valve. Moreover, there remains a need for improved prosthetic heart valve delivery systems that are configured to securely implant a prosthetic heart valve at an implantation site. The present disclosure provides prosthetic heart valves with a reduced axial length such that the prosthetic heart valves may be more easily delivered into the heart and may exhibit less protrusion into the chambers of the heart. The present disclosure also provides improved prosthetic heart valve delivery systems and methods of implanting prosthetic heart valves, such that prosthetic heart valves may be securely anchored at the implantation site.

SUMMARY

The present disclosure discloses prosthetic valves for implantation within a native mitral valve and methods for implanting prosthetic valves within a native mitral valve. Particular examples of the disclosure may pertain to a prosthetic valve formed at least partially of struts having different cross-sectional areas.

According to an exemplary embodiment of the present disclosure, an expandable prosthetic valve for implantation within a native mitral valve is provided. The prosthetic valve includes an expandable valve body having an atrial end, a ventricular end opposite the atrial end, and an intermediate portion extending between the atrial end and the ventricular end. The valve body includes a plurality of struts intersecting at junctions. The prosthetic valve additionally includes a plurality of tissue anchoring legs extending from junctions within the intermediate portion of the valve body. At least one of the tissue anchoring legs has a cross-sectional area that is larger by at least 20% than a cross-sectional area of a strut extending between the at least one tissue anchoring leg and an adjacent tissue anchoring leg.

The cross-sectional area of the at least one tissue anchoring leg is perpendicular to a direction of extension of the at least one tissue anchoring leg. The cross-sectional area of the strut extending between the at least one tissue anchoring leg and the adjacent tissue anchoring leg is perpendicular to a direction of extension of the strut. The cross-sectional area of the at least one tissue anchoring leg is at least four times larger than the cross-sectional area of the strut extending between the at least one tissue anchoring leg and the adjacent tissue anchoring leg. The at least one tissue anchoring leg is configured to extend radially outward from the valve body and in a non-ventricular ventricular direction. The at least one tissue anchoring leg is configured to engage ventricular tissue of the native mitral valve. The prosthetic valve additionally includes a plurality of atrial tissue anchoring arms extending radially outward from junctions within the intermediate portion of the valve body. At least one atrial tissue anchoring arm is configured to extend from the valve body in an atrial direction. The at least one atrial tissue anchoring arm is configured to extend radially outward beyond a terminal end of the at least one tissue anchoring leg. A width of a radial outer surface of the at least one tissue anchoring leg is at least twice as large as a width of a radial outer surface of the strut extending between the at least one tissue anchoring leg and the adjacent tissue anchoring leg. The prosthetic valve additionally includes a tissue anchoring leg base strut extending between the junction from which the at least one tissue anchoring leg extends and a ventricular end of the valve body. The tissue anchoring leg base strut has a cross-sectional area that is substantially equal to the cross-sectional area of the at least one tissue anchoring leg. The cross-sectional area of the at least one tissue anchoring leg is situated within an inner radial half of the at least one tissue anchoring leg. The inner radial half of the at least one tissue anchoring leg has a substantially constant cross-sectional area. The prosthetic valve additionally includes a second strut extending between the at least one tissue anchoring leg and the adjacent tissue anchoring leg. A junction between the strut and the second strut is situated in an axial direction relative to the junction from which the at least one tissue anchoring leg extends. A terminal end of the at least one tissue anchoring leg is configured to be situated in an axial direction relative to the atrial end of the valve body. The at least one tissue anchoring leg and the adjacent tissue anchoring leg do not connect to the valve body at a common point of connection. The at least one tissue anchoring leg extends from a single junction of the valve body. An entire length of the at least one tissue anchoring leg is configured to extend radially outward and toward an atrium upon implantation.

According to another exemplary embodiment of the present disclosure, an expandable prosthetic valve for implantation within a native mitral valve is provided. The prosthetic valve includes an expandable annular outer frame including a plurality of struts intersecting at junctions to form closed cells. The annular outer frame also includes a plurality of ventricular tissue anchoring legs configured to extend radially outward from the junctions of the annular outer frame. The prosthetic valve also includes an inner frame situated at least partially within the annular outer frame. The inner frame includes a plurality of struts intersecting at junctions to form closed cells and a plurality of atrial tissue anchoring arms configured to extend radially outward from the junctions of the inner frame. At least one of the ventricular tissue anchoring legs has a cross-sectional area that is larger by at least 20% than a cross-sectional area of a strut extending between the at least one ventricular tissue anchoring leg and an adjacent ventricular tissue anchoring leg.

At least one of the atrial tissue anchoring arms has a cross-sectional area that is larger by at least 20% than a cross-sectional area of a strut extending between the at least one atrial tissue anchoring arm and an adjacent atrial tissue anchoring arm. At least one of the atrial tissue anchoring arms has a cross-sectional area that is larger by at least 20% than a cross-sectional area of the strut extending between the at least one ventricular tissue anchoring leg and the adjacent ventricular tissue anchoring leg. At least one connection between the annular outer frame and the inner frame is positioned away from respective atrial ends of the annular outer frame and inner frame. At least one connection between the annular outer frame and the inner frame is positioned in a ventricular direction relative to at least one atrial tissue anchoring arm and to the at least one ventricular tissue anchoring leg.

According to a further exemplary embodiment of the present disclosure, an expandable prosthetic valve for implantation within a native mitral valve is provided. The prosthetic valve includes an expandable valve body including a plurality of struts intersecting at junctions. The prosthetic valve also includes a plurality of tissue anchoring legs extending from the junctions of the valve body. At least one of the tissue anchoring legs has a cross-sectional area that is larger by at least 20% than a cross-sectional area of a first strut extending from the at least one tissue anchoring leg toward an adjacent tissue anchoring leg. The at least one tissue anchoring leg and the adjacent tissue anchoring leg are angularly separated by a single junction.

The at least one tissue anchoring leg includes an opening. The prosthetic valve also includes a second strut extending from the adjacent tissue anchoring leg. The first strut and second strut meet at the single junction. The at least one tissue anchoring leg includes at least one bent portion.

Additional features and advantages of the disclosed embodiments will be set forth in part in the description that follows, and in part will be obvious from the description, or may be learned by practice of the disclosed embodiments.

The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIGS. 5A-5E illustrate structural changes in the exemplary frame of FIG. 2A during transitioning of the frame between a radially-contracted configuration and a radially-expanded configuration, consistent with various embodiments of the present disclosure.

DETAILED DESCRIPTION

Figure 1A:
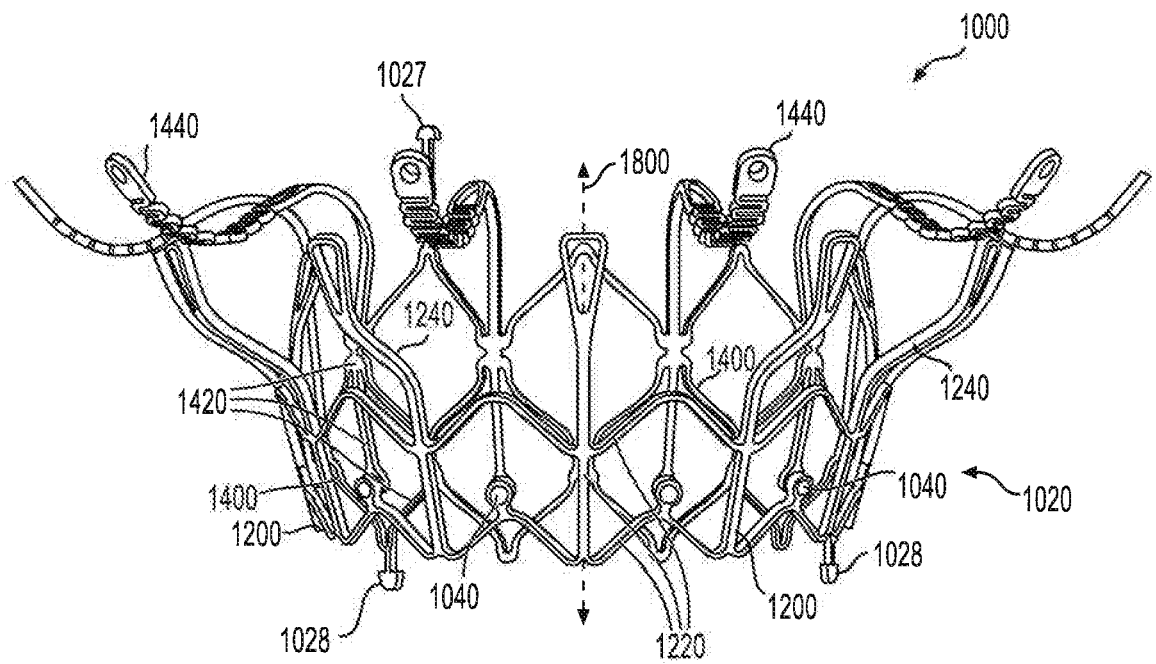
FIG. 1A illustrates a front elevation view of an exemplary frame for a prosthetic valve, consistent with various embodiments of the present disclosure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

In some embodiments of the present disclosure, an "atrial direction" may refer to a direction extending towards an atrium of the heart. For example, from a location within the left ventricle or the mitral valve, an atrial direction may refer to a direction extending towards the left atrium. Additionally, from a location within an atrium (e.g., the left atrium), an atrial direction may refer to a direction extending away from an adjacent atrioventricular valve (e.g., the mitral valve) and further into the atrium. For example, in FIGS. 10G and 10H, an atrial direction may refer to a direction extending upwards from prosthetic valve 6000 towards atrium 9010. In some exemplary embodiments, an atrial direction need not necessarily be parallel to a longitudinal axis of a prosthetic valve (e.g., longitudinal axis 2800 illustrated in FIG. 2A), so long as the direction is angled towards an atrium. The atrial direction may be parallel to a longitudinal axis of a prosthetic valve in some cases. In some embodiments, a "non-ventricular direction" may refer to a direction that does not extend towards a ventricle of the heart. A "non-ventricular direction" may extend in an atrial direction, or it may extend laterally in a direction perpendicular to a ventricular direction.

In some exemplary embodiments of the present disclosure, a "ventricular direction" may refer to a direction extending towards a ventricle of the heart. From a location within the left atrium or the mitral valve, a ventricular direction may refer to a direction extending towards the left ventricle. Additionally, from a location within a ventricle (e.g., the left ventricle), a ventricular direction may refer to a direction extending away from an adjacent atrioventricular valve (e.g., the mitral valve) and further into the ventricle. For example, in FIGS. 10G and 10H, a ventricular direction may refer to a direction extending downwards from prosthetic valve 6000 towards ventricle 9020. In some exemplary embodiments, a ventricular direction need not necessarily be parallel to a longitudinal axis of a prosthetic valve (e.g., longitudinal axis 2800 illustrated in FIG. 2A), so long as the direction is angled towards a ventricle. The ventricular direction may be parallel to a longitudinal axis of a prosthetic valve in some cases. In some embodiments, a "non-atrial direction" may refer to a direction that does not extend towards an atrium of the heart. A non-atrial direction may extend in a ventricular direction, or it may extend laterally in a direction perpendicular to an atrial direction.

Exemplary embodiments generally relate to prosthetic valves for implantation within a native valve and methods for implanting prosthetic valves within a native valve. In addition, exemplary embodiments generally relate to systems and methods for implantation of prosthetic valves by prosthetic valve delivery systems. While the present disclosure provides examples relating to prosthetic heart valves, and in particular prosthetic mitral valves, as well as delivery systems for prosthetic heart valves, it should be noted that aspects of the disclosure in their broadest sense are not limited to a prosthetic heart valve. Rather, the foregoing principles may be applied to other prosthetic valves as well. In various embodiments in accordance with the present disclosure, the term prosthetic valve refers generally to an implantable valve configured to restore and/or replace the functionality of a native valve, such as a diseased or otherwise impaired native heart valve.

An exemplary prosthetic valve may include a prosthetic valve configured to render a native valve structure nonfunctional, and may thus replace the function of the native valve. For example, an exemplary prosthetic valve may have a size and shape similar to the valve being replaced and may include a number of leaflet-like structures to regulate fluid flow and prevent backflow of blood through the valve. Additionally, or alternatively, an exemplary prosthetic valve may also include a prosthetic valve configured to leave the native valve structure intact and functional. An exemplary prosthetic valve may include a mitral valve, tricuspid valve, aortic valve, or pulmonary valve, as well as a valve outside of the heart, such as a venous valve, lymph node valve, ileocecal valve, or any other structure configured to control and/or regulate fluid flow in the body. An exemplary prosthetic valve may additionally or alternatively be configured to replace a failed bioprosthesis, such as a failed heart valve prosthesis.

Figure 1B:
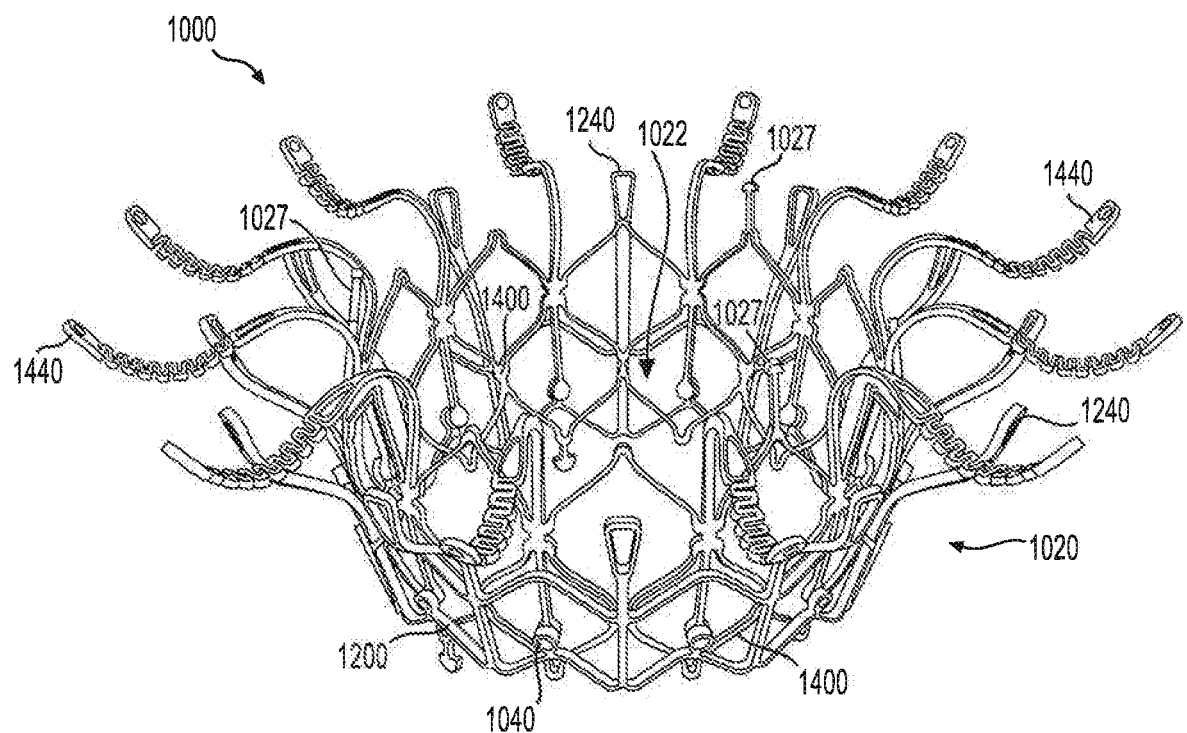
FIG. 1B illustrates a perspective view of the exemplary frame of FIG. 1A, consistent with various embodiments of the present disclosure.

FIG. 1A illustrates a front elevation view of an exemplary frame 1000 for a prosthetic valve. FIG. 1B illustrates a perspective view of frame 1000. Frame 1000 may be constructed of a shape memory material such as nickel titanium alloy (Nitinol) and may be configured to support other components of the prosthetic valve, such as prosthetic leaflets and protective cover layers. Frame 1000 may include an annular outer frame 1200 and an inner frame 1400 situated at least partially within the outer frame 1200. Annular outer frame 1200 and inner frame 1400 may be secured together by pins, screws, welding, soldering, adhesive, magnets, and/or any other suitable mechanism. For example, FIGS. 1A and 1B depict annular outer frame 1200 and inner frame 1400 connected by a plurality of connector pins 1040.

Annular outer frame 1200 may include an outer frame tubular portion 1220, which may be formed of a plurality of struts intersecting at junctions to form a wire mesh, stent-like, or cage-like structure of the outer frame tubular portion 1220. Annular outer frame 1200 may also include at least one ventricular anchoring leg 1240, which may be configured to extend radially outward from the outer frame tubular portion and which may contact, or otherwise engage, tissue within or near the native valve to anchor the prosthetic valve within the native valve. In some embodiments, exemplary valve frame 1000 may include twelve ventricular anchoring legs 1240, which may be configured to engage ventricular tissue of a native atrioventricular valve.

Inner frame 1400 may include an inner frame tubular portion 1420, which may be formed of a plurality of struts intersecting at junctions to form a wire mesh, stent-like, or cage-like structure of the inner frame tubular portion 1420. Inner frame 1400 may also include at least one atrial anchoring arm 1440, which may be configured to extend radially outward from the inner frame tubular portion and which may contact, or otherwise engage, tissue within or near the native valve to anchor the prosthetic valve within the native valve. In some embodiments, exemplary valve frame 1000 may include twelve atrial anchoring arms 1440, which may be configured to engage atrial tissue of a native atrioventricular valve.

Outer frame tubular portion 1220 and inner frame tubular portion 1420 may together form an annular valve body 1020 of the prosthetic valve, which may have at least one opening and from which the ventricular anchoring legs 1240 and atrial anchoring arms 1440 may extend. Annular valve body 1020 may include an axial lumen 1022 extending through the annular valve body 1020 along a longitudinal axis 1800 of the prosthetic valve. In some embodiments, annular valve body 1020 may be configured to receive a flow control device, such as one or more prosthetic leaflets, within axial lumen 1022. Optionally, annular valve body 1020 may include one or more atrial end delivery posts 1027 along an atrial end (i.e., top end) of the annular valve body and/or one or more ventricular end delivery posts 1028 along a ventricular end (i.e., bottom end) of the annular valve body. Delivery posts 1027 and 1028 may be configured to removably engage a delivery device of the prosthetic valve, for example, to assist with placement of frame 1000 within or near a native valve.

Figure 2A:
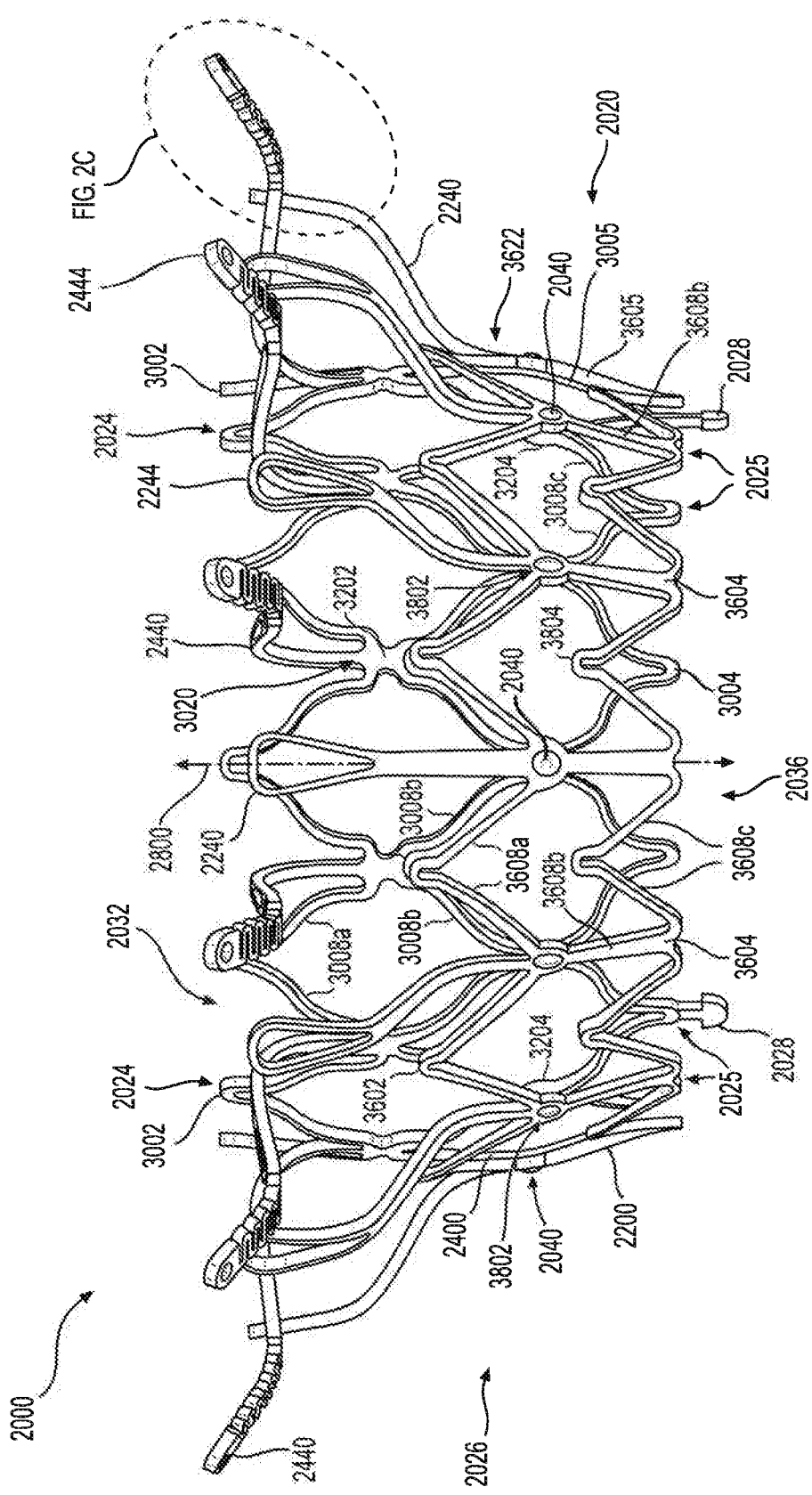
FIG. 2A illustrates a front elevation view of another exemplary frame for a prosthetic valve, consistent with various embodiments of the present disclosure.
Figure 2B:
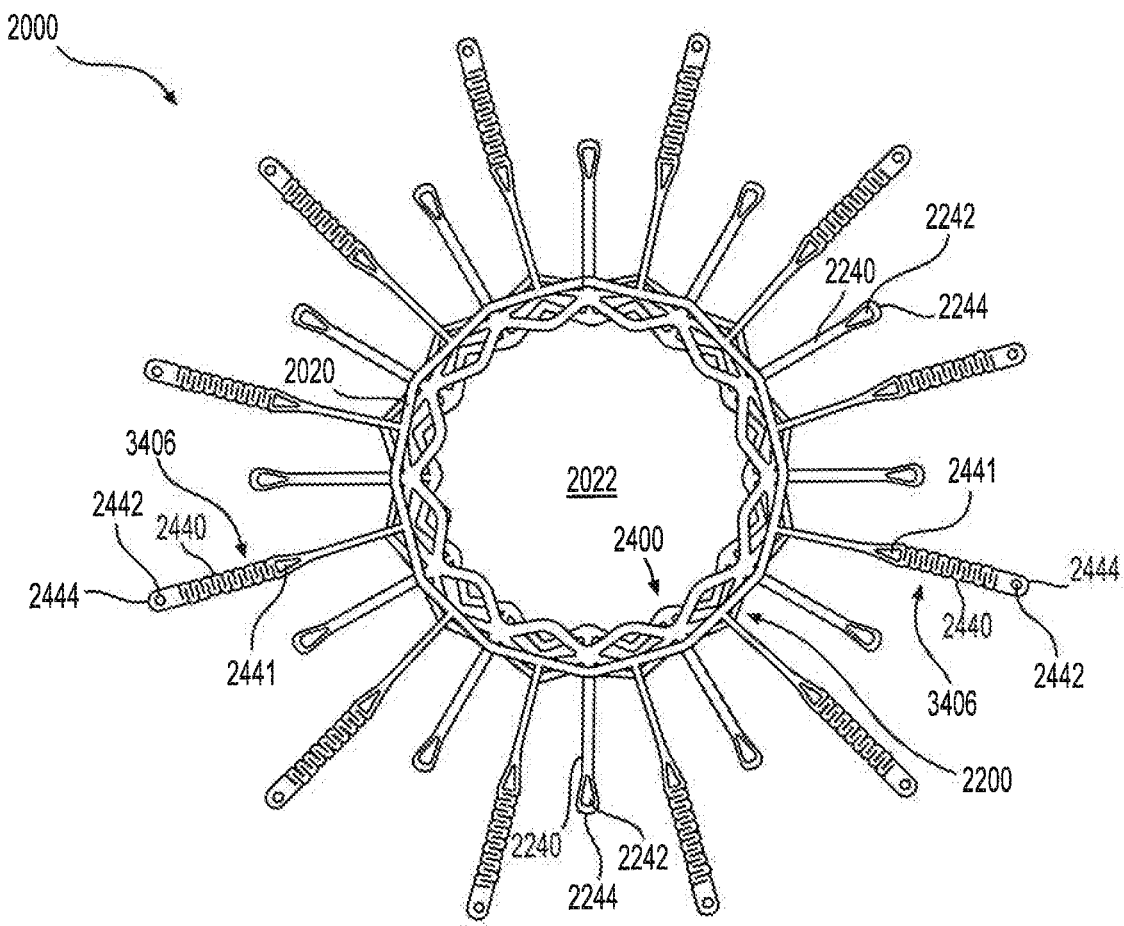
FIG. 2B illustrates a top plan view of the exemplary frame of FIG. 2A, consistent with various embodiments of the present disclosure.

FIG. 2A illustrates a front view of another exemplary frame 2000 for a prosthetic valve. FIG. 2B illustrates a top plan view of the frame 2000. Frame 2000 may include an annular outer frame 2200 and an inner frame 2400 situated at least partially within the annular outer frame 2200. Annular outer frame 2200 and inner frame 2400 may be secured together by pins, screws, welding, soldering, adhesive, magnets, and/or any other suitable mechanism. For example, FIGS. 2A and 2B depict annular outer frame 2200 and inner frame 2400 connected by a plurality of connector pins 2040.

Annular outer frame 2200 may include an outer frame tubular portion 3605, which may be formed of a plurality of struts intersecting at junctions to form a wire mesh, stent-like, or cage-like structure of the outer frame tubular portion 3605. For example, as illustrated in FIG. 2A, annular outer frame 2200 may include outer frame atrial circumferential struts 3608a, outer frame leg base struts 3608b, and outer frame ventricular circumferential struts 3608c intersecting at atrial end outer frame junctions 3602, leg attachment junctions 3802, outer frame junctions 3804, and ventricular end outer frame junctions 3604 to form outer frame tubular portion 3605. Annular outer frame 2200 may also include at least one ventricular anchoring leg 2240, which may extend from leg attachment junction 3802 of the outer frame tubular portion 3605 and which may be configured to engage ventricular tissue of a native valve to anchor the prosthetic valve in the native valve. The at least one ventricular anchoring leg 2240 may include a proximal leg end 3622, which may be the end of the leg connected to the outer frame tubular portion, and a distal leg end 2244, which may be situated radially outward from the outer frame tubular portion. As shown in FIG. 2B, the at least one ventricular anchoring leg 2240 may include at least one opening 2242.

Inner frame 2400 may include an inner frame tubular portion 3005, which may be formed of a plurality of struts intersecting at junctions to form a wire mesh, stent-like, or cage-like structure of the inner frame tubular portion 3005. For example, as illustrated in FIG. 2A, inner frame 2400 may include inner frame atrial struts 3008a, inner frame intermediate struts 3008b, and inner frame ventricular struts 3008c intersecting at atrial end inner frame junctions 3002, arm attachment junctions 3202, inner frame strut junctions 3204, and ventricular end inner frame junctions 3004 to form inner frame tubular portion 3005. Inner frame 2400 may also include at least one atrial anchoring arm 2440, which may extend from arm attachment junction 3202 of the inner frame tubular portion 3005 and which may be configured to engage atrial tissue of a native valve to anchor the prosthetic valve in the native valve. The at least one atrial anchoring arm 2440 may include a proximal arm end 3020, which may be the end of the arm connected to the inner frame tubular portion, and a distal arm end 2444, which may be situated radially outward from the inner frame tubular portion. As shown in FIG. 2B, the at least one atrial anchoring arm 2440 may include a proximal arm opening 2441 and a distal arm opening 2442.

Outer frame tubular portion 3605 and inner frame tubular portion 3005 may together form an annular valve body 2020 of the prosthetic valve, which may have at least one opening and from which the ventricular anchoring legs 2240 and atrial anchoring arms 2440 may extend. Annular valve body 2020 may include an axial lumen 2022 extending through the annular valve body 2020 along a longitudinal axis 2800 of the prosthetic valve. Annular valve body 2020 may have an atrial end 2024, a ventricular end 2025 opposite the atrial end, and an intermediate portion 2026 extending between the atrial and ventricular ends. In some embodiments, the atrial end may refer to the portion of the annular valve body configured to be situated at a location within the atrium that is furthest from an adjacent ventricle, when the prosthetic valve is implanted in a native valve. Similarly, the ventricular end may refer to the portion of the annular valve body configured to be situated at a location within the ventricle that is furthest from an adjacent atrim, when the prosthetic valve is implanted in a native valve. The intermediate portion 2026 may extend between the atrial end 2024 and ventricular end 2025. In some embodiments, annular valve body 2020 may include one or more ventricular end delivery posts 1028 along the ventricular end 2025 of the annular valve body. Axial lumen 2022 may include an inlet opening 2032 at the atrial end of the annular valve body, as well as an outlet opening 2036 at the ventricular end of the annular valve body.

Figure 2C:
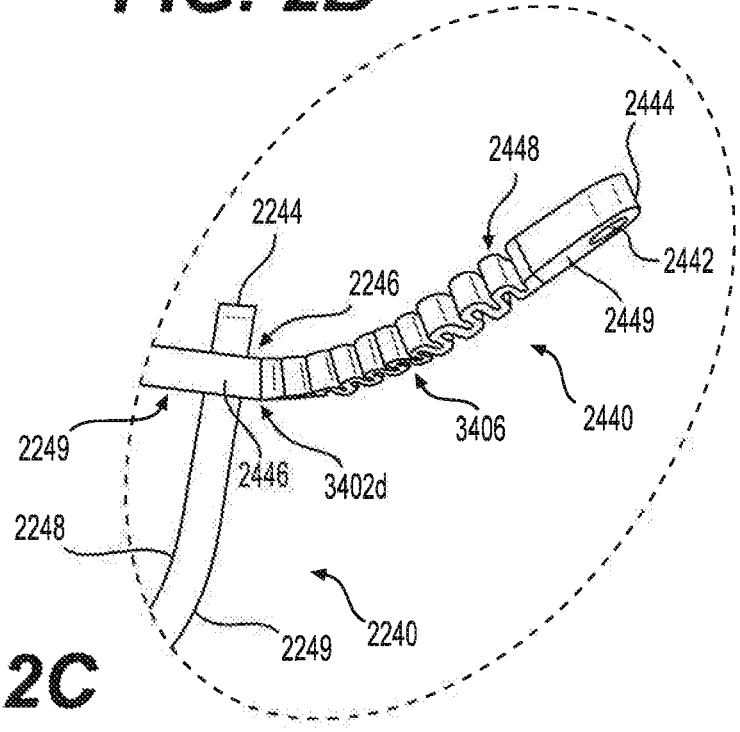
FIG. 2C illustrates an enlarged view of an atrial anchoring arm and a ventricular anchoring leg of the exemplary frame of FIG. 2A, consistent with various embodiments of the present disclosure.

FIG. 2C illustrates an enlarged view of an atrial anchoring arm 2440 and a ventricular anchoring leg 2240 of frame 2000. Ventricular anchoring leg 2240 may include an inner, atrially-facing leg surface 2248 and an outer, ventricularly-facing leg surface 2249. Atrial anchoring arm 2440 may include an atrially-facing arm surface 2448 and a ventricularly-facing arm surface 2449. In some embodiments, atrial anchoring arm 2440 may include an arm portion 2446 configured to be arranged in a common lateral plane with leg portion 2246 of the ventricular anchoring leg 2240. That is, leg portion 2246 and arm portion 2446 may be positioned at the same axial position along longitudinal axis 2800.

Figure 2D:
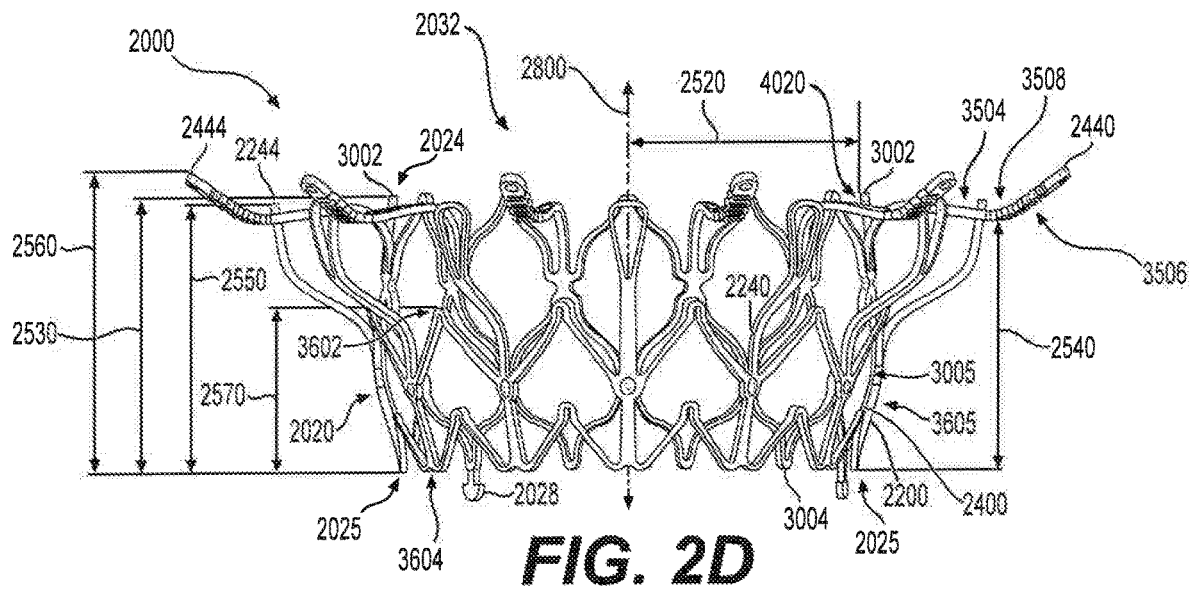
FIG. 2D illustrates another front elevation view of the exemplary frame of FIG. 2A, consistent with various embodiments of the present disclosure.

FIG. 2D illustrates another front elevation view of frame 2000. The exemplary prosthetic valve, as well as frame 2000, may have an axial height 2560, which may extend between terminal arm ends 2444 and ventricular end 2025 of the annular valve body. Inner frame tubular portion 3005 may have an axial height 2530, which may extend between atrial end inner frame junctions 3002 and ventricular end inner frame junctions 3004. Annular outer frame 2200 may have an axial height 2550, which may extend between terminal leg ends 2244 and ventricular end 2025 of the annular valve body. Outer frame tubular portion 3605 may have an axial height 2570, which may extend between atrial end outer frame junctions 3602 and ventricular end outer frame junctions 3604. In some embodiments, frame 2000 may have a ventricular device protrusion distance 2540, which may represent the distance over which the prosthetic valve protrudes into a left ventricle when the prosthetic valve is implanted in a native mitral valve. Annular valve body 2020 may include a valve inlet radius 2520, which may be the radius of atrial inlet opening 2032.

Figure 2E:
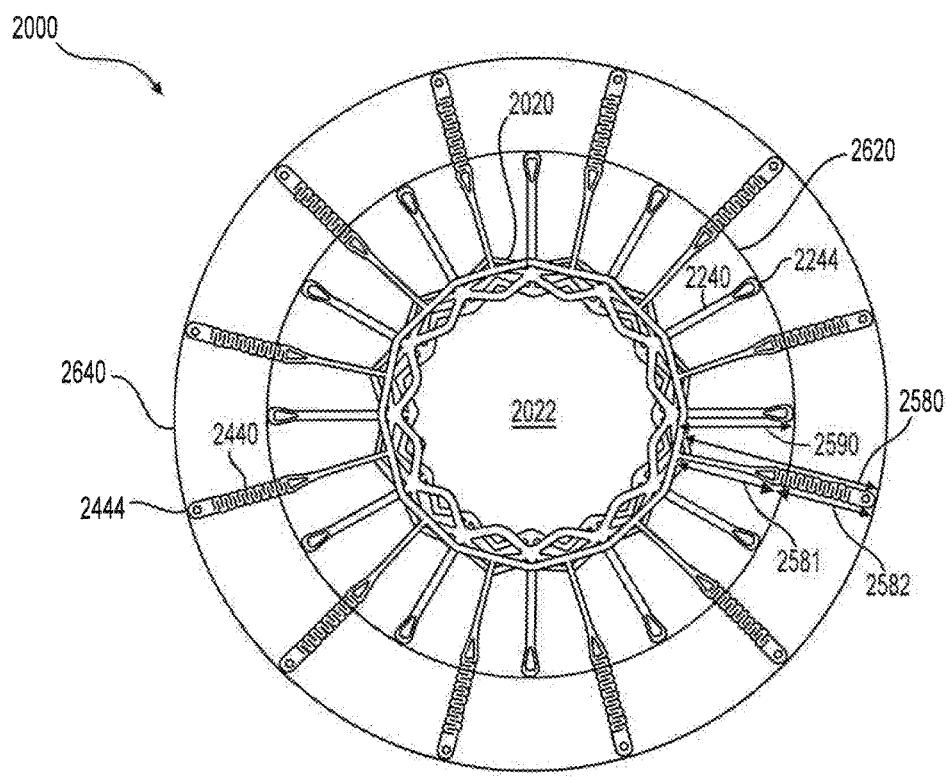
FIG. 2E illustrates another top plan view of the exemplary frame of FIG. 2A, consistent with various embodiments of the present disclosure.

FIG. 2E illustrates another top plan view of frame 2000. The atrial anchoring arms 2440 may have a length 2580, and the ventricular anchoring legs 2240 may have a length 2590. The terminal arm ends 2444 may define an atrial anchoring arm circumference 2640. The terminal leg ends 2244 may define a ventricular anchoring leg circumference 2620, which may be concentric with atrial anchoring arm circumference 2640. Inflexible portions 3402 of the atrial anchoring arms (illustrated in FIG. 3B) may have a length 2581. Serpentine structures 3406 of the atrial anchoring arms (illustrated in FIG. 3B) may have a length 2582.

Figure 3A:
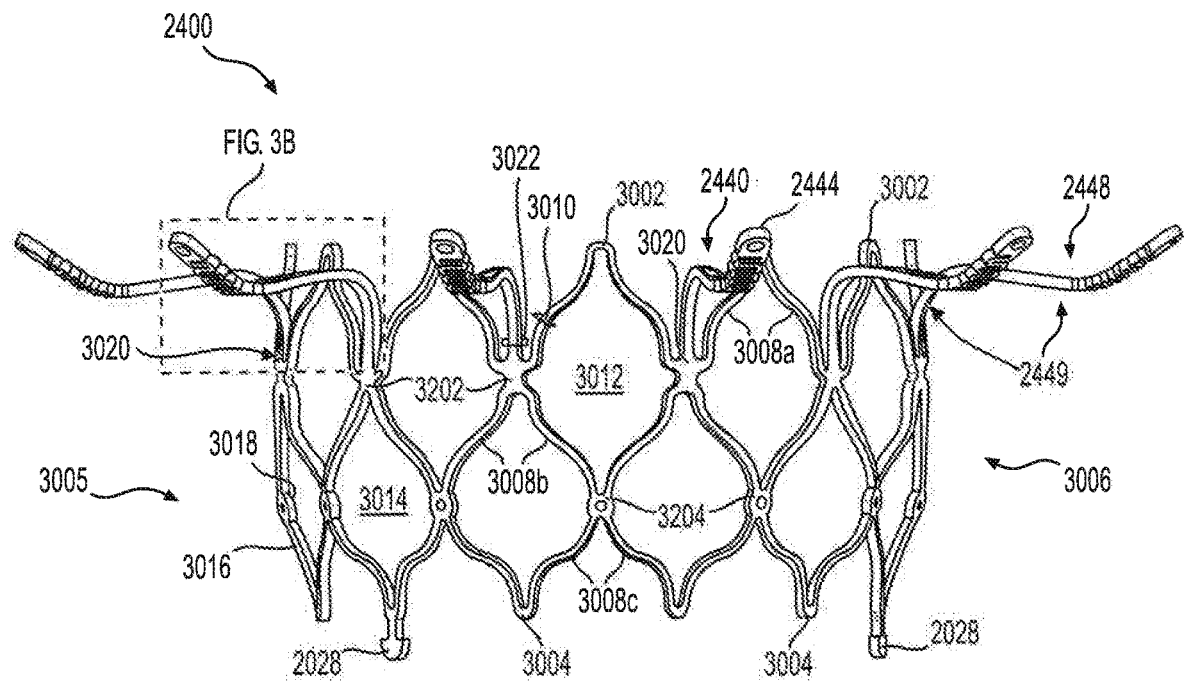
FIG. 3A illustrates a front elevation view of an inner frame of the exemplary frame of FIG. 2A, consistent with various embodiments of the present disclosure.

FIG. 3A illustrates a front elevation view of inner frame 2400. The atrial end inner frame junctions 3002 and ventricular end inner frame junctions 3004 may form the atrial end and ventricular end, respectively, of inner frame 2400. Inner frame intermediate portion 3006 may extend between atrial end inner frame junctions 3002 and ventricular end inner frame junctions 3004. Inner frame tubular portion 3005 may have a radially inner surface 3018 and a radially outer surface 3016. Inner frame atrial struts 3008a and inner frame intermediate struts 3008b may intersect at atrial end inner frame junctions 3002, arm attachment junctions 3202, and strut junctions 3204 to form a first, atrial row of closed cells 3012. Inner frame intermediate struts 3008b and inner frame ventricular struts 3008c may intersect at arm attachment junctions 3202, strut junctions 3204, and ventricular end inner frame junctions 3004 to form a second, ventricular row of closed cells 3014. At least one inner frame atrial strut 3008a may have a cross-sectional area 3010. At least one atrial anchoring arm 2440 may have a cross-sectional area 3022.

Figure 3B:
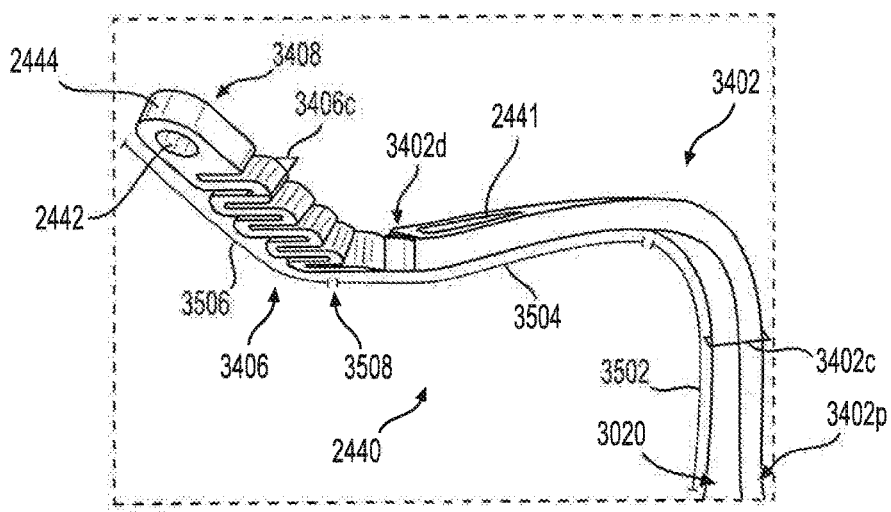
FIG. 3B illustrates an enlarged view of an atrial anchoring arm of the exemplary inner frame of FIG. 3A, consistent with various embodiments of the present disclosure.

FIG. 3B illustrates an enlarged view of an atrial anchoring arm 2440 of inner frame 2400. Atrial anchoring arm 2440 may include a proximal arm portion 3502 configured to extend in an atrial direction, intermediate arm portion 3504 configured to extend in a ventricular direction, and distal arm portion 3506 configured to extend in an atrial direction. Arm transition portion 3508 may represent the transition between intermediate arm portion 3504 and distal arm portion 3506. Atrial anchoring arm 2440 may also include an inflexible portion 3402 extending to proximal arm end 3020, as well as a serpentine structure 3406, which may be situated radially external to the inflexible portion 3402. Inflexible portion 3402 may have a proximal end 3402p, a distal end 3402d, and a cross-sectional area 3402c. Serpentine structure 3406 may have a cross-sectional area 3406c. In some embodiments, atrial anchoring arm 2440 may include a terminal arm region 3408 situated radially external to serpentine structure 3406. Distal arm opening 2442 may be situated within terminal arm region 3408.

Figure 3C:
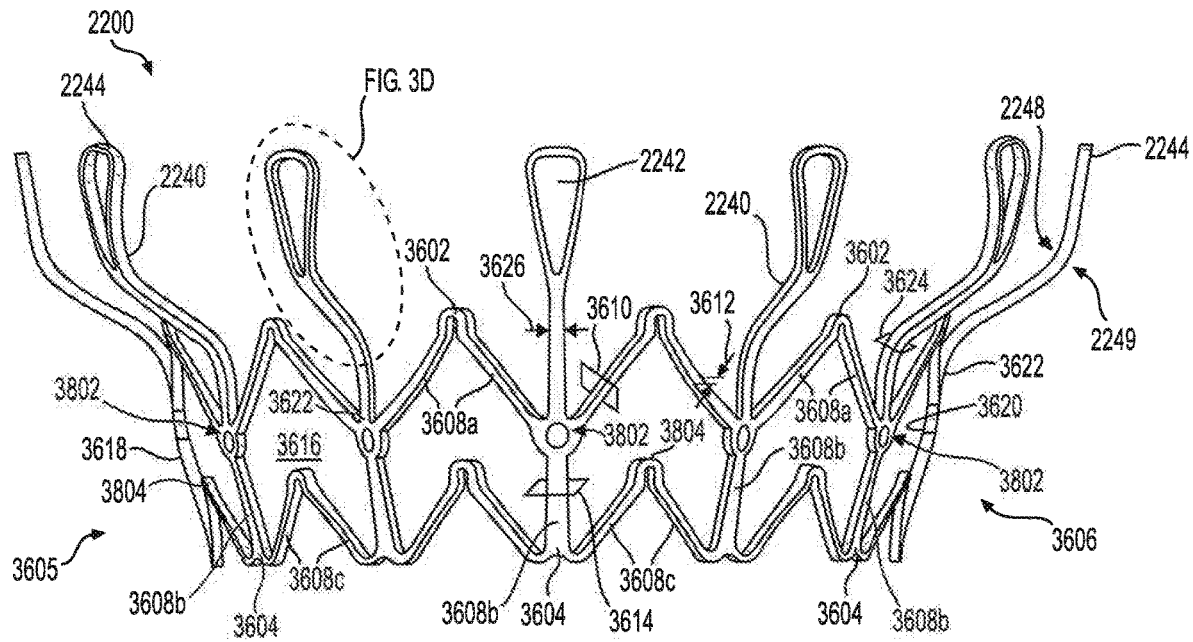
FIG. 3C illustrates a front elevation view of an outer frame of the exemplary frame of FIG. 2A, consistent with various embodiments of the present disclosure.

FIG. 3C illustrates a front elevation view of outer frame 2200. The atrial end outer frame junctions 3602 and ventricular end outer frame junctions 3604 may form the atrial end and ventricular end, respectively, of annular outer frame 2200. Outer frame intermediate portion 3606 may extend between atrial end outer frame junctions 3602 and ventricular end outer frame junctions 3604. Outer frame tubular portion 3605 may have a radially outer surface 3618 and a radially inner surface 3620. The outer frame atrial circumferential struts 3608a, outer frame leg base struts 3608b, and outer frame ventricular circumferential struts 3608c may intersect at the atrial end outer frame junctions 3602, leg attachment junctions 3802, outer frame junctions 3804, and ventricular end outer frame junctions 3604 to form closed cells 3616. At least one outer frame atrial circumferential strut 3608a may have a cross-sectional area 3610 and a width 3612. At least one outer frame leg base strut 3608b may have a cross-sectional area 3614. At least one ventricular anchoring leg may have a cross-sectional area 3624 and a radially outer surface width 3626.

Figure 3D:
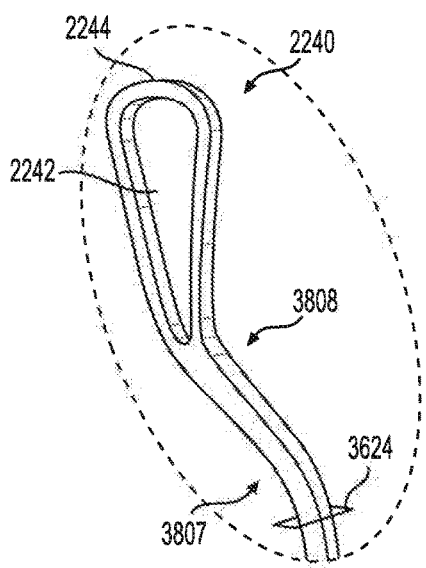
FIG. 3D illustrates an enlarged view of a ventricular anchoring leg of the exemplary outer frame of FIG. 3C, consistent with various embodiments of the present disclosure.

FIG. 3D illustrates an enlarged view of a portion of a ventricular anchoring leg 2240 of annular outer frame 2200. Ventricular anchoring leg 2240 may include a first, proximal curved portion 3807 and a second, distal curved portion 3808. In some embodiments, proximal curved portion 3807 may face radially outward. Additionally, or alternatively, distal curved portion 3808 may face radially inwards.

Figure 4B:
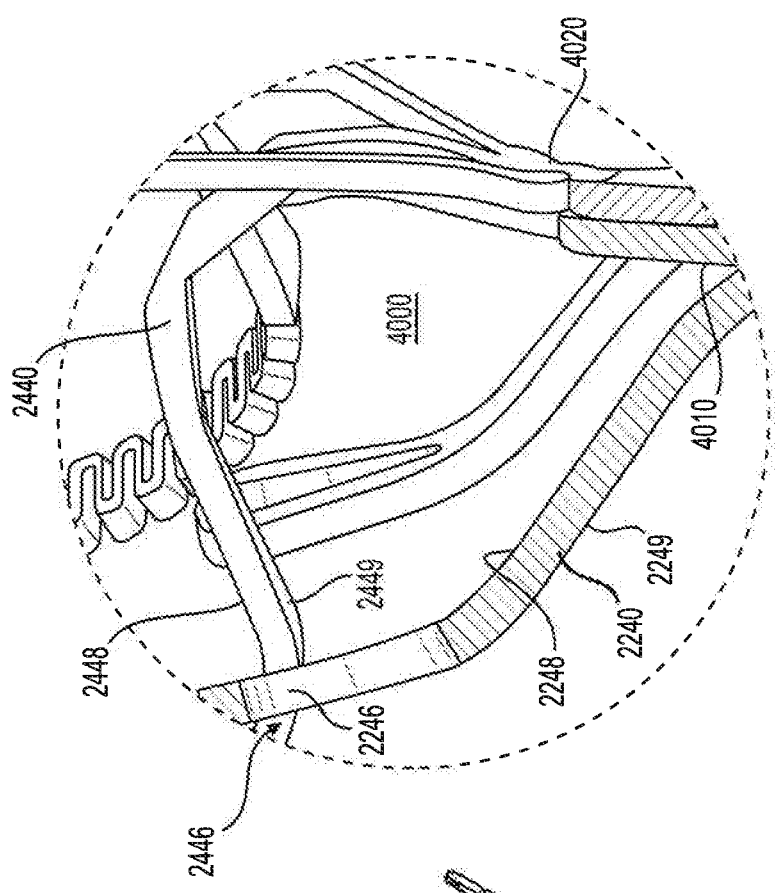
FIG. 4B illustrates an enlarged view of a volume between an atrial anchoring arm and a ventricular anchoring leg of the exemplary frame of FIG. 4A, consistent with various embodiments of the present disclosure.
Figure 4A:
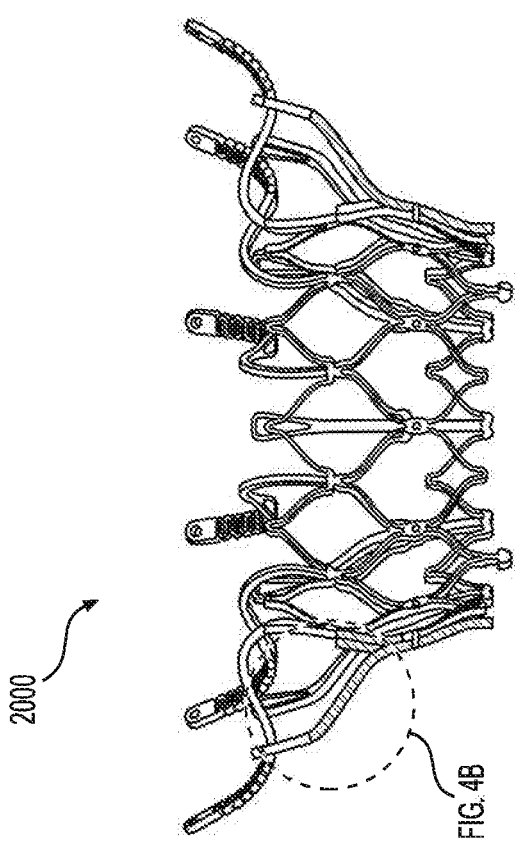
FIG. 4A illustrates a cross-sectional view of the exemplary frame of FIG. 2A, consistent with various embodiments of the present disclosure.

FIG. 4A illustrates a cross-sectional view of frame 2000, and FIG. 4B illustrates an enlarged view of a portion of FIG. 4A depicting a volume 4000 formed between the atrial anchoring arms 2440 and ventricular anchoring legs 2240. FIG. 4B also depicts an outer surface 4010 and inner surface 4020 of annular valve body 2020. In some embodiments, volume 4000 may be bounded by the ventricularly-facing surfaces 2449 of atrial anchoring arms 2440, by the inner, atrially-facing surfaces 2248 of ventricular anchoring legs 2240, and by the outer surface 4010 of the annular valve body 2020.

FIG. 5A illustrates a configuration of the exemplary prosthetic valve in which annular valve body 2020, atrial anchoring arms 2440, and ventricular anchoring legs 2240 are arranged in a radially-contracted configuration. In some embodiments, the configuration illustrated in FIG. 5A may constitute a radially-contracted configuration of the prosthetic valve.

FIG. 5B illustrates a configuration of the exemplary prosthetic valve in which annular valve body 2020 and atrial anchoring arms 2440 are arranged in a radially-contracted configuration. In the configuration of FIG. 5B, the ventricular anchoring legs 2240 may deflect radially outward away from annular valve body 2020, into a radially-expanded configuration of the ventricular anchoring legs 2240.

FIG. 5C illustrates a configuration of the exemplary prosthetic valve in which annular valve body 2020 and ventricular anchoring legs 2240 are arranged in a radially-contracted configuration. In the configuration of FIG. 5C, the atrial anchoring arms 2440 may deflect radially outward away from annular valve body 2020, into a radially-expanded configuration of the atrial anchoring arms 2440.

FIG. 5D illustrates a configuration of the exemplary prosthetic valve in which the atrial anchoring arms 2440 and ventricular anchoring legs 2240 may deflect radially outward away from annular valve body 2020 into their respective radially-expanded configurations, while annular valve body 2020 remains in a radially-contracted configuration. In the configuration of FIG. 5D, an axial distance 5004 may be formed between the atrial anchoring arms 2440 and the terminal ends 2244 of the ventricular anchoring legs 2240.

FIG. 5E illustrates a configuration of the exemplary prosthetic valve in which annular valve body 2020, atrial anchoring arms 2440, and ventricular anchoring legs 2240 are arranged in a radially-expanded configuration. In some embodiments, the configuration illustrated in FIG. 5E may constitute a radially-expanded configuration of the prosthetic valve.

Figure 6A:
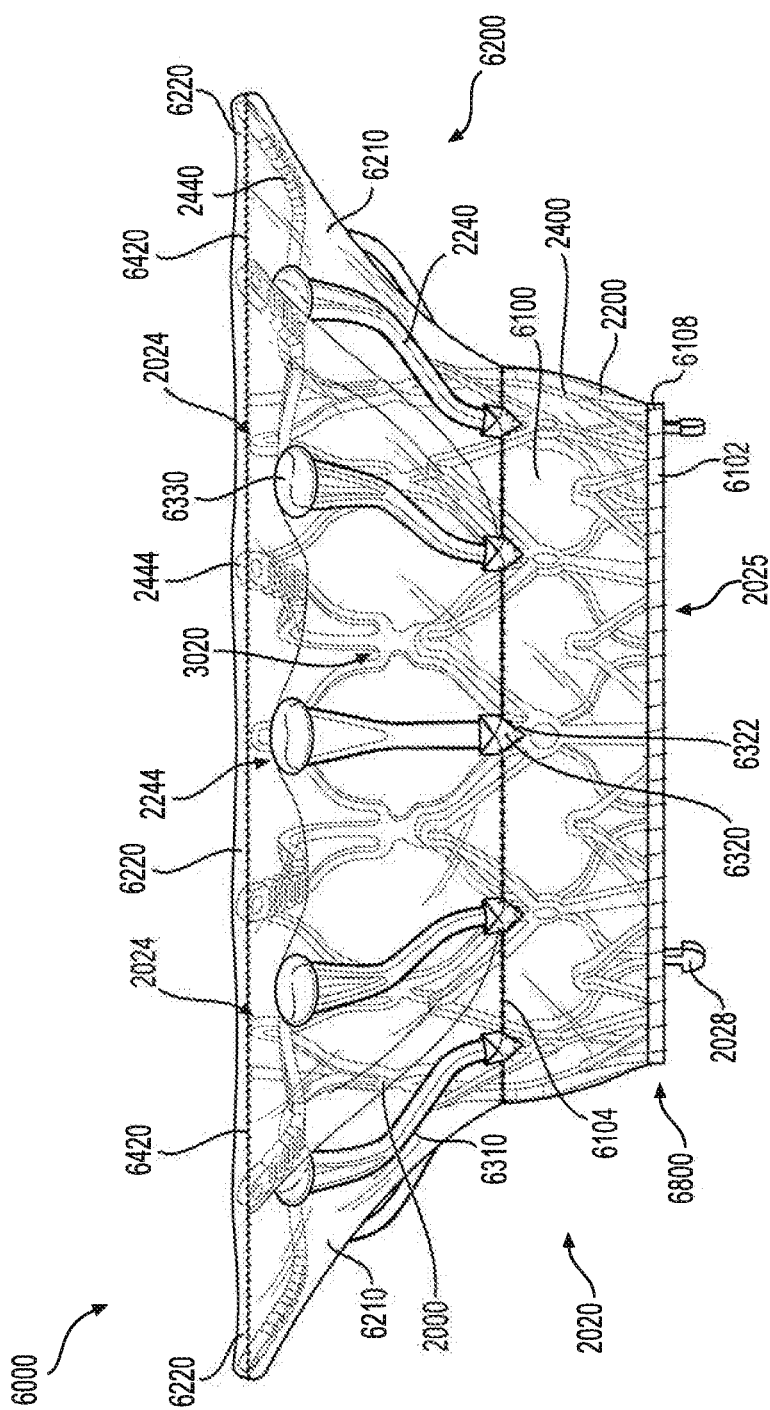
FIG. 6A illustrates a front elevation view of an exemplary prosthetic valve, consistent with various embodiments of the present disclosure.

FIG. 6A illustrates a front elevation view of prosthetic valve 6000. In some embodiments, prosthetic valve 6000 may be assembled upon frame 2000. Prosthetic valve 6000 may be configured for implantation within or near a native valve structure and may be configured to restore and/or replace the functionality of a native valve, such as a diseased or otherwise impaired native valve. Prosthetic valve 6000 may include valve frame 2000, including annular valve body 2020, the atrial anchoring arms 2440, and the ventricular anchoring legs 2240. Prosthetic valve 6000 may also include a skirt layer 6100 configured around an external surface of a portion of the annular valve body. Prosthetic valve 6000 may additionally include a first cuff sheet 6210, which may be connected to skirt layer 6100 via stitching 6104, as well as a second cuff sheet 6220, which may be connected to first cuff sheet 6210 via stitching 6420. In some embodiments, the first cuff sheet 6210 and second cuff sheet 6220 by extend around the terminal ends 2444 of the atrial anchoring arms 2440. Skirt layer 6100, first cuff sheet 6210, and second cuff sheet 6220 may be constructed of fluid-impermeable material and may accordingly be configured to prevent passage of blood or other fluids through portions of the prosthetic valve 6000 outside of the axial lumen 2022.

In some embodiments, prosthetic valve 6000 may additionally include a protective sleeve 6102 wrapped around the rim 6800 of the ventricular outlet opening of annular valve body 2020; protective sleeve 6102 may be secured to annular valve body 2020 by stitching 6108. Additionally, or alternatively, prosthetic valve 6000 may include at least one liner 6310 extending around an external surface of the ventricular anchoring legs 2240, with at least one protective layer 6330 positioned around the distal leg ends 2244 and at least one protective covering 6320 wrapped around the proximal leg ends 3622. In some embodiments, the at least one protective covering 6320 may be secured to the skirt layer 6100 via stitching 6322.

Figure 6B:
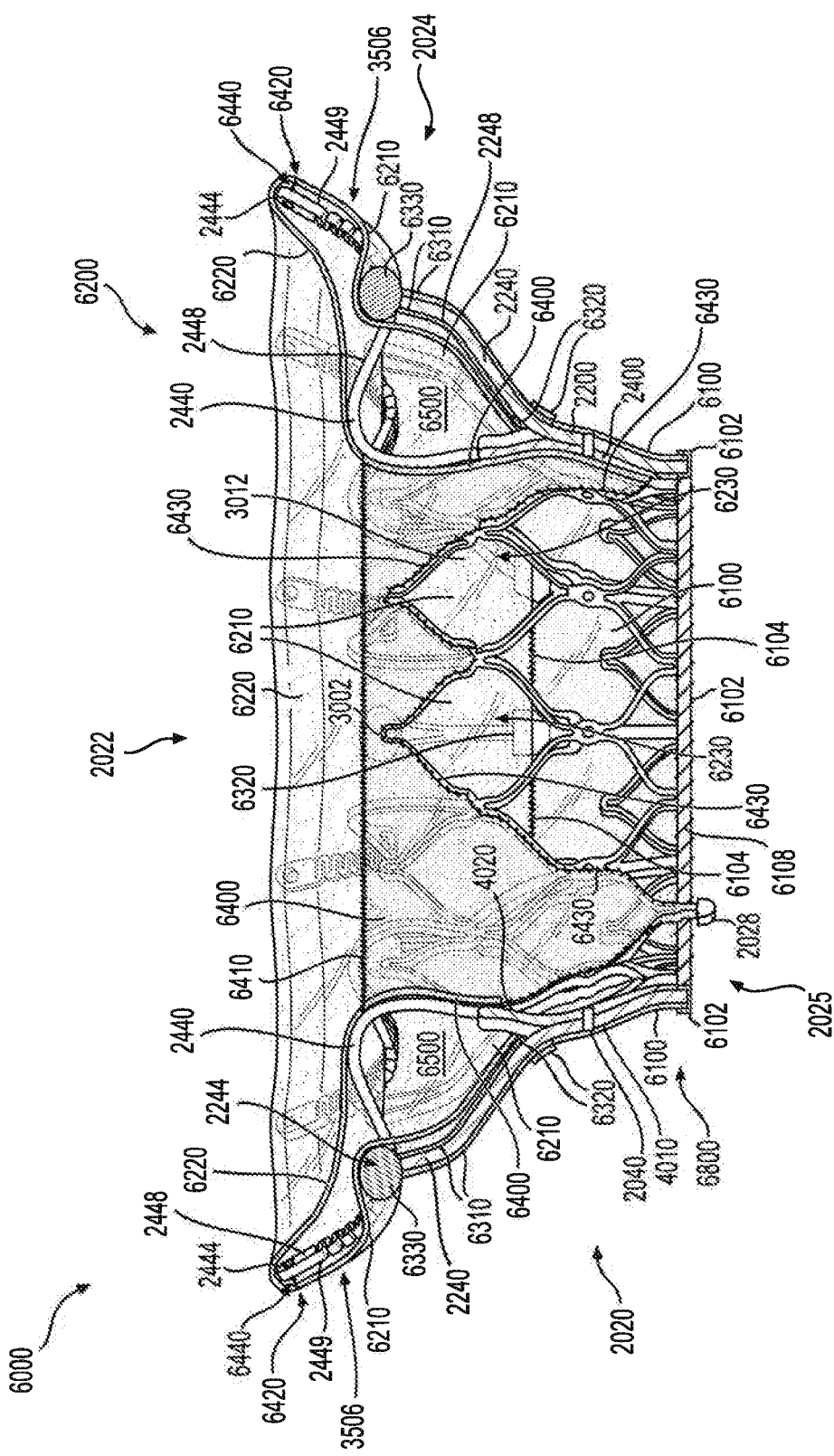
FIG. 6B illustrates a cross-sectional view of the exemplary prosthetic valve of FIG. 6A without leaflets, consistent with various embodiments of the present disclosure.

FIG. 6B illustrates a cross-sectional view of prosthetic valve 6000, without prosthetic leaflets situated within the axial lumen 2022. As illustrated in FIG. 6B, prosthetic valve 6000 may additionally include a liner 6400 covering at least a portion of the inner surface 4020 of the annular valve body 2020. Liner 6400 may be secured to the annular valve body 2020 via stitching 6430 and to the second cuff sheet 6220 via stitching 6410. First cuff sheet 6210, second cuff sheet 6220, and inner liner 6400 may together form an inflatable cuff 6200 having an interior volume 6500. In some embodiments, inflatable cuff 6200 may be secured to atrial anchoring arm 2440 via connector 6440. Blood may enter the cuff 6200 through openings 6230, causing the cuff 6200 to inflate radially outwards and axially in an atrial direction. In some embodiments, cuff 6200 may inflate radially outwards and press against tissue of the native valve. This engagement between the cuff and tissue of the native valve may form a barrier to flow of blood and other fluids around the outer circumference of the prosthetic valve 6000.

Figure 6C:
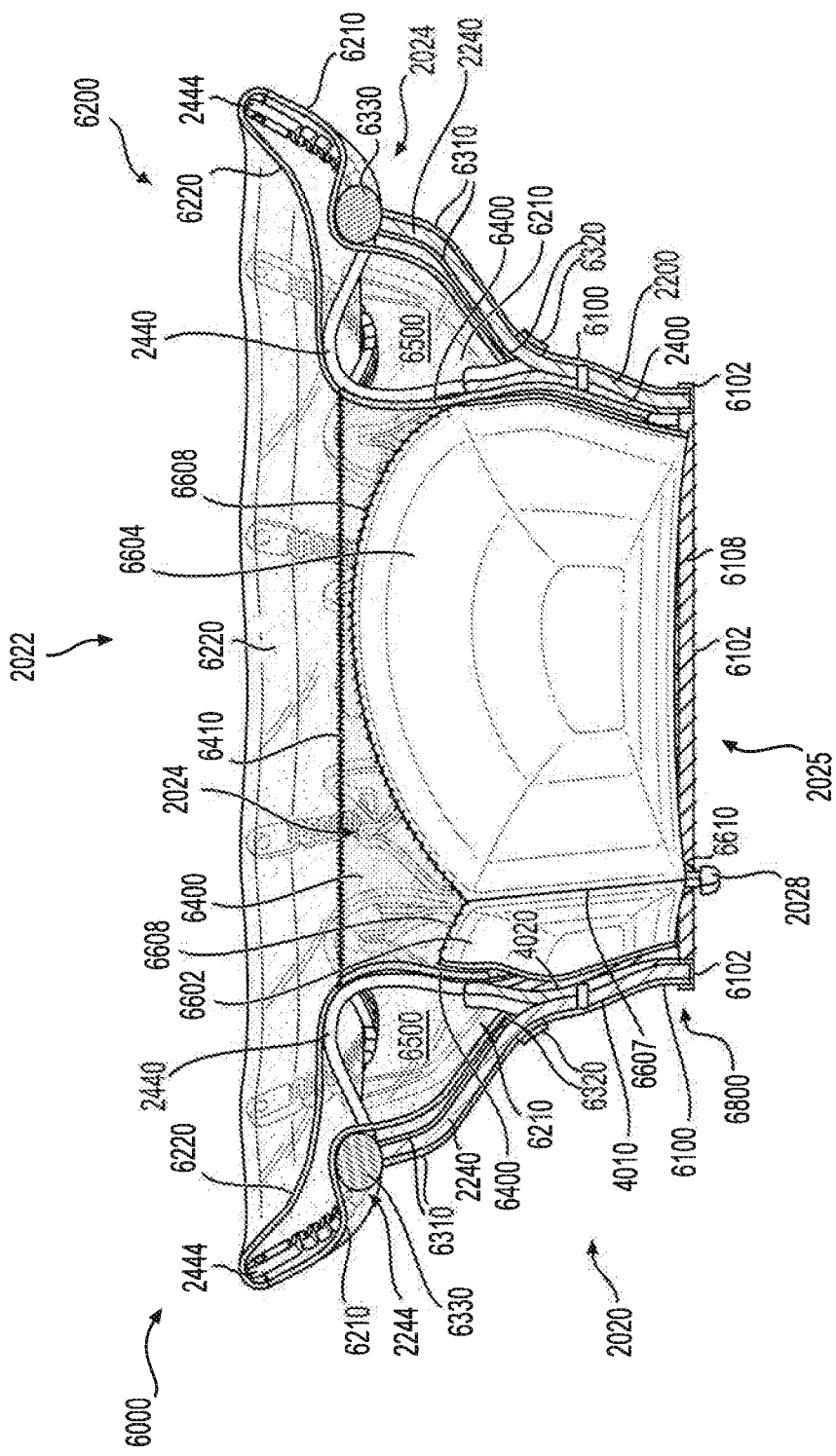
FIG. 6C illustrates a cross-sectional view of the exemplary prosthetic valve of FIG. 6A with leaflets, consistent with various embodiments of the present disclosure.

FIG. 6C illustrates a cross-sectional view of prosthetic valve 6000 with prosthetic leaflets 6602 and 6604 situated within the axial lumen 2022. In some embodiments, prosthetic valve 6000 may also include a third prosthetic leaflet 6606, which may not be visible in the view of FIG. 6C. The leaflets 6602, 6604, and 6606 may be secured to inner liner 6400 via stitching 6608 and may include a connector 6610 wrapping around the ventricular end delivery posts 2028 to secure the leaflets 6602, 6604, and 6606 to the valve frame 2000.

Figure 6D:
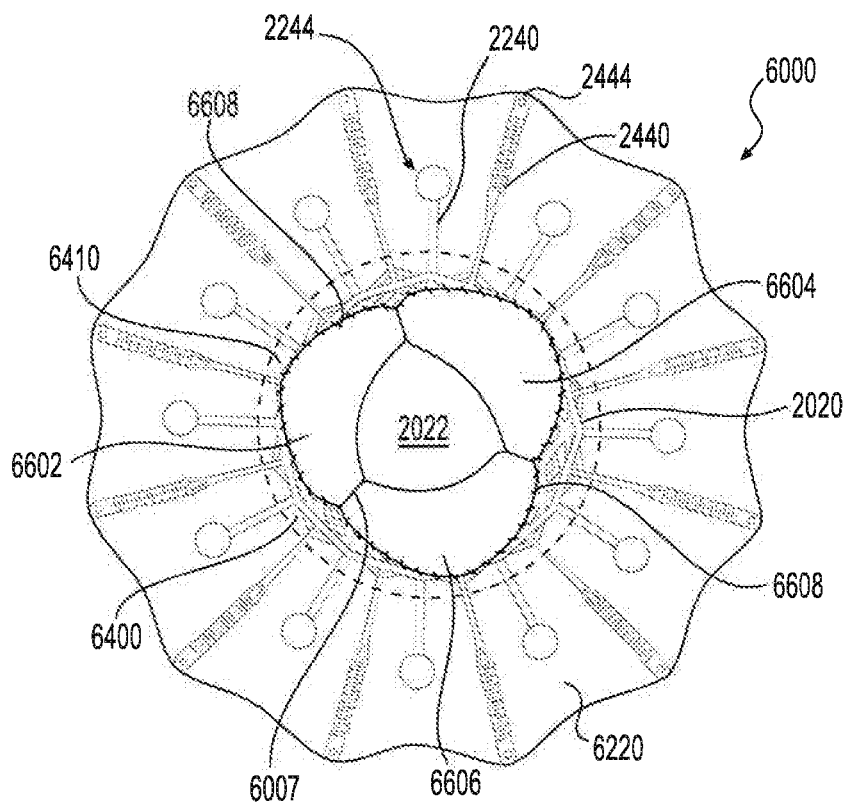
FIG. 6D illustrates a top plan view of the exemplary prosthetic valve of FIG. 6A with uninflated leaflets, consistent with various embodiments of the present disclosure.
Figure 6E:
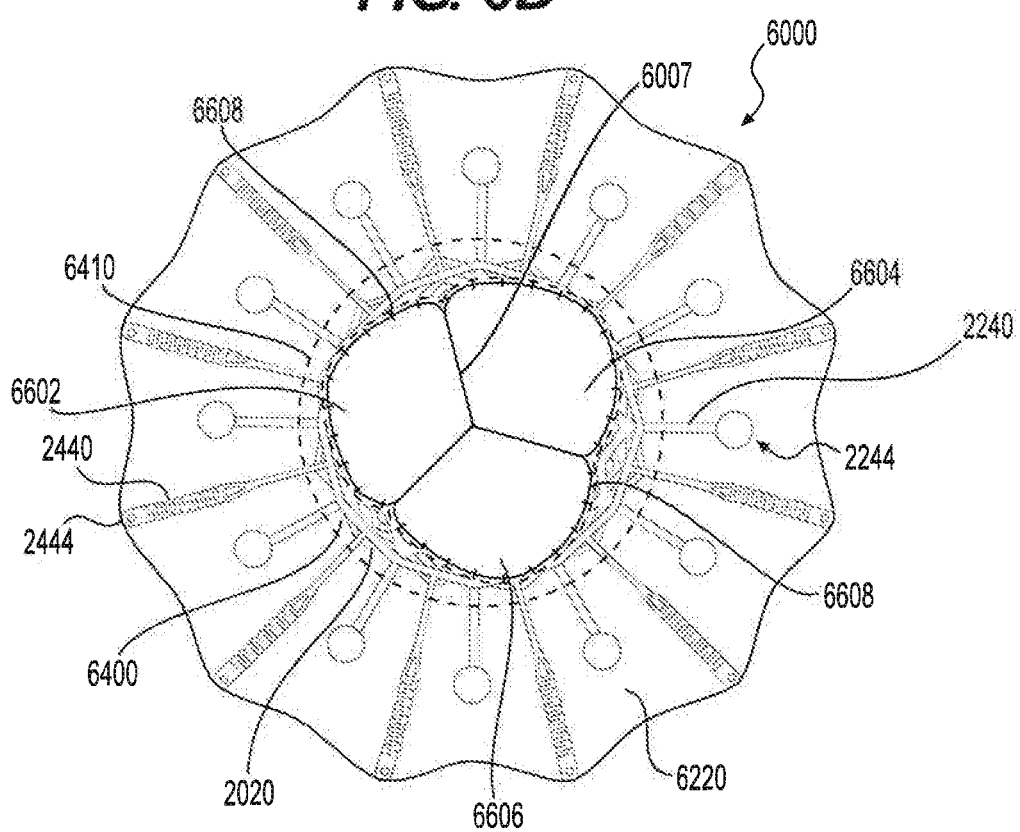
FIG. 6E illustrates a top plan view of the exemplary prosthetic valve of FIG. 6A with inflated leaflets, consistent with various embodiments of the present disclosure.

FIG. 6D illustrates a top plan view of prosthetic valve 6000, with leaflets 6602, 6604, and 6606 arranged in an open, uninflated configuration. In the open configuration, a space may be formed in the middle of the leaflets, permitting fluid to pass through the axial lumen 2022 of the prosthetic valve 6000. FIG. 6E illustrates a top plan view of prosthetic valve 6000, with leaflets 6602, 6604, and 6606 arranged in a closed, coapted configuration. In the closed configuration, the leaflets may press together such that the opening between them is closed. For example, the point of contact 6007 between two adjacent leaflets may extend to the center of the axial lumen; as a result, the leaflets may block fluid passage through the axial lumen 2022 of the prosthetic valve 6000.

Figure 7A:
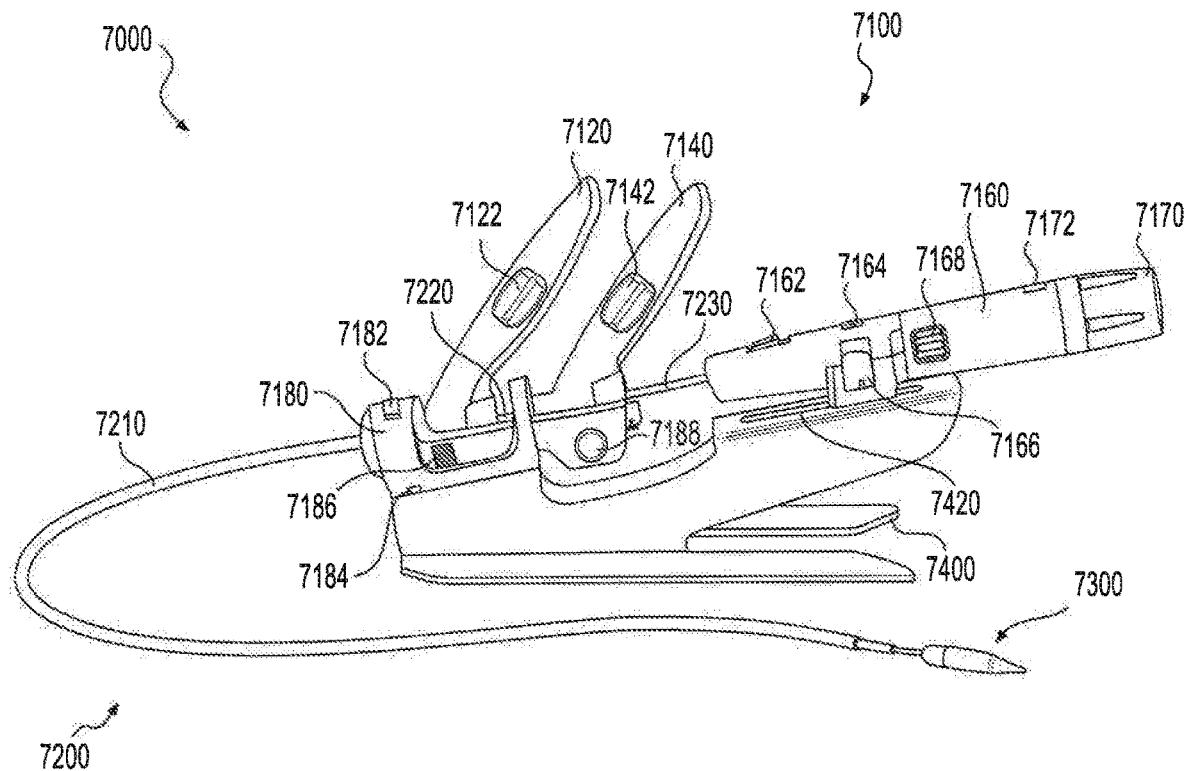
FIG. 7A illustrates an exemplary prosthetic valve delivery system, consistent with various embodiments of the present disclosure.

FIG. 7A illustrates a prosthetic valve delivery system 7000. Delivery system 7000 may be configured to deliver an implant prosthetic valve 6000 within a native valve, such as a native mitral valve. Prosthetic valve delivery system 7000 may include a control handle assembly 7100, a telescoping catheter assembly 7200, a delivery capsule 7300 configured to retain a prosthetic valve (e.g. valve 6000), and, optionally, a stand 7400.

Control handle assembly 7100 may include an outer sheath control handle 7120 having a steering knob 7122 configured to steer an outer sheath 7210 of the telescoping catheter assembly 7200. Control handle assembly 7100 may also include a guide catheter control handle 7140 having a steering knob 7142 configured to steer a guide catheter 7220 of the telescoping catheter assembly 7200.

Control handle assembly 7100 may also include an implant catheter control handle 7160 having a steering knob 7168 configured to steer an implant catheter 8100 of the telescoping catheter assembly 7200. Implant catheter control handle 7160 may also include a proximal capsule portion slider 7162, a distal capsule portion knob 7170, and a distal capsule portion knob lock 7172 configured to control release of the prosthetic valve 6000 from within delivery capsule 7300. Implant catheter control handle 7160 may also include a slide lock 7166 configured to lock the implant catheter control handle 7160 at a position within track 7420 of stand 7400.

Control handle assembly 7100 may also include a cradle 7180, which may be secured to stand 7400 via a locking mechanism that can be released by actuated of release button 7184. Cradle 7180 may include a rotation knob 7182 configured to control rotation of the outer sheath 7210 and guide catheter 7220. Cradle 7180 may also include a rotation knob 7186 configured to control rotation of the implant catheter 8100. Cradle 7180 may also include a knob 7188 configured to control relative axial movement between outer sheath control handle 7120 (which may be secured to outer sheath 7210) and guide catheter control handle 7140 (which may be secured to guide catheter 7220).

Figure 7B:
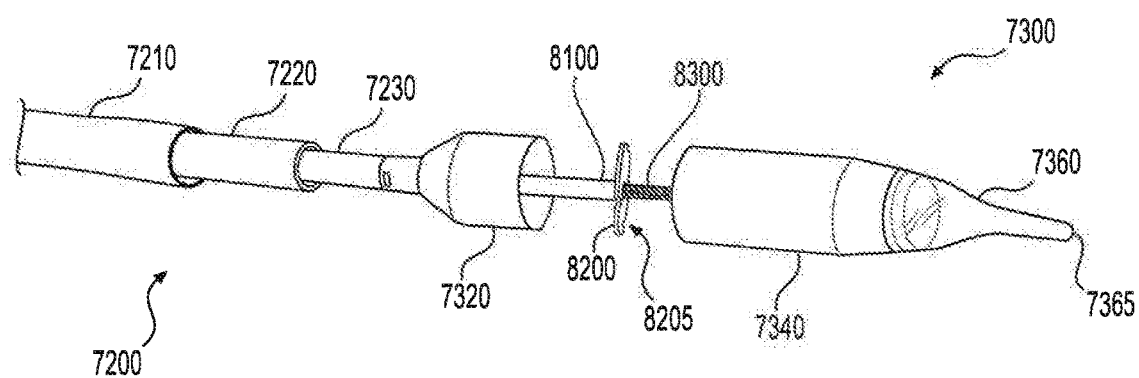
FIG. 7B illustrates an enlarged view of a delivery capsule of the exemplary prosthetic valve delivery system of FIG. 7A, consistent with various embodiments of the present disclosure.

FIG. 7B illustrates an enlarged view of delivery capsule 7300 of prosthetic valve delivery system 7000. Delivery capsule 7300 may include a proximal capsule portion 7320 and a distal capsule portion 7340 with a nose cone 7360 secured to the distal capsule portion 7340. A nose cone distal tip 7365 may form the distal end of the delivery capsule 7300. The telescoping catheter assembly 7200 may include a capsule shaft 7230 secured to, and configured to control movement of, the proximal capsule portion 7320 (e.g., due to connection 8400 between the capsule shaft 7230 and proximal capsule portion 7320, as illustrated in FIG. 8C). Implant catheter 8100 may extend within proximal capsule portion 7320 and may have a valve anchor disc 8200 connected to the distal end of the implant catheter 8100. A torque shaft 8300 may extend from the implant catheter 8100 and may be connected to distal capsule portion 7340; accordingly, torque shaft 8300 may be configured to control axial movement of the distal capsule portion 7340 relative to the implant catheter 8100 and valve anchor disc 8200. The proximal capsule portion 7320 and a distal capsule portion 7340 may be configured to retain prosthetic valve 6000, with the prosthetic valve 6000 secured against axial movement by valve anchor disc 8200. Control handle assembly 7100 may be configured to control movement of the proximal capsule portion 7320 and a distal capsule portion 7340, and thus may also control release of the prosthetic valve 6000 from within the delivery capsule 7300.

Figure 7D:
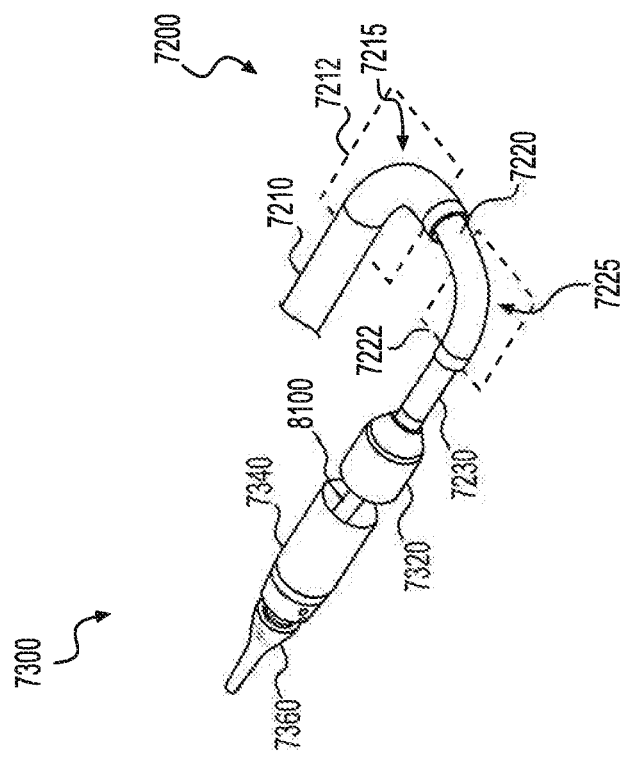
FIG. 7D illustrates another exemplary configuration of the telescoping catheter assembly and delivery capsule of FIG. 7C, consistent with various embodiments of the present disclosure.
Figure 7C:
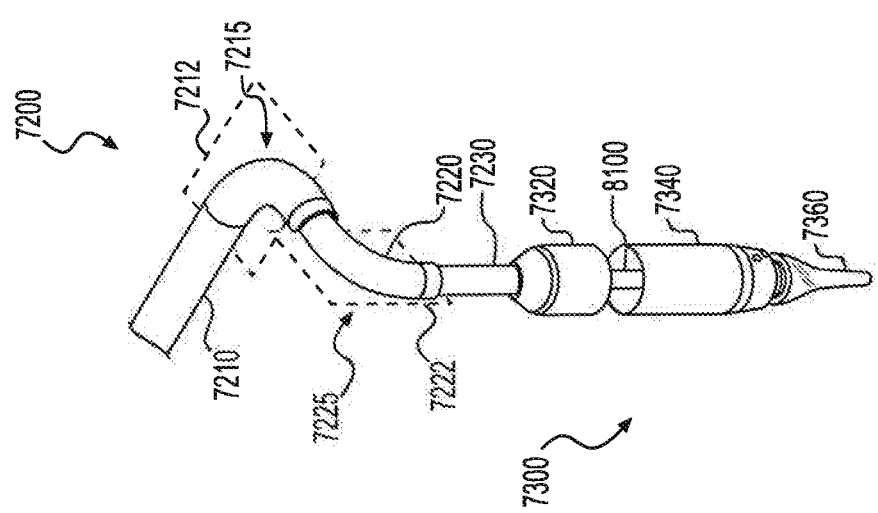
FIG. 7C illustrates an exemplary configuration of a telescoping catheter assembly and the delivery capsule of the exemplary prosthetic valve delivery system of FIG. 7A, consistent with various embodiments of the present disclosure.

FIGS. 7C and 7D illustrate exemplary configurations of the telescoping catheter assembly 7200. Outer sheath 7210 and guide catheter 7220 may include respective bending portions 7215 and 7225, at which the outer sheath 7210 and guide catheter 7220 may be configured to bend within their respective steering planes 7212 and 7222. In some embodiments, bending of the outer sheath 7210 within the first steering plane 7212 may be controlled by the outer sheath steering knob 7122 of the control handle assembly 7100. Additionally, or alternatively, bending of the guide catheter 7220 within the second steering plane 7222 may be controlled by the guide catheter steering knob 7142 of the control handle assembly 7100. In some embodiments, under control of the control handle assembly 7100, the outer sheath 7210, guide catheter 7220, and implant catheter 8100 may be steered so as to correctly position the delivery capsule 7300 within a native valve for implantation of the prosthetic valve.

Figure 8A:
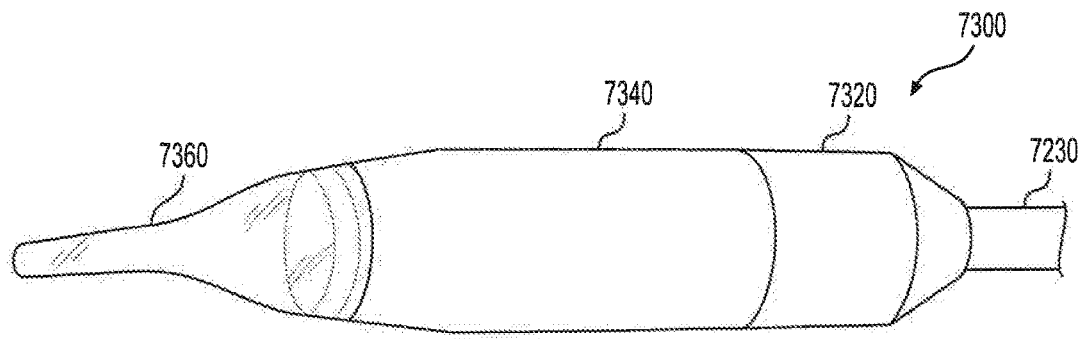
FIG. 8A illustrates another enlarged view of the exemplary delivery capsule of the prosthetic valve delivery system of FIG. 7A in a closed configuration, consistent with various embodiments of the present disclosure.
Figure 8B:
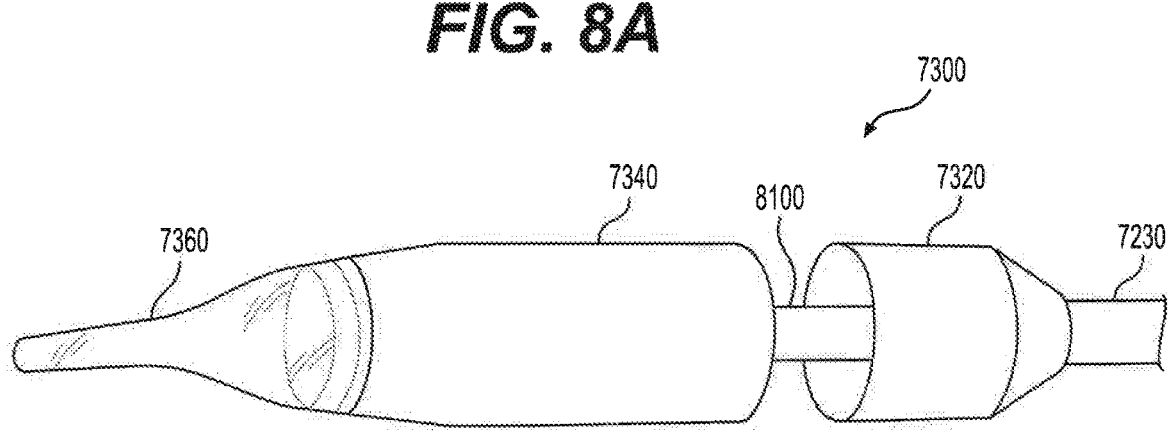
FIG. 8B illustrates the exemplary delivery capsule of FIG. 8A in an open configuration, consistent with various embodiments of the present disclosure.
Figure 8C:
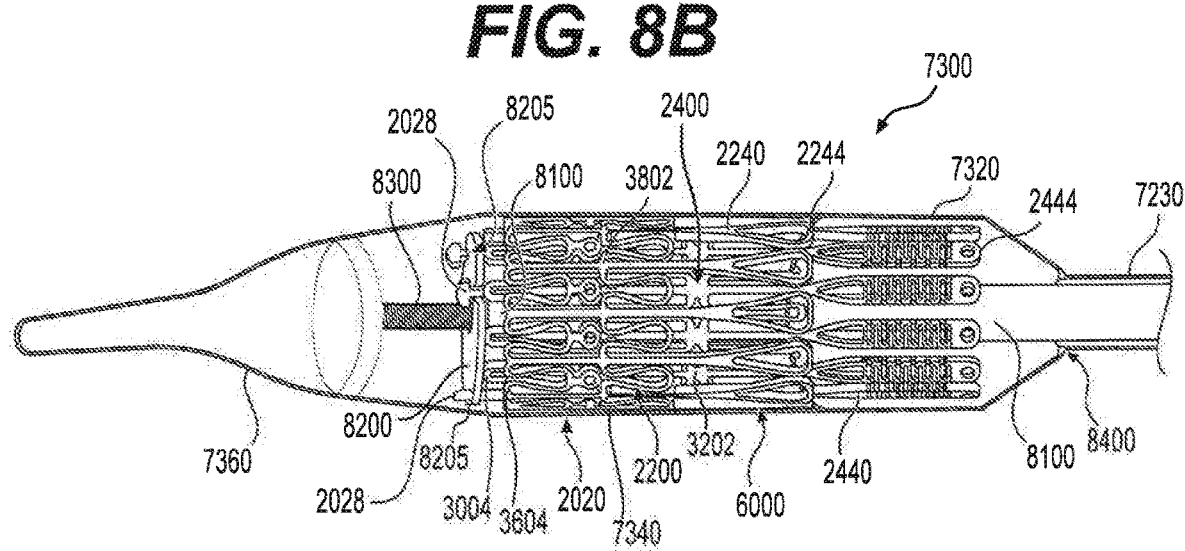
FIG. 8C illustrates an interior view of the exemplary delivery capsule of FIG. 8A in the closed configuration, consistent with various embodiments of the present disclosure.

FIG. 8A illustrates an enlarged view of delivery capsule 7300 in a closed configuration, while FIG. 8B illustrates an enlarged view of delivery capsule 7300 in an open configuration. In the closed configuration of FIG. 8A, the distal capsule portion 7340 and proximal capsule portion 7320 may be brought together to form an enclosed compartment in which prosthetic valve 6000 may be retained. In the open configuration of FIG. 8B, the distal capsule portion 7340 and proximal capsule portion 7320 may be drawn apart. In some embodiments, the delivery capsule 7300 may be configured such that the distal capsule portion 7340 and proximal capsule portion 7320 are moved apart from each other, the prosthetic valve 6000 may be sequentially deployed from within the delivery capsule and implanted within a native valve.

FIG. 8C illustrates an interior view of delivery capsule 7300 with prosthetic valve 6000 retained within the delivery capsule. Although only the valve frame 2000 of the prosthetic valve 6000 is illustrated in FIG. 8C, one of ordinary skill will understand that the entire prosthetic valve 6000 depicted in FIGS. 6A-6E may be retained within delivery capsule 7300 in the configuration illustrated in FIG. 8C.

In the embodiment illustrated in FIG. 8C, at least a portion of the annular valve body 2020 and ventricular anchoring legs 2240 of the prosthetic valve 6000 may be retained within the distal capsule portion. Additionally, or alternatively, at least a portion of atrial anchoring arms 2440 may be retained within proximal capsule portion 7320. In some embodiments, valve anchor disc 8200 may include a number of recesses 8205 configured to receive and retain the ventricular end delivery posts 2028 of the prosthetic valve 6000. For example, the valve anchor disc 8200 may include at least the same number of recesses 8205 as there are delivery posts 2028 of the prosthetic valve 6000. In some embodiments, the delivery posts 2028 may be retained within the recesses 8205 so long as the annular valve body 2020 remains in a radially-contracted configuration; the engagement between the valve anchor disc 8200 and delivery posts 2028 may secure the prosthetic valve 6000 against axial movement. Upon radial expansion of the annular valve body 2020, the delivery posts 2028 may slide or expand out of the recesses 8205, freeing the prosthetic valve 6000 from engagement with the valve anchor disc 8200.

Figure 9:
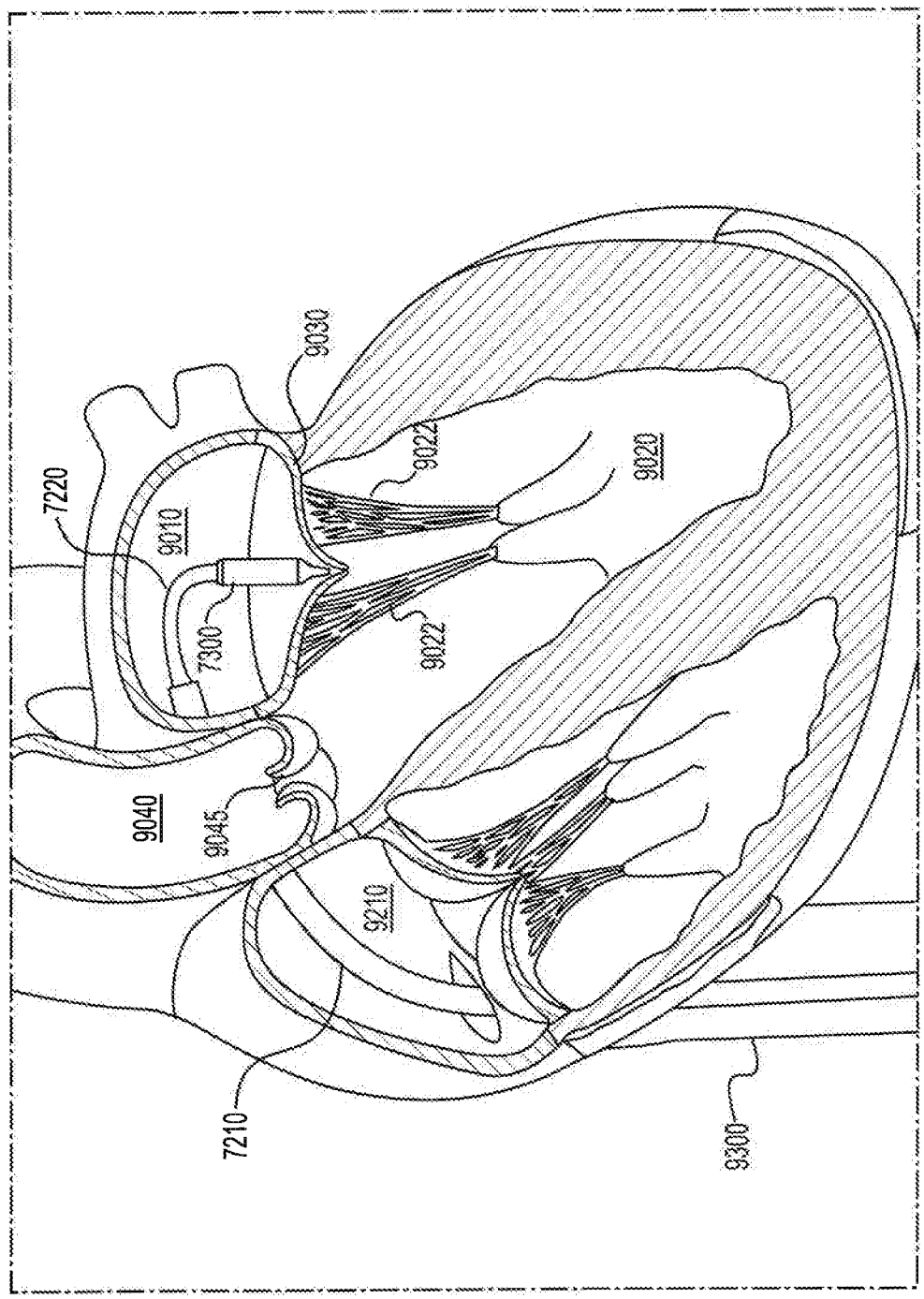
FIG. 9 illustrates advancement of the exemplary prosthetic valve delivery system of FIG. 7A into the left atrium, consistent with various embodiments of the present disclosure.

FIG. 9 illustrates one exemplary advancement route of the delivery capsule 7300 to the left atrium. In the example illustrated in FIG. 9, the delivery capsule 7300 may be steered through the vena cava into the right atrium 9210 and may pierce the interatrial septum and enter the left atrium 9010. Alternatively, the delivery capsule may be delivered to the heart by other routes. FIG. 9 also depicts the left ventricle 9020, the mitral valve 9030, the chordae tendineae 9022, the aortic valve 9045, and the aorta 9040.

Figure 10B:
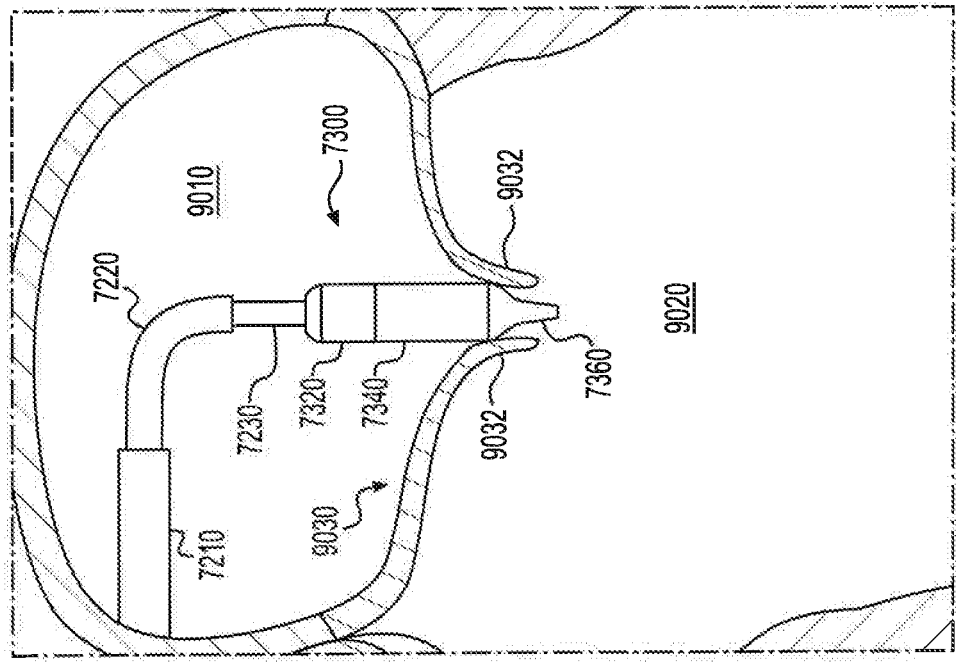
FIGS. 10A-10H depict implantation of the prosthetic valve of FIGS. 6A-6E within a native mitral valve by the exemplary prosthetic valve delivery system of FIG. 7A, consistent with various embodiments of the present disclosure.
Figure 10A:
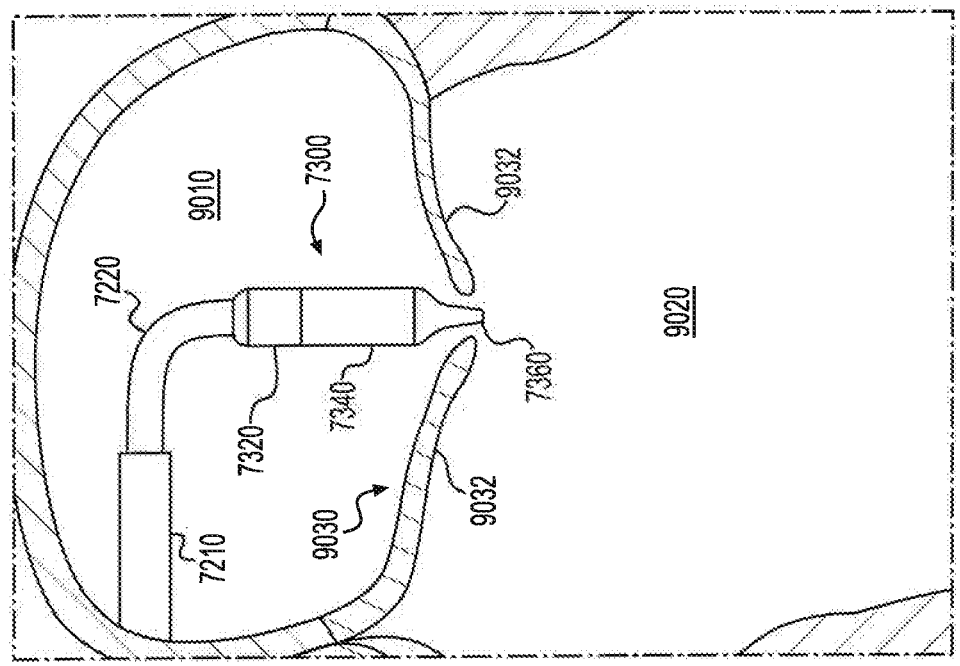
Figure 10D:
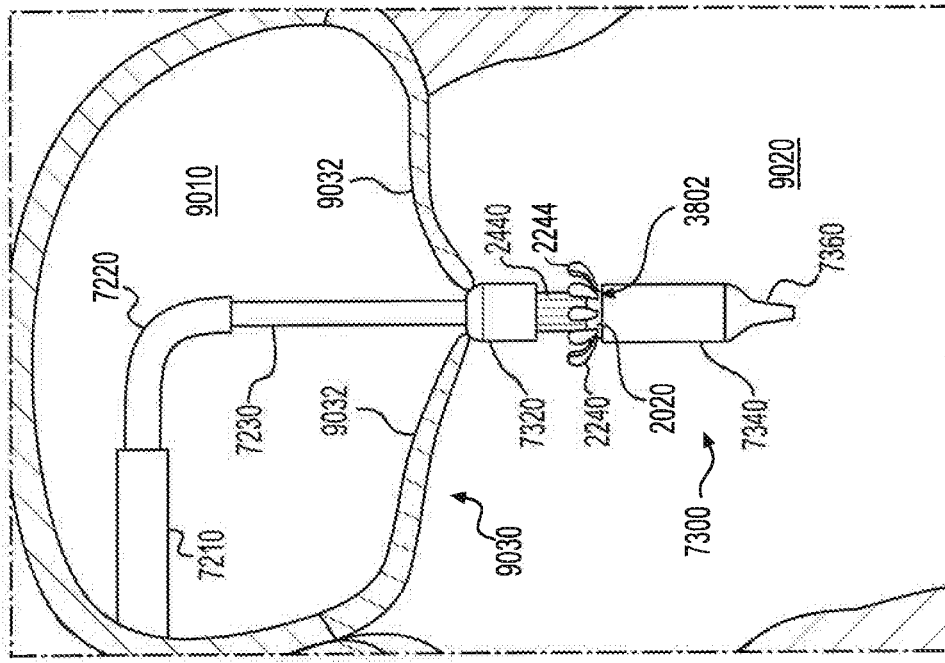
Figure 10C:
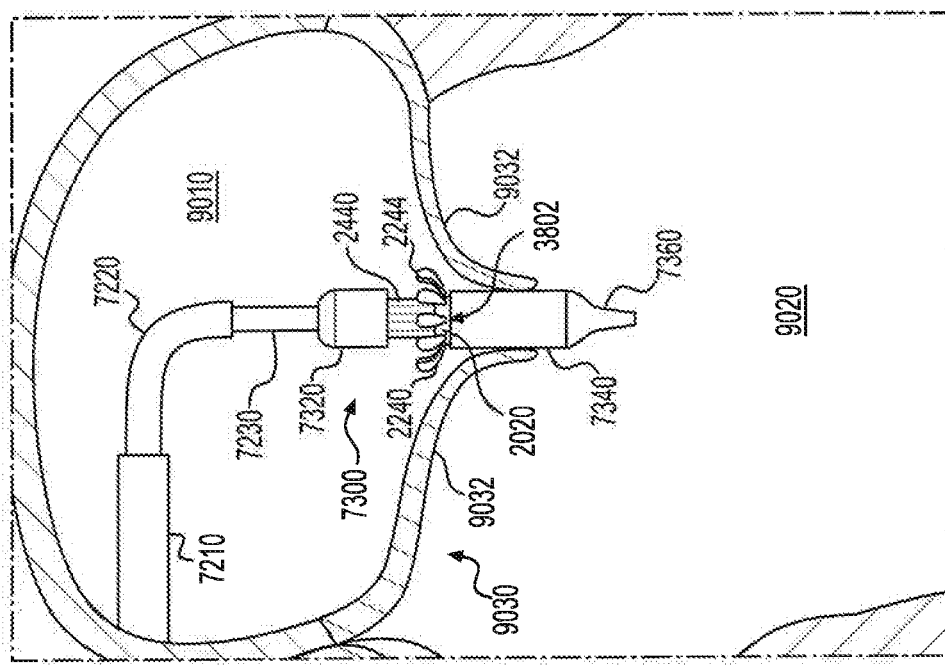

FIGS. 10A-10H depict an exemplary implantation method of prosthetic valve 6000 within a mitral valve 9030. In FIG. 10A, the delivery capsule 7300 may be coaxially aligned with the mitral valve 9030. In some embodiments, the prosthetic valve 6000 may be held within the delivery capsule 7300 while the prosthetic valve is arranged in the configuration of FIG. 5A. In FIG. 10B, the delivery capsule 7300 may be distally advanced into the mitral valve 9030. In FIG. 10C, the distal capsule portion 7340 may be distally advanced relative to the rest of the delivery capsule 7300. This may release the ventricular anchoring legs 2240 from the distal capsule portion 7340, while the atrial anchoring arms 2440 and annular valve body 2020 remain constrained within the delivery capsule. In the example shown in FIG. 10C, the ventricular anchoring legs 2240 may be released from the delivery capsule 7300 within the atrium 9010. In some embodiments, the prosthetic valve 6000 may assume the configuration of FIG. 5B when the ventricular anchoring legs 2240 are released in the step depicted in FIG. 10C.

Figure 10F:
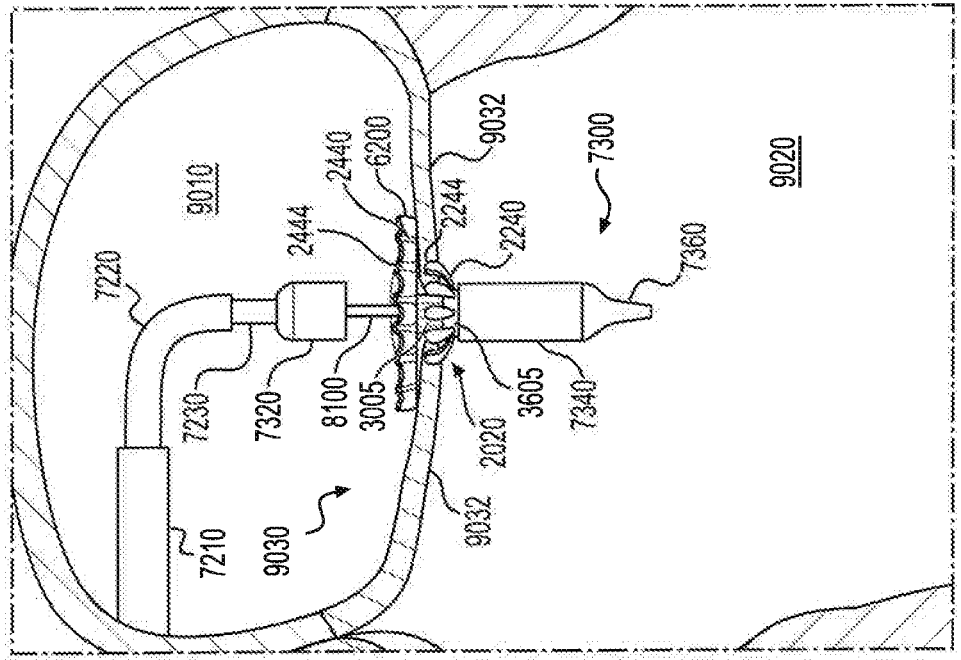
Figure 10E:
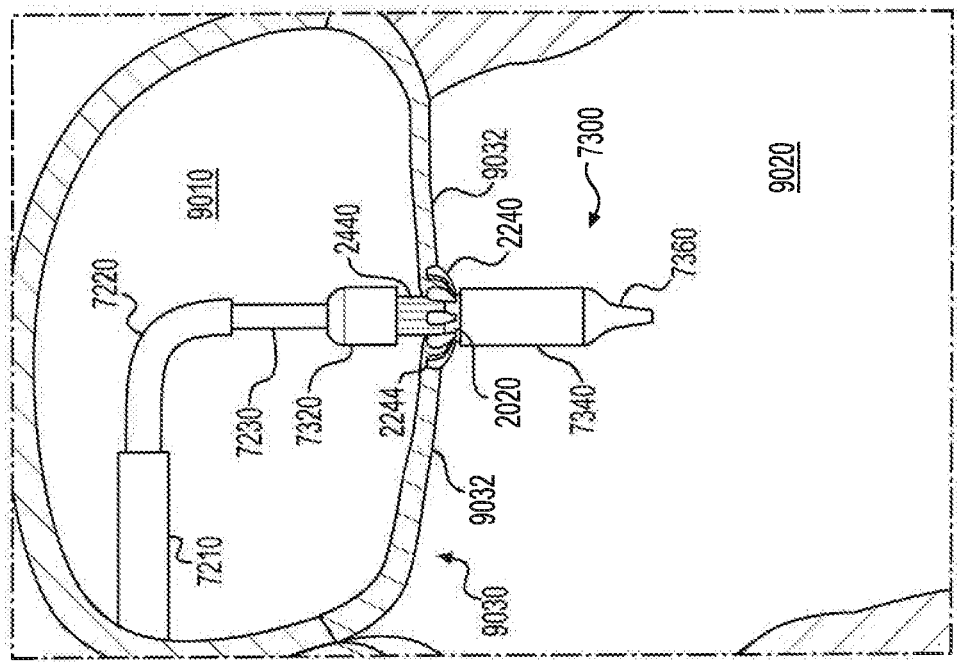

In FIG. 10D, the released ventricular anchoring legs 2240 may be passed through the mitral valve 9030 and into the left ventricle 9020. In FIG. 10E, the released legs 2240 may be proximally retracted until the ventricular anchoring legs come into contact with the ventricular tissue of the mitral valve 9030. In FIG. 10F, the proximal capsule portion 7320 may be retracted proximally, thus releasing the atrial anchoring arms 2440 within atrium 9010 while the annular valve body 2020 remains radially constrained within the distal capsule portion 7340. In some embodiments, the prosthetic valve 6000 may assume the configuration of FIG. 5D when the atrial anchoring arms 2440 are released in the step of FIG. 10F.

Figure 10H:
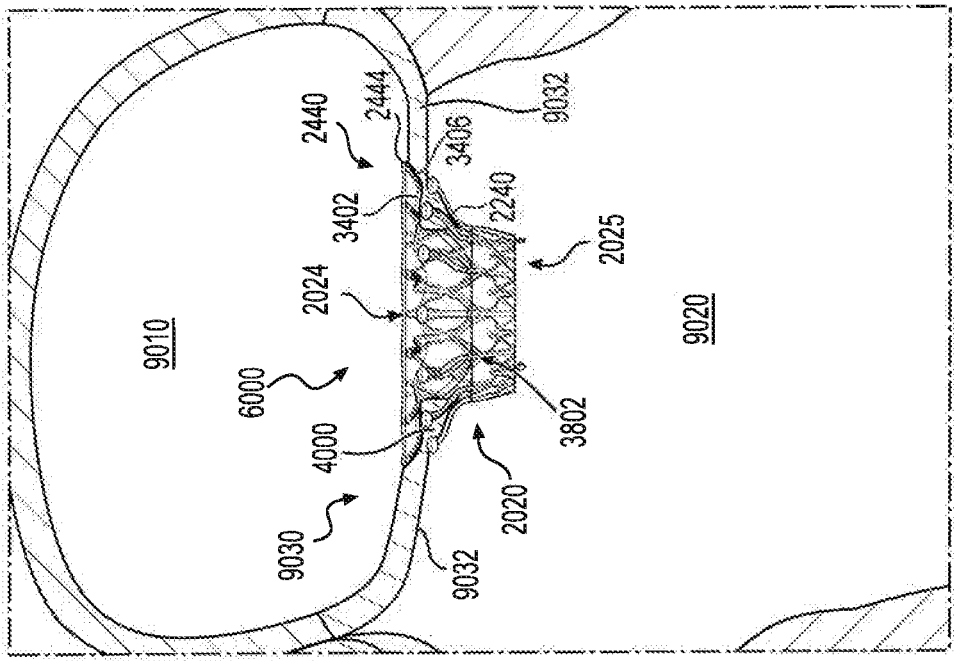
Figure 10G:
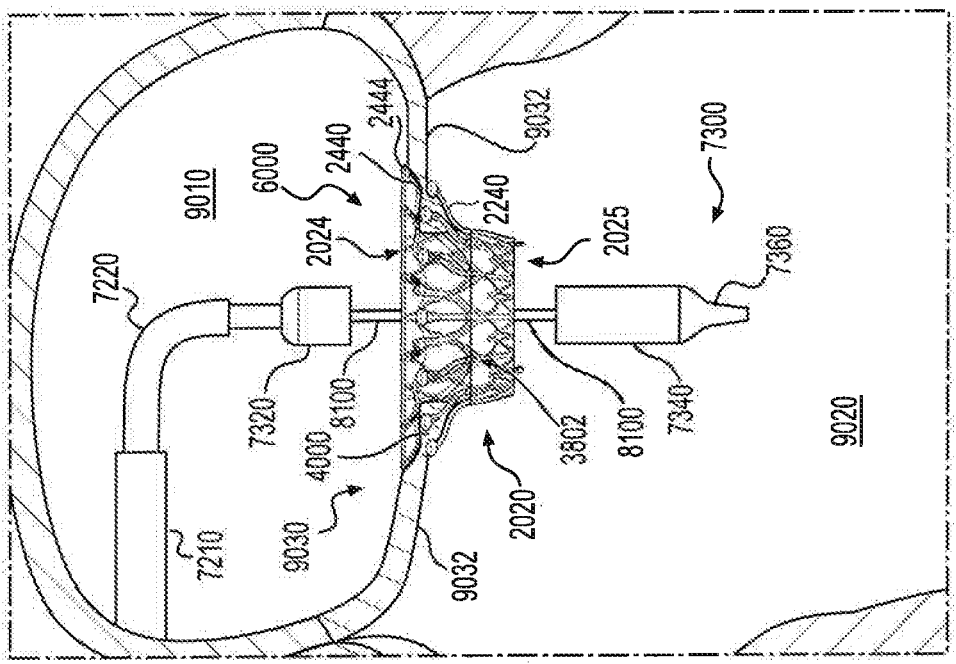

In FIG. 10G, the distal capsule portion 7340 may be advanced further until the annular valve body 2020 is released from the capsule and allowed to radially expand. Radial expansion of the annular valve body 2020 may allow the prosthetic valve to assume the fully-expanded configuration illustrated in FIG. 5E. At this stage, prosthetic valve 6000 may be securely implanted within mitral valve 9030. In FIG. 10H, the delivery system 7000, including capsule 7300, may be removed.

Various embodiments of the present disclosure relate to prosthetic valves, including prosthetic heart valves. While the present disclosure provides examples of prosthetic heart valves, and in particular prosthetic mitral valves, it should be noted that aspects of the disclosure in their broadest sense are not limited to a prosthetic mitral valve. Rather, the foregoing principles may be applied to other prosthetic valves as well. Prosthetic heart valve 6000, illustrated in FIGS. 6A-6E, is one example of a prosthetic valve according to the present disclosure.

In some embodiments, an exemplary prosthetic valve may be configured for implantation within a native atrioventricular valve and may regulate blood flow between the atrium and ventricle. For example, prosthetic heart valve 6000 illustrated in FIGS. 6A-6C may include a fluid-impervious cuff 6200 configured to extend from an inner lumen 2022 of the prosthetic valve to terminal arm ends 2444 of a plurality of atrial anchoring arms 2440. Because cuff 6200 is constructed of a fluid-impervious material, cuff 6200 may be configured to minimize or block flow of blood and other fluids through any portion of the prosthetic valve 6000 except for lumen 2022. In addition, atrial anchoring arms 2440 of the prosthetic valve (including terminal arm ends 2444) may be configured to contact and, in some embodiments, press against atrial tissue of a native heart valve. This is illustrated in FIGS. 10G-10H, which depict atrial anchoring arms 2440 of prosthetic valve 6000 arranged in contact with, and exerting a ventricularly-directed force (that is, a force directed downwards toward ventricle 9020) upon atrial tissue of native mitral valve 9030. As a result, cuff 6200 of prosthetic valve 6000 may also be configured to minimize or block passage of blood and other fluids between the prosthetic valve 6000 (including terminal arm ends 2444) and native valve tissue, a condition known as perivalvular leakage. As a result, prosthetic valve 6000 may be configured to prohibit passage of blood and other fluids between atrium 9010 and ventricle 9020, except by passage through inner lumen 2022, in which leaflets 6602, 6604, and 6606 may be situated.

In some embodiments, an exemplary prosthetic valve may be expandable, such as between a radially-contracted configuration (for example, a crimped state) and a radially-expanded configuration. In some embodiments, the exemplary prosthetic valve may be configured to be radially contracted into the radially-contracted configuration for introduction to the implantation site, such as on or within a delivery device. Accordingly, in some embodiments, the radially-contracted configuration may also be a delivery configuration, in which the prosthetic valve is arranged for delivery to the implantation site. Once at or near the implantation site, the prosthetic valve may be fully radially-expanded, which may anchor the prosthetic valve at the implantation site. Accordingly, in some embodiments, the radially-expanded configuration may also be a deployed configuration, in which the prosthetic valve is released from the delivery tool and seated at the implantation site.

In some embodiments, an exemplary prosthetic valve may be configured for self-expansion to the radially-expanded configuration; that is, the prosthetic valve may be biased to assume the radially-expanded configuration due to, at least in part, the design and/or material composition of the prosthetic valve. The self-expanding prosthetic valve may be constructed of a shape memory material such as nickel titanium alloy (Nitinol), which may permit the prosthetic valve to expand to a pre-determined diameter upon removal of a constraining force and/or application of heat or energy. For example, the prosthetic valve may be contracted and held in the radially-contracted configuration by a constraining device, such as a sheath, catheter, stent, or delivery capsule. An example of such a constraining device is illustrated in FIGS. 8A-8O, which illustrates prosthetic heart valve 6000 held in a radially-contracted configuration within delivery capsule 7300. When the prosthetic valve is positioned at or near the implantation site, the constraining force may be removed and the prosthetic valve allowed to self-expand to the radially-expanded configuration. Additionally, or alternatively; an exemplary prosthetic valve may be configured to expand due to application of radially expansive forces thereupon. For example, the prosthetic valve may be placed, in its radially-contracted configuration, upon an expansion device such as a balloon catheter. Upon positioning at the implantation site, the expansion device may exert an outwardly-directed force upon the prosthetic valve, causing it to expand to the fully-expanded configuration.

In some embodiments, a prosthetic valve may be configured for implantation at a treatment site within the body, such as within or adjacent to a native valve structure, such as a native mitral valve. In some embodiments, a prosthetic valve may be configured for transcatheter delivery to the implantation site via a variety of approaches, such as transapically, transatrially, and/or transseptally. In some embodiments, the prosthetic valve may be configured for implantation in the annulus or orifice of a native valve structure (e.g., a native mitral valve). For example, in FIGS. 10A-10H, prosthetic valve 6000 may be delivered to and expanded within native mitral valve 9030 such that prosthetic valve 6000 is anchored within native mitral valve 9030. In some embodiments, an exemplary prosthetic valve may be configured to grasp tissue of the native valve to firmly anchor the prosthetic valve within the native valve. For example, an exemplary prosthetic valve may be configured to grasp the native leaflets and/or native valve annulus to firmly seat the prosthetic valve within the valve annulus, thus preventing the prosthetic valve from migrating or dislodging from within the native valve annulus.

In some embodiments, the prosthetic valve may include a valve body. The exemplary valve body may be configured to receive or otherwise support a flow control device, such as one or more leaflets, for regulating flow of blood or other bodily fluids through the prosthetic valve. For example, the flow control device (e.g., leaflets) may be secured directly to the valve body and/or to an additional structure that is in turn secured to the valve body. As a result, when the prosthetic valve is implanted within a native valve (e.g., a mitral valve), the flow control device may regulate fluid passage through the native valve, thus restoring and/or replacing the functionality of the native valve. In some embodiments, the exemplary valve body may be annular or ring-shaped and may thus have at least one opening therein. In some embodiments, the at least one opening may extend longitudinally along the entire length of the valve body. For example, as illustrated in FIG. 2B, valve body 2020 may include axial lumen 2022 extending longitudinally through valve body 2020. The valve body may be sized and configured to be seated within the orifice of a native heart valve (e.g., a native mitral valve). For example, as depicted in FIG. 10H, valve body 2020 may be situated within the orifice of mitral valve 9030, specifically between native leaflets 9032. In some embodiments, the valve body may be configured to have a smaller diameter, when fully-expanded, than the diameter of the orifice of the native heart valve. In such embodiments, the valve body may be anchored in the native heart valve by anchoring structures, such as atrial anchoring arms and/or ventricular anchoring legs. Alternatively, the valve body may be configured to expand to an equal or greater diameter than the diameter of the native heart valve orifice such that the valve body is anchored within the native heart valve.

The valve body may have a circular, oval-shaped, elliptical, or D-shaped cross-section and may be symmetrical about at least one axis thereof. Alternatively, the valve body may have any suitable cross-sectional shape with at least one opening therein. In some embodiments, at least a portion of the valve body may be cylindrical, with a substantially constant diameter along the entire length thereof. Alternatively, the valve body may have a variable diameter at different portions thereof (e.g., at different longitudinal portions thereof). Advantageously, such a configuration may improve the seating of the valve body within the native heart valve orifice, providing an improved pressure fit therebetween.

In some embodiments, the exemplary valve body may be expandable, such as between a radially-contracted configuration and a radially-expanded configuration. In some embodiments, an exemplary valve body may be configured to be radially contracted into the radially-contracted configuration for introduction to the implantation site, such as on or within a delivery device. Accordingly, in some embodiments, the radially-contracted configuration may also be a delivery configuration, in which the valve body is arranged for delivery to the implantation site. Once at or near the implantation site, the valve body may be radially expanded, which may anchor the valve body at the implantation site. Accordingly, in some embodiments, the radially-expanded configuration may also be a deployed configuration, in which the valve body is released from the delivery tool and seated at the implantation site.

In some embodiments, an exemplary valve body may be configured for self-expansion to the radially-expanded configuration; that is, the valve body may be biased to assume the radially-expanded configuration due to, at least in part, the design and/or material composition of the valve body. The self-expanding valve body may be constructed of a shape memory material such as nickel titanium alloy (Nitinol), which may permit the valve body to expand to a pre-determined diameter upon removal of a constraining force and/or application of heat or energy. For example, the valve body may be contracted and held in the radially-contracted configuration by a constraining device, such as a sheath, catheter, stent, or delivery capsule. An example of such a constraining device is illustrated in FIGS. 8A-8C, which illustrate an exemplary prosthetic heart valve held in a radially-contracted configuration within delivery capsule 7300. When the valve body is positioned at or near the implantation site (e.g., at the native mitral valve 9030), the constraining force (e.g., as applied by delivery capsule 7300) may be removed and the valve body allowed to self-expand to the radially-expanded configuration. Additionally, or alternatively, exemplary valve bodies may be configured to expand due to application of radially expansive forces thereupon. For example, the valve body may be placed, in its radially-contracted configuration, upon an expansion device such as a balloon catheter. Upon positioning at the implantation site, the expansion device may exert an outwardly-directed force upon the valve body, causing it to expand to the fully-expanded configuration.

In some embodiments, the exemplary valve body may be configured to radially expand independently of other components of the expandable prosthetic valve. As a result, the exemplary valve body may be configured to remain in a radially-contracted configuration while other components of the expandable prosthetic valve, such as an anchoring feature, are deployed radially outward. For example, FIGS. 5B-5D depict exemplary heart valve frame 2000 having valve body 2020 configured to remain in a radially-contracted configuration while atrial anchoring arms 2440 and ventricular anchoring legs 2240 are deployed radially outward (e.g., due to removal of a constraining delivery device from the arms and legs).

In some embodiments, the exemplary valve body may include an atrial end. In some embodiments, the term atrial end may refer to a portion of a feature of the valve body configured to be situated closest to an atrium of the heart when the feature is positioned outside of the atrium. Additionally, or alternatively, the term atrial end may refer to a portion of a feature of the valve body configured to be situated at a location within the atrium that is furthest from an adjacent ventricle. For example, as depicted in FIGS. 2A and 3A, atrial end inner frame junctions 3002 may constitute the atrial end 2024 of valve body 2020 because they are the portions of valve body 2020 that are situated within atrium 9010 at a location furthest from ventricle 9020 (as shown in FIG. 10H). In some embodiments, the exemplary valve body may include a ventricular end. In some embodiments, the term ventricular end may refer to a portion of a feature of the valve body configured to be situated closest to a ventricle of the heart when the feature is positioned outside of the ventricle. Additionally, or alternatively, the term ventricular end may refer to a portion of a feature of the valve body configured to be situated at a location within the ventricle that is furthest from an adjacent atrium. For example, in some embodiments and as depicted in FIGS. 2A, 3A, and 3C, ventricular end inner frame junction 3004 and ventricular end outer frame junction 3604 may constitute the ventricular end 2025 of valve body 2020. In some alternative embodiments, ventricular end inner frame junction 3004 may constitute the ventricular end 2025 of valve body 2020. In some further alternative embodiments, ventricular end outer frame junction 3604 may constitute the ventricular end 2025 of valve body 2020.

In some embodiments, the exemplary valve body may include both an atrial end and a ventricular end opposite the atrial end. That is, the ventricular end of the valve body may be situated at a portion of the valve body that is furthest from and opposite of the atrial end of the valve body, with respect to a longitudinal axis of the valve body. In some embodiments, the exemplary valve body may include an intermediate portion extending between the atrial end and ventricular end of the valve body. In some embodiments, the intermediate portion of the valve body may constitute every portion of the valve body situated in between the atrial end and ventricular end of the valve body. For example, as depicted in FIG. 2A, intermediate portion 2026 of valve body 2020 may include every portion of the valve body positioned between atrial end 2024 and ventricular end 2025.

In some embodiments, the exemplary valve body may include a plurality of supporting members or struts. In some embodiments, the struts may intersect at junctions to form a wire mesh, stent-like, or cage-like structure of the valve body. In some embodiments, the struts of the valve body may be made of metals or alloys such as Nitinol. In some embodiments, the struts of the valve body may be straight or curved. In some embodiments, the struts of the valve body may be straight at certain portions of the struts and curved at other portions of the struts. In other embodiments, the struts may be longitudinal or undulating. In some embodiments, the plurality of struts may refer to two, three, four, five, six, seven, eight, nine, or ten struts. In other embodiments, the plurality of struts may refer to at least ten, at least twenty, at least thirty, at least forty, or at least fifty struts. For example, FIG. 3A depicts inner frame atrial struts 3008a, inner frame intermediate struts 3008b, and inner frame ventricular struts 3008c within valve body 2020, and FIG. 3C depicts outer frame atrial circumferential struts 3608a, outer frame leg base struts 3608b, and outer frame ventricular circumferential struts 3608c within valve body 2020. In some embodiments, the struts of the valve body may meet or intersect at junctions of the valve body. A junction may be formed at a location at which at least two struts terminate that is, one or more exemplary struts may extend to and terminate at a junction at which the one or more exemplary struts intersects with one or more other struts. In some embodiments, the struts may intersect at junctions to form a lattice or overlapping pattern. In some embodiments, the struts may intersect at junctions to form cells, which may have any suitable cell shape. In certain embodiments, the struts of the valve body may intersect at junctions to form closed cells (i.e., cells completely enclosed by struts). In certain embodiments, the closed cells may be diamond-shaped, chevron-shaped, rectangular, triangular, circular, or may have any other suitable shape. For example, FIG. 3A depicts cells 3012 and 3014 in inner frame 2400 of valve body 2020, and FIG. 3C depicts cells 3616 in outer frame 2200 of valve body 2020. In some embodiments, two struts, three struts, four struts, five struts, or any other suitable number of struts may intersect at junctions of the valve body.

In some embodiments, the struts of the valve body may be arranged so as to form one or more frames of the exemplary prosthetic valve.

In some embodiments, the prosthetic valve may include one or a plurality of tissue anchoring legs configured to anchor the prosthetic valve at the implantation site, such as within or near a native heart valve. In some embodiments, the tissue anchoring legs may be configured to engage ventricular tissue of a native mitral valve to anchor the prosthetic valve. In some embodiments, the tissue anchoring legs may be configured to be positioned at least partially within a ventricle upon implantation of the prosthetic valve, and to engage ventricular tissue of the native mitral valve. For example, FIGS. 10E-10H depict tissue anchoring legs 2240 of an exemplary prosthetic heart valve situated within ventricle 9020 and engaging the ventricular side of native mitral valve 9030. In some embodiments, the tissue anchoring legs may be configured to minimize or prevent migration of the prosthetic valve, including in an atrial direction (that is, towards the atrium). This may be due, at least in part, to the engagement of the tissue anchoring legs with the ventricular side of the native mitral valve and the inability of the tissue anchoring legs to pass through the valve annulus when the legs are expanded. In some embodiments, the tissue anchoring legs may be configured to grasp or clamp tissue of the native mitral valve to further anchor the prosthetic valve in place. Optionally, one or more tissue anchoring legs may include an anchoring feature to couple the legs to surrounding tissue.

The prosthetic valve may include two tissue anchoring legs, three tissue anchoring legs, four tissue anchoring legs, five tissue anchoring legs, six tissue anchoring legs, seven tissue anchoring legs, eight tissue anchoring legs, nine tissue anchoring legs, ten tissue anchoring legs, eleven tissue anchoring legs, twelve tissue anchoring legs, thirteen tissue anchoring legs, fourteen tissue anchoring legs, fifteen tissue anchoring legs, sixteen tissue anchoring legs, seventeen tissue anchoring legs, eighteen tissue anchoring legs, nineteen tissue anchoring legs, twenty tissue anchoring legs, or any other suitable number of tissue anchoring legs. For example, exemplary prosthetic valve 6000 may include twelve tissue anchoring legs 2240.

In some embodiments, the tissue anchoring legs may be configured to extend from an intermediate portion of the exemplary valve body. That is, the tissue anchoring legs may be configured to extend from a portion of the valve body other than the valve body atrial end and the valve body ventricular end. For example, tissue anchoring legs 2240, in FIG. 2A, extend from intermediate portion 2026 of valve body 2020. In some exemplary embodiments, the tissue anchoring legs may be configured to extend from junctions situated within the intermediate portion of the valve body. In some exemplary embodiments, the tissue anchoring legs may be physically connected to the junctions within the intermediate portion of the valve body, such as by welding or adhesive. In some alternative embodiments, the tissue anchoring legs may be integrally formed with the junctions within the intermediate portion of the valve body. In some embodiments, the tissue anchoring legs may be configured to extend from a single junction of the valve body. Alternatively, the tissue anchoring legs may be configured to extend from more than one junction of the valve body. For example, in FIG. 3C, tissue anchoring legs 2240 extend from leg attachment junctions 3802 within outer frame 2200 of valve body 2020.

In some embodiments, the locations of connection between the tissue anchoring legs and annular valve body may be spaced at a regular interval about a circumference of the valve body. For example, in FIG. 2A, the ventricular anchoring legs 2240 may extend from the annular valve body 2020 at leg attachment junctions 3802. Leg attachment junctions 3802 may be spaced at a regular interval about the circumference of annular valve body 2020. Additionally, or alternatively, the locations of connection between the tissue anchoring legs and valve body may be arranged along a plane perpendicular to the longitudinal axis of the prosthetic valve. For example, in FIG. 2A, the leg attachment junctions 3802 may be arranged along a plane perpendicular to longitudinal axis 2800. That is, the leg attachment junctions 3802 may be situated at the same axial position along longitudinal axis 2800.

In some embodiments, at least one of the tissue anchoring legs may have a cross-sectional area. A cross-sectional area may refer to the two-dimensional area of a cross-sectional portion of the tissue anchoring leg which is perpendicular to the tissue anchoring leg. For example, as depicted on FIG. 3C, tissue anchoring leg 2240 may have a cross-sectional area 3624 that is perpendicular to the portion of the tissue anchoring leg in which it is located. In some embodiments, the at least one tissue anchoring leg may have a constant cross-sectional area along at least a portion of its length or along its entire length. The term entire length may refer to the portion of the tissue anchoring leg extending between a point of connection with a valve body and a terminal end of the tissue anchoring leg. In some alternative embodiments, the at least one tissue anchoring leg may have a variable cross-sectional area along its length. In some further embodiments, the at least one tissue anchoring leg may have a constant cross-sectional area along a certain portion of its length and a variable cross-sectional area along the remainder of its length. For example, in FIG. 3C, tissue anchoring legs 2240 may exhibit a constant cross-sectional area between leg attachment junction 3802 and opening 2242. The cross-sectional area of the tissue anchoring legs 2240 decreases at opening 2242. In some embodiments, a plurality of tissue anchoring legs in the valve body may have equal cross-sectional areas. In some alternative embodiments, at least one tissue anchoring leg may have a different cross-sectional area relative to the cross-sectional areas of other tissue anchoring legs.

In some embodiments, the prosthetic valve may include a strut extending between the at least one tissue anchoring leg and an adjacent tissue anchoring leg (that is, the nearest of the other tissue anchoring legs) within an intermediate portion of the exemplary valve body. In some embodiments, the strut may partly extend between the at least one tissue anchoring leg and the adjacent tissue anchoring leg. For example, at least one additional strut may be situated between the strut and the at least one tissue anchoring leg and/or between the strut and the adjacent tissue anchoring leg. In some exemplary embodiments, the strut may extend for substantially half the distance between the at least one tissue anchoring leg and the adjacent tissue anchoring leg. For example, outer frame atrial circumferential strut 3608a, in FIG. 3C, extends for half the distance between adjacent tissue anchoring legs 2240 (specifically, outer frame atrial circumferential strut 3608a extends between leg attachment junction 3802 and atrial end outer frame junction 3602). In some alternative embodiments, the strut may fully extend between the at least one tissue anchoring, leg and the adjacent tissue anchoring leg. In some embodiments, the strut may extend from, or be physically connected to, one or more of the at least one tissue anchoring leg and the adjacent tissue anchoring leg.

In some embodiments, the strut extending between the at least one tissue anchoring leg and the adjacent tissue anchoring leg may have a cross-sectional area. The cross-sectional area may be the two-dimensional area of a cross-sectional portion of the strut which is perpendicular to the strut. For example, as depicted in FIG. 3C, outer frame atrial circumferential strut 3608a may have a cross-sectional area 3610 that is perpendicular to the portion of the strut in which it is located. In some embodiments, the strut may have a constant cross-sectional area along its entire length. In some alternative embodiments, the strut may have a variable cross-sectional area along its entire length. In some further alternative embodiments, the strut may have a constant cross-sectional area along a certain portion of its length and a variable cross-sectional area along the remainder of its length.

In some embodiments, the cross-sectional areas of the at least one tissue anchoring leg and the strut extending between the at least one tissue anchoring leg and the adjacent tissue anchoring leg may be substantially equal. In some alternative embodiments, the cross-sectional area of the at least one tissue anchoring leg may be at least 10% larger than the cross-sectional area of the strut. In some further embodiments, the cross-sectional area of the at least one tissue anchoring leg may be at least 20% larger, at least 30% larger, at least 40% larger, or at least 50% larger than the cross-sectional area of the strut. In some embodiments, the at least one tissue anchoring leg may have a cross-sectional area between 0.45 mm$^2$ and 0.65 mm$^2$. For example, and without limitation, the at least one tissue anchoring leg may have a cross-sectional area of 0.45 mm$^2$, 0.46 mm$^2$, 0.47 mm$^2$, 0.48 mm$^2$, 0.49 mm$^2$, 0.50 mm$^2$, 0.51 mm$^2$, 0.52 mm$^2$, 0.53 mm$^2$, 0.54 mm$^2$, 0.55 mm$^2$, 0.56 mm$^2$, 0.57 mm$^2$, 0.58 mm$^2$, 0.59 mm$^2$, 0.60 mm$^2$, 0.61 mm$^2$, 0.62 mm$^2$, 0.63 mm$^2$, 0.64 mm$^2$, 0.65 mm$^2$, or any other suitable cross-sectional area. Additionally, or alternatively, the strut extending between the at least one tissue anchoring leg and the adjacent tissue anchoring leg may have a cross-sectional area between 0.15 mm$^2$ and 0.3 mm$^2$. For example, and without limitation, the strut extending between the at least one tissue anchoring leg and the adjacent tissue anchoring leg may have a cross-sectional area of 0.15 mm$^2$, 0.155 mm$^2$, 0.16 mm$^2$, 0.165 mm$^2$, 0.17 mm$^2$, 0.175 mm$^2$, 0.18 mm$^2$, 0.185 mm$^2$, 0.19 mm$^2$, 0.195 mm$^2$, 0.20 mm$^2$, 0.205 mm$^2$, 0.21 mm$^2$, 0.215 mm$^2$, 0.22 mm$^2$, 0.225 mm$^2$, 0.23 mm$^2$, 0.235 mm$^2$, 0.24 mm$^2$, 0.245 mm$^2$, 0.25 mm$^2$, 0.251 mm$^2$, 0.252 mm$^2$, 0.253 mm$^2$, 0.254 mm$^2$, 0.255 mm$^2$, 0.256 mm$^2$, 0.257 mm$^2$, 0.258 mm$^2$, 0.259 mm$^2$, 0.26 mm$^2$, 0.265 mm$^2$, 0.27 mm$^2$, 0.275 mm$^2$, 0.28 mm$^2$, 0.285 mm$^2$, 0.29 mm$^2$, 0.295 mm$^2$, 0.30 mm$^2$, or any other suitable cross-sectional area. In some embodiments, the cross-sectional area of the at least one tissue anchoring leg may be larger than the cross-sectional areas of more than one strut. In some embodiments, the cross-sectional areas of at least two, at least three, at least four, or at least five tissue anchoring legs may be larger than the cross-sectional area of a strut. Advantageously, configuring the cross-sectional area of the at least one tissue anchoring leg to be at least 20% larger than the cross-sectional area of the strut extending between the at least one tissue anchoring leg and the adjacent tissue anchoring leg may enhance the force exerted upon tissue by the at least one tissue anchor leg, while also permitting the strut to remain sufficiently flexible to easily transition between radially-contracted and radially-expanded configurations of the valve body. For example, FIG. 3C depicts the cross-sectional area 3624 of tissue anchoring legs 2240 and the cross-sectional area 3610 of outer frame atrial circumferential strut 3608*a*. Cross-sectional area 3624 may be at least 20% larger than cross-sectional area 3610, in some embodiments.

In some exemplary embodiments, the cross-sectional area of the at least one tissue anchoring leg may be perpendicular to a direction of extension of the at least one tissue anchoring leg. That is, the cross-sectional area of the at least one tissue anchoring leg may be perpendicular to the portion of the tissue anchoring leg in which it is located. Similarly, in some exemplary embodiments, the cross-sectional area of the strut extending between the at least one tissue anchoring leg and the adjacent tissue anchoring leg may be perpendicular to a direction of extension of the strut. That is, the cross-sectional area of the strut may be perpendicular to the portion of the strut in which it is located.

In some embodiments, the cross-sectional area of the at least one tissue anchoring leg may be at least twice as large as the cross-sectional area of the strut, at least three times as large as the cross-sectional area of the strut, at least four times as large as the cross-sectional area of the strut, at least five times as large as the cross-sectional area of the strut, or any other suitable size relative to the cross-sectional area of the strut.

In some embodiments, the at least one tissue anchoring leg may be configured to extend from the valve body, and, in particular, from a junction within the intermediate portion of the valve body. In some embodiments, at least a portion of the at least one tissue anchoring leg may be configured to extend radially outward from the location of connection between the at least one tissue anchoring leg and the valve body. In some exemplary embodiments, the entire length of the at least one tissue anchoring leg may be configured to extend radially outward from the location of connection between the at least one tissue anchoring leg and the valve body. For example, in FIGS. 5B and 5D, tissue anchoring legs 2240 extend radially outward from leg attachment junctions 3802 of valve body 2020. In some alternative embodiments, at least a portion of the at least one tissue anchoring leg may be configured to extend radially inward from the location of connection between the at least one tissue anchoring leg and the valve body.

In some embodiments, at least a portion of the at least one tissue anchoring leg may be configured to extend in an atrial direction, that is, in a direction extending towards an atrium of the heart, relative to the valve body. For example, the entire length of the at least one tissue anchoring leg may be configured to extend in an atrial direction. In some alternative embodiments, at least a portion of the at least one tissue anchoring leg may be configured to extend in a ventricular direction, that is, in a direction extending towards a ventricle of the heart, relative to the valve body. In some exemplary embodiments, at least a portion of the at least one tissue anchoring leg may be configured to extend in a non-ventricular direction, or in a direction that does not extend towards a ventricle of the heart, relative to the valve body. In some embodiments, the entire length of the at least one tissue anchoring leg may be configured to extend in a non-atrial direction, relative to the valve body. For example, in FIGS. 5B, 5D, and 5E, tissue anchoring legs 2240 extend radially outward from leg attachment junctions 3802 of valve body 2020. In some embodiments, tissue anchoring legs may be radially contracted and, thus, may not be configured to extend radially outward from the valve body. In some further embodiments, contracted tissue anchoring legs may be configured to extend in an atrial direction. For example, in FIG. 5A, contracted tissue anchoring legs 2240 extend in an atrial direction.

In some embodiments, the at least one tissue anchoring leg may be configured to engage ventricular tissue of a native mitral valve to anchor the prosthetic valve. In some embodiments, the at least one tissue anchoring leg may be configured to be positioned at least partially within a ventricle upon implantation of the prosthetic valve, and to engage ventricular tissue of the native mitral valve. For example, FIGS. 10F-10H depict tissue anchoring legs 2240 situated within ventricle 9020 and engaging the ventricular side of native mitral valve 9030. In some embodiments, the at least one tissue anchoring leg may be configured to minimize or prevent migration of the prosthetic valve, including preventing migration of the prosthetic valve in an atrial direction. In some embodiments, the at least one tissue anchoring leg may be configured to grasp or clamp tissue of the native mitral valve to further anchor the prosthetic valve in place. Optionally, the at least one tissue anchoring leg may include an anchoring feature to couple the leg to surrounding tissue. In some embodiments, at least two, at least three, at least four, or at least five tissue anchoring legs may be configured to engage ventricular tissue of a native mitral valve.

In some embodiments, the prosthetic valve may include one or a plurality of atrial tissue anchoring arms configured to engage atrial tissue of the native mitral valve to anchor the prosthetic valve therein. In some embodiments, the atrial tissue anchoring arms may extend from the intermediate portion of the valve body, such as from junctions within the intermediate portion of the valve body. For example, atrial tissue anchoring arms 1440 extend from intermediate portion 1026 of valve body 1020. Alternatively, one or more of the atrial tissue anchoring arms may extend from the atrial end of the valve body or from the ventricular end of the valve body. In some exemplary embodiments, the atrial tissue anchoring arms may be physically connected to the junctions, such as by welding or adhesive. In alternative embodiments, the atrial tissue anchoring arms and junctions may be manufactured as a single unitary structure. In some embodiments, at least a portion of some or all of the atrial tissue anchoring arms may be configured to extend radially outward from junctions within the intermediate portion of the valve body (that is, from locations of connection between the atrial tissue anchoring arms and the valve body). For example, the entire length of some or all of the atrial tissue anchoring arms may be configured to extend radially outward from junctions within the intermediate portion of the valve body. For example, in FIG. 5A, when atrial tissue anchoring arms 2440 are radially contracted, the atrial tissue anchoring arms 2440 extend straight upward in an atrial direction rather than extending radially outward. In FIG. 5C, portions of atrial tissue anchoring arms 2440 extend radially outward while the remainders of the atrial tissue anchoring arms 2440 extend straight upward in an atrial direction. In FIG. 5E, when atrial tissue anchoring arms 2440 are radially expanded, the entire lengths of the atrial tissue anchoring arms 2440 extend radially outward. In some alternative embodiments, at least a portion of some or all of the atrial tissue anchoring arms may be configured to extend radially inward from junctions within the intermediate portion of the valve body.

In some embodiments, at least a portion of at least one of the atrial tissue anchoring arms may be configured to extend in an atrial direction from the valve body. For example, a first portion of the at least one atrial tissue anchoring arm may be configured to extend in an atrial direction and a second portion of the at least one atrial tissue anchoring arm may be configured to extend in a ventricular direction. For example, in FIG. 5A, when atrial tissue anchoring arms 2440 are radially contracted, the entire lengths of each of the atrial tissue anchoring arms 2440 extend in an atrial direction. In FIG. 5C, when atrial tissue anchoring arms 2440 are radially expanded, some portions of the atrial tissue anchoring arms 2440 extend in an atrial direction, e.g., proximal arm portion 3502 and distal arm portion 3506, while other portions of the atrial tissue anchoring arms 2440 extend in a ventricular direction, e.g., arm portion 3504. In some alternative embodiments, the entire length of the at least one atrial tissue anchoring arm may be configured to extend in an atrial direction from the valve body or in a ventricular direction from the valve body.

In some embodiments, the locations of connection between the atrial tissue anchoring arms and valve body may be spaced at a regular interval about a circumference of the valve body. For example, in FIG. 2A, the atrial anchoring arms 2440 may extend from the annular valve body 2020 at arm attachment junctions 3202. Arm attachment junctions 3202 may be spaced at a regular interval about the circumference of annular valve body 2020. Additionally, or alternatively, the locations of connection between the atrial tissue anchoring arms and valve body may be arranged along a plane perpendicular to the longitudinal axis of the prosthetic valve. For example, in FIG. 2A, the arm attachment junctions 3202 may be arranged along a plane perpendicular to longitudinal axis 2800. That is, the arm attachment junctions 3202 may be situated at the same axial position along longitudinal axis 2800.

In some embodiments, the at least one atrial tissue anchoring arm may be configured to extend radially outward beyond the terminal end of the at least one tissue anchoring leg (that is, the end of the at least one tissue anchoring leg free from connection with the valve body). Said another way, a circumference formed by the terminal ends of the atrial tissue anchoring arms may have a larger diameter than a circumference formed by the terminal ends of the plurality of tissue anchoring legs. For example, in FIG. 2C, terminal arm end 2444 of tissue anchoring arm 2440 is positioned radially outward relative to terminal leg end 2244 of tissue anchoring leg 2240. In FIG. 5E, when valve body 2020 is radially expanded, terminal arm ends 2444 of tissue anchoring arms 2440 extend radially outward past terminal leg ends 2244 of tissue anchoring legs 2240. In FIG. 5A, when valve body 2020 is radially contracted, terminal arm ends 2444 of tissue anchoring arms 2440 do not extend past terminal leg ends 2244 of tissue anchoring legs 2240, but, rather, may be positioned radially inwards relative to terminal leg ends 2244 of tissue anchoring legs 2240.

In some embodiments, a width, or thickness, of a radial outer surface of the at least one tissue anchoring leg may be larger than a width of a radial outer surface of the strut extending between the at least one tissue anchoring leg and the adjacent tissue anchoring leg. A radial outer surface may refer to a surface facing away from the lumen of the valve body. For example, FIG. 3C depicts strut width 3612 of outer frame atrial circumferential strut 3608a and tissue anchoring leg width 3626 of tissue anchoring leg 2240. In some embodiments, width 3626 of tissue anchoring leg 2240 may be at least twice as large as width 3612 of outer frame atrial circumferential strut 3608a. Additionally or alternatively, a width of a radial inner surface of the at least one tissue anchoring leg may be larger than a width of a radial inner surface of the strut. In some exemplary embodiments, the width of the radial outer surface of the at least one tissue anchoring leg may be at least twice as large as the width of the radial outer surface of the strut. Alternatively, the width of the radial outer surface of the at least one tissue anchoring leg may be at least three times as large, at least four times as large, or at least five times as large as the width of the radial outer surface of the strut. In some embodiments, the radial outer surface of the at least one tissue anchoring leg may have a width of between 0.6 mm and 1.0 mm. For example, and without limitation, the radial outer surface of the at least one tissue anchoring leg may have a width of 0.6 mm, 0.65 mm, 0.7 mm, 0.75 mm, 0.76 mm, 0.77 mm, 0.78 mm, 0.79 mm, 0.8 mm, 0.81 mm, 0.82 mm, 0.83 mm, 0.84 mm, 0.85 mm, 0.9 mm, 0.95 mm, 1.0 mm, or any other suitable width. Additionally, or alternatively, the radial outer surface of the strut extending between the at least one tissue anchoring leg and the adjacent tissue anchoring leg may have a width of between 0.15 mm and 0.35 mm. For example, and without limitation, the radial outer surface of the strut extending between the at least one tissue anchoring leg and the adjacent tissue anchoring leg may have a width of 0.15 mm, 0.16 mm, 0.17 mm, 0.18 mm, 0.19 mm, 0.20 mm, 0.21 mm, 0.22 mm, 0.23 mm, 0.235 mm, 0.24 mm, 0.245 mm, 0.25 mm, 0.255 mm, 0.26 mm, 0.265 mm, 0.27 mm, 0.28 mm, 0.29 mm, 0.30 mm, 0.31 mm, 0.32 mm, 0.33 mm, 0.34 mm, 0.35 mm, or any other suitable width. In some embodiments, the width of the radial outer surface of the at least one tissue anchoring leg may be larger than the widths of more than one strut extending between the at least one tissue anchoring leg and the adjacent tissue anchoring leg. Advantageously, configuring the width of the at least one tissue anchoring leg to be at least twice as large as the width of the strut extending between the at least one tissue anchoring leg and the adjacent tissue anchoring leg may enhance the force exerted upon tissue by the at least one tissue anchor leg, while also permitting the strut to remain sufficiently flexible to easily transition between radially-contracted and radially-expanded configurations of the valve body.

In some embodiments, the prosthetic valve may include a tissue anchoring leg base strut extending between the junction from which the at least one tissue anchoring leg extends and the ventricular end of the valve body. In some embodiments, the tissue anchoring leg base strut may extend the entire distance between the junction from which the at least one tissue anchoring leg extends and the ventricular end of the valve body. For example, FIG. 3C depicts outer frame leg base strut 3608b extending between ventricular end outer frame junction 3604 and leg attachment junction 3802, from which tissue anchoring leg 2240 extends. The tissue anchoring leg base strut may be parallel to at least a portion of the at least one tissue anchoring leg. In some exemplary embodiments, the tissue anchoring leg base strut may have a cross-sectional area, which may refer to the two-dimensional area of a cross-sectional portion of the tissue anchoring leg base strut which is perpendicular to the portion of the tissue anchoring leg base strut in which it is located. For example, FIG. 3C depicts the cross-sectional area 3614 of outer frame leg base strut 3608b. In some embodiments, the cross-sectional area of the tissue anchoring leg base strut may be substantially equal to the cross-sectional area of the tissue anchoring leg. In some alternative embodiments, the cross-sectional area of the tissue anchoring leg base strut may be greater than or less than the cross-sectional area of the tissue anchoring leg. In some embodiments, the tissue anchoring leg base strut may have a cross-sectional area between 0.45 mm$^2$ and 0.65 mm$^2$. For example, and without limitation, the tissue anchoring leg base strut may have a cross-sectional area of 0.45 mm$^2$, 0.46 mm$^2$, 0.47 mm$^2$, 0.48 mm$^2$, 0.49 mm$^2$, 0.50 mm$^2$, 0.51 mm$^2$, 0.52 mm$^2$, 0.53 mm$^2$, 0.54 mm², 0.55 mm², 0.56 mm², 0.57 mm², 0.58 mm², 0.59 mm², 0.60 mm², 0.61 mm², 0.62 mm², 0.63 mm², 0.64 mm², 0.65 mm², or any other suitable cross-sectional area.

In some exemplary embodiments, the cross-sectional area of the at least one tissue anchoring leg may be situated within an inner radial half of the at least one tissue anchoring leg. For example, FIG. 3C depicts cross-sectional area 3624 at an inner radial half of tissue anchoring leg 2240. In some embodiments, the entire length of the inner radial half of the at least one tissue anchoring leg may have an equal cross-sectional area. For example, FIG. 3C depicts a constant cross-sectional area 3624 at an inner radial half of tissue anchoring leg 2240. In some alternative embodiments, different portions of the inner radial half may have different cross-sectional areas. In some embodiments, at least a portion of the outer radial half of the at least one tissue anchoring arm may have a cross-sectional area equal to the cross-sectional area of at least a portion of the inner radial half of the at least one tissue anchoring leg.

In some embodiments, the prosthetic valve may include a second strut extending between the at least one tissue anchoring leg and the adjacent tissue anchoring leg. In some embodiments, the second strut may partly extend between the at least one tissue anchoring leg and the adjacent tissue anchoring leg. In some exemplary embodiments, the second strut may extend for half the distance between the at least one tissue anchoring leg and the adjacent tissue anchoring leg. For example, in FIG. 3C, two adjacent outer frame atrial circumferential struts 3608a may intersect at an atrial end outer frame junction 3602 and may constitute a first strut and a second strut. The two adjacent outer frame atrial circumferential struts 3608a (i.e., the first strut and the second strut), considered together, may extend the distance between the two adjoining tissue anchoring legs 2240. In some alternative embodiments, the second strut may fully extend between the at least one tissue anchoring leg and the adjacent tissue anchoring leg. In some embodiments, the exemplary first and second struts may intersect at a junction that may be offset, relative to the longitudinal axis of the valve body, from the leg attachment location from which the at least one tissue anchoring leg extends. In some embodiments, the junction at which the exemplary first and second struts intersect may be situated in an axial direction relative to the leg attachment location from which the at least one tissue anchoring leg extends. For example, as depicted in FIG. 3C, exemplary first and second outer frame atrial circumferential struts 3608a may intersect at atrial end outer frame junction 3602. Atrial end outer frame junction 3602 may be situated in an axial direction relative to leg attachment junction 3802, from which tissue anchoring leg 2240 extends.

In some embodiments, at least a portion of the at least one tissue anchoring leg may be configured to be situated in an axial direction relative to the atrial end of the valve body. For example, the terminal end of the at least one tissue anchoring leg may be configured to be situated in an axial direction relative to the atrial end of the valve body. In some embodiments, the terminal end of the at least one tissue anchoring leg may be situated in an axial direction relative to the atrial end of the valve body when the prosthetic valve is arranged in a radially-contracted configuration. For example, in FIG. 5A, terminal leg ends 2244 of tissue anchoring legs 2240 are situated in an axial direction when prosthetic valve 2000 is radially contracted. Additionally, or alternatively, the terminal end of the at least one tissue anchoring leg may be situated in an axial direction relative to the atrial end of the valve body when the prosthetic valve is arranged in a radially-expanded configuration. For example, in FIG. 5E, terminal leg ends 2244 of tissue anchoring legs 2240 are situated in a radial direction when prosthetic valve 2000 is radially expanded. Additionally, or alternatively, the terminal end of the at least one tissue anchoring leg may be situated in an axial direction relative to the atrial end of the prosthetic valve when the prosthetic valve is arranged in a radially-contracted configuration and the at least one tissue anchoring leg is arranged in a radially-expanded configuration. For example, in FIG. 5B, terminal leg ends 2244 of tissue anchoring legs 2240 are situated in an axial direction when prosthetic valve 2000 is radially contracted and tissue anchoring legs 2240 are radially expanded. In some embodiments, at least another portion of the at least one tissue anchoring leg may also be configured to be situated in an axial direction relative to the atrial end of the valve body.

In some embodiments, the at least one tissue anchoring leg and the adjacent tissue anchoring leg may connect to separate portions of the valve body. That is, in some exemplary embodiments, the at least one tissue anchoring leg and the adjacent tissue anchoring leg may not connect to the valve body at a common point of connection. For example, in FIGS. 5A-5E, tissue anchoring legs 2240 connect to valve body 2020 at separate leg attachment junctions 3802. In some embodiments, the location of connection of the at least one tissue anchoring leg to the valve body may be even with the location of connection of the adjacent tissue anchoring leg to the valve body, relative to the longitudinal axis of the valve body. That is, the location of connection of the at least one tissue anchoring leg and the location of connection of the adjacent tissue anchoring leg may be equidistant from the atrial end of the valve body and from the ventricular end of the valve body. For example, in FIGS. 5A-5E, tissue anchoring legs 2240 connect to valve body 2020 at leg attachment junctions 3802 equidistant from atrial and ventricular ends of the valve body. In some alternative embodiments, the location of connection of the at least one tissue anchoring leg may be situated in an atrial direction or in a ventricular direction relative to the location of connection of the adjacent tissue anchoring leg.

In some embodiments, the at least one tissue anchoring leg may extend from a single portion of the valve body. That is, the at least one tissue anchoring leg may have a single location of connection to the valve body. In some exemplary embodiments, the at least one tissue anchoring leg may extend from a single junction of the valve body. For example, in FIG. 3C, tissue anchoring leg 2240 connects to valve body 2020 (specifically, to outer frame tubular portion 3605) at a single leg attachment junction 3802. In some embodiments, the at least one tissue anchoring leg may be physically connected to the leg attachment junction, such as by welding or adhesive. In alternative embodiments, the at least one tissue anchoring leg and the leg attachment junction may be manufactured as a single unitary structure. Additionally, or alternatively, the adjacent tissue anchoring leg may have a single location of connection to the valve body and may extend from a different leg attachment junction of the valve body. In some alternative embodiments, the at least one tissue anchoring leg may be configured to extend from multiple portions of the valve body, such as from two or more junctions of the valve body.

In some embodiments, at least a portion of the at least one tissue anchoring leg may be configured to extend radially outward from the valve body when the prosthetic valve is implanted at the native mitral valve. For example, in some embodiments, the entire length of the at least one tissue anchoring leg may be configured to extend radially outward from the valve body, and, in particular, from a point of connection of the at least one tissue anchoring leg to the valve body. For example, in FIG. 5E, tissue anchoring leg 2240 extends radially outward from valve body 2020 at leg attachment junction 3802. In some alternative embodiments, at least a portion of the at least one tissue anchoring leg may be configured to extend radially inward from the valve body upon implantation of the prosthetic valve. Additionally, or alternatively, at least a portion of the at least one tissue anchoring leg may be configured to extend in an atrial direction (that is, towards the left atrium) when the prosthetic valve is implanted at the native mitral valve. For example, in some embodiments, the entire length of the at least one tissue anchoring leg may be configured to extend in an atrial direction (that is, towards the left atrium) from the valve body, and, in particular, from a point of connection of the at least one tissue anchoring leg to the valve body. For example, in FIG. 5A, tissue anchoring leg 2240 extends in an atrial direction from valve body 2020 at leg attachment junction 3802. In some alternative embodiments, at least a portion of the at least one tissue anchoring leg may be configured to extend in a ventricular direction (that is, towards the left ventricle) upon implantation of the prosthetic valve. The entire length of the at least one tissue anchoring leg may refer to the length that extends between the end of the tissue anchoring leg that connects to a valve body and the opposite, terminal end of the at least one tissue anchoring leg which is furthest from or most distal to the point of connection of the leg to the valve body.

In some alternative embodiments of the present disclosure, an expandable prosthetic valve configured for implantation within a native heart valve, such as a native mitral valve, may be provided. The exemplary prosthetic valve may include one or more frames. In some embodiments, the prosthetic valve may include an outer frame and an inner frame situated at least partially within the outer frame. In some embodiments, one or both of the inner frame and the outer frame may be annular, and the inner frame may be positioned within an opening of the outer frame. For example, FIG. 2A depicts outer frame 2200 and inner frame 2400. One or both of the inner frame and the outer frame may be configured to radially expand between a radially-contracted configuration and a radially-expanded configuration. For example, in some embodiments the inner frame and outer frame may be configured to radially expand between their respective radially-contracted and radially-expanded configurations in concert; this may be due, at least in part, to a mechanical connection between the inner and outer frames. In some embodiments, the inner frame may be configured to receive or otherwise support a flow control device, such as one or more leaflets, for regulating flow of blood or other bodily fluids through the prosthetic valve. For example, FIGS. 6D and 6E depict leaflets 6602, 6604, and 6606 within an inner frame. As a result, when the prosthetic valve is implanted within a native valve (e.g., a mitral valve), the flow control device may regulate fluid passage through the native valve, thus restoring and/or replacing the functionality of the native valve. The inner frame may include a plurality of struts intersecting at junctions to form one or more closed cells of the inner frame. The closed cells of the inner frame may be diamond-shaped, chevron-shaped, rectangular, triangular, circular, or may have any other suitable shape. The inner frame may include closed cells of the same shape or closed cells having different shapes. Similarly, the outer frame may include a plurality of struts intersecting at junctions to form one or more closed cells of the outer frame. The closed cells of the outer frame may be diamond-shaped, chevron-shaped, rectangular, triangular, circular, or may have any other suitable shape. The outer frame may include closed cells of the same shape or closed cells having different shapes. In some embodiments, the closed cells of the inner frame may have the same shape as the closed cells of the outer frame. Alternatively, the closed cells of the inner frame may have a different shape than the closed cells of the outer frame. For example, FIG. 3A depicts cells 3012 and 3014 of inner frame 2400 and FIG. 3C depicts cells 3616 of outer frame 2200.

In some embodiments, the annular outer frame may include one or more ventricular tissue anchoring legs configured to engage ventricular tissue of the native mitral valve to anchor the expandable prosthetic valve therein. For example, FIGS. 10E-10H depict ventricular tissue anchoring legs 2240 situated within ventricle 9020 and engaging the ventricular side of native mitral valve 9030. In some embodiments, the ventricular tissue anchoring legs may be configured to be positioned at least partially within a ventricle upon implantation of the prosthetic valve, and to engage ventricular tissue of a native mitral valve. In some embodiments, the ventricular tissue anchoring legs may be configured to minimize or prevent migration of the prosthetic valve, including minimizing or preventing migration of the prosthetic valve in an atrial direction, due to the engagement of the legs with mitral valve tissue. In some embodiments, the ventricular tissue anchoring legs may have a larger diameter than the orifice of the native mitral valve when the prosthetic valve is implanted, such that the ventricular tissue anchoring legs may be prevented from passing through the orifice of the mitral valve. Additionally, or alternatively, the ventricular tissue anchoring legs may be configured to grasp tissue of the native valve to further anchor the prosthetic valve in place. Optionally, one or more of the ventricular tissue anchoring legs may include an anchoring feature to couple the legs to surrounding tissue.

In some embodiments, the ventricular tissue anchoring legs may extend from leg attachment junctions or other junctions of the annular outer frame. For example, in FIG. 3C, tissue anchoring legs 2240 extend from leg attachment junctions 3802 of outer frame 2200. The ventricular tissue anchoring legs may be physically connected to the leg attachment junctions or other junctions of the annular outer frame, such as by welding or adhesive. Alternatively, the ventricular tissue anchoring legs and the leg attachment junctions or other and junctions may be manufactured as a single unitary structure. In some embodiments, at least a portion of one or more ventricular tissue anchoring legs may be configured to extend radially outward from the leg attachment junctions or other junctions of the annular outer frame, and, in particular, from the points of connection between the one or more ventricular tissue anchoring legs and the leg attachment junctions or other junctions of the annular outer frame. In some embodiments, the entire length of one or more ventricular tissue anchoring legs may be configured to extend radially outward from the leg attachment junctions or other junctions of the annular outer frame, and, in particular, from the points of connection between the one or more ventricular tissue anchoring legs and the leg attachment junctions or other junctions of the annular outer frame. In some alternative embodiments, at least a portion of one or more ventricular tissue anchoring legs may be configured to extend radially inward from the leg attachment junctions or other junctions of the annular outer frame. For example, in FIG. 5A, when tissue anchoring legs 2240 are radially contracted, tissue anchoring legs 2240 extend in an atrial direction from leg attachment junctions 3802 to which they are connected rather than extending radially outward. In FIGS. 5B and 5D, when tissue anchoring legs 2240 are radially expanded but valve body 2020 is radially contracted and, in FIG. 5E, when prosthetic valve 2000 is radially expanded, at least portions of and, in some cases, entire lengths of tissue anchoring legs 2240 extend radially outward from the leg attachment junctions 3802.

In some embodiments, the inner frame may include one or a plurality of atrial tissue anchoring arms configured to engage atrial tissue of the native mitral valve to anchor the expandable prosthetic valve therein. For example, FIGS. 10F-10H depict atrial anchoring arms 2440 situated within atrium 9010 and engaging the atrial side of native mitral valve 9030. In some embodiments, the atrial tissue anchoring arms may be configured to be positioned at least partially within an atrium upon implantation of the prosthetic valve, and to engage atrial tissue of a native mitral valve. In some embodiments, the atrial tissue anchoring arms may be configured to minimize or prevent migration of the prosthetic valve, including minimizing or preventing migration of the prosthetic valve in a ventricular direction, due to the engagement of the arms with mitral valve tissue. In some embodiments, the ventricular tissue anchoring legs may have a larger diameter than the orifice of the native mitral valve when the prosthetic valve is implanted, such that the ventricular tissue anchoring legs may be prevented from passing through the orifice of the mitral valve. Additionally, or alternatively, the atrial tissue anchoring arms may be configured to grasp tissue of the native valve to further anchor the prosthetic valve in place. Optionally, one or more of the atrial tissue anchoring arms may include an anchoring feature to couple the arms to surrounding tissue.

In some embodiments, the atrial tissue anchoring arms may extend from arm attachment junctions of the inner frame. For example, in FIGS. 5A-5E, tissue anchoring arms 2440 extend from arm attachment junctions 3202, which may be situated within inner frame tubular portion 3005. The atrial tissue anchoring arms may be physically connected to the arm attachment junctions of the inner frame, such as by welding or adhesive. Alternatively, the atrial tissue anchoring arms and the arm attachment junctions may be manufactured as a single unitary structure. In some embodiments, at least a portion of one or more atrial tissue anchoring arms may be configured to extend radially outward from the arm attachment junctions of the inner frame, and in particular, from the points of connection between the one or more atrial tissue anchoring arms and the arm attachment junctions of the inner frame. In some embodiments, the entire length of one or more atrial tissue anchoring arms may be configured to extend radially outward from the arm attachment junctions of the inner frame, and, in particular, from the points of connection between the one or more atrial tissue anchoring arms and the arm attachment junctions of the inner frame. In some alternative embodiments, at least a portion of one or more atrial tissue anchoring arms may be configured to extend radially inward from the arm attachment junctions of the inner frame. For example, in FIG. 5A, when tissue anchoring arms 2440 are radially contracted, tissue anchoring arms 2440 extend in an atrial direction from arm attachment junctions 3202 to which they are connected, rather than extending radially outward. In FIGS. 5C and 5D, when tissue anchoring arms 2440 are radially expanded but valve body 2020 is radially contracted and, in FIG. 5E, when prosthetic valve 2000 is radially expanded, at least portions of and, in some cases, entire lengths of tissue anchoring arms 2440 extend radially outward from the arm attachment junctions 3202.

In some alternative embodiments, the annular outer frame may include one or more of the atrial tissue anchoring arms and the inner frame may include one or more of the ventricular tissue anchoring legs. In some further alternative embodiments, one or both of the inner frame and the annular outer frame may include at least one ventricular tissue anchoring leg and at least one atrial tissue anchoring arm.

In some embodiments, the exemplary prosthetic valve may include equal numbers of atrial tissue anchoring arms and ventricular tissue anchoring legs. For example, exemplary prosthetic valve 6000 illustrated in FIGS. 2A and 2B includes twelve atrial anchoring arms 2440 and twelve ventricular anchoring legs 2240. Alternatively, the exemplary prosthetic valve may include more atrial tissue anchoring arms than ventricular tissue anchoring legs. As a further alternative, the exemplary prosthetic valve may include fewer atrial tissue anchoring arms than ventricular tissue anchoring legs.

In some embodiments, at least one of the ventricular tissue anchoring legs may have a cross-sectional area. A cross-sectional area may refer to the two-dimensional area of a cross-sectional portion of the ventricular tissue anchoring leg which is perpendicular to the ventricular tissue anchoring leg. For example, as depicted in FIG. 3C, ventricular tissue anchoring leg 2240 may have a cross-sectional area 3624 which is perpendicular to the portion of the ventricular tissue anchoring leg 2240 in which it is located. In some embodiments, the at least one ventricular tissue anchoring leg may have a constant cross-sectional area along at least a portion of its length or along its entire length. The term entire length may refer to the portion of the tissue anchoring leg extending between a point of connection with a valve body and a terminal end of the tissue anchoring leg. In some alternative embodiments, the at least one ventricular tissue anchoring leg may have a variable cross-sectional area along its length. In some further embodiments, the at least one ventricular tissue anchoring leg may have a constant cross-sectional area along a certain portion of its length and a variable cross-sectional area along the remainder of its length. For example, in FIGS. 3C-3D, tissue anchoring legs 2240 exhibit a constant cross-sectional area between leg attachment junction 3802 and opening 2242. The cross-sectional area of the tissue anchoring legs 2240 decreases at opening 2242. In some embodiments, a plurality of tissue anchoring legs in the valve body may have equal cross-sectional areas. In some alternative embodiments, at least one tissue anchoring leg may have a different cross-sectional area relative to the cross-sectional areas of other tissue anchoring legs.

In some embodiments, the prosthetic valve may include a strut of the outer frame extending between the at least one ventricular tissue anchoring leg and an adjacent ventricular tissue anchoring leg (that is, the nearest of the other ventricular tissue anchoring legs). In some embodiments, the strut of the outer frame may partly extend between the at least one ventricular tissue anchoring leg and the adjacent ventricular tissue anchoring leg. For example, at least one additional strut of the outer frame may be situated between the strut of the outer frame and the at least one ventricular tissue anchoring leg and/or between the strut of the outer frame and the adjacent ventricular tissue anchoring leg. In some exemplary embodiments, the strut of the outer frame may extend for substantially half the distance between the at least one ventricular tissue anchoring leg and the adjacent ventricular tissue anchoring leg. For example, outer frame atrial circumferential strut 3608a, in FIG. 3C, extends for half the distance between adjacent ventricular tissue anchoring legs (specifically, outer frame atrial circumferential strut 3608a extends between leg attachment junction 3802 and atrial end outer frame junction 3602). In some alternative embodiments, the strut of the outer frame may fully extend between the at least one ventricular tissue anchoring leg and the adjacent ventricular tissue anchoring leg. In some embodiments, the strut of the outer frame may extend from, or be physically connected to, one or more of the at least one ventricular tissue anchoring leg and the adjacent ventricular tissue anchoring leg.

In some embodiments, the strut of the outer frame extending between the at least one ventricular tissue anchoring leg and the adjacent ventricular tissue anchoring leg may have a cross-sectional area. The cross-sectional area may be the two-dimensional area of a cross-sectional portion of the strut of the outer frame which is perpendicular to the strut of the outer frame. For example, as depicted on FIG. 3C, outer frame atrial circumferential strut 3608a may have a cross-sectional area 3610 that is perpendicular to the portion of the strut of the outer frame in which it is located. In some embodiments, the strut of the outer frame may have a constant cross-sectional area along its entire length. In some alternative embodiments, the strut of the outer frame may have a variable cross-sectional area along its entire length. In some further alternative embodiments, the strut of the outer frame may have a constant cross-sectional area along a certain portion of its length and a variable cross-sectional area along the remainder of its length.

In some embodiments, the cross-sectional areas of the at least one ventricular tissue anchoring leg and the strut of the outer frame extending between the at least one ventricular tissue anchoring leg and the adjacent ventricular tissue anchoring leg may be substantially equal. In some alternative embodiments, the cross-sectional area of the at least one ventricular tissue anchoring leg may be at least 10% larger than the cross-sectional area of the strut of the outer frame. In some further embodiments, the cross-sectional area of the at least one ventricular tissue anchoring leg may be at least 20% larger, at least 30% larger, at least 40% larger, or at least 50% larger than the cross-sectional area of the strut of the outer frame. In some embodiments, the cross-sectional area of the at least one ventricular tissue anchoring leg may be larger than that of more than one strut of the outer frame. In some embodiments, the cross-sectional areas of at least two, at least three, at least four, or at least five ventricular tissue anchoring legs may be larger than that of a strut. For example, FIG. 3C depicts the cross-sectional area 3624 of tissue anchoring legs 2240 and the cross-sectional area 3610 of outer frame atrial circumferential strut 3608a.

In some embodiments, at least one of the atrial tissue anchoring arms may have a cross-sectional area. A cross-sectional area may refer to the two-dimensional area of a cross-sectional portion of the atrial tissue anchoring arm which is perpendicular to the atrial tissue anchoring arm. For example, as depicted in FIG. 3A, atrial tissue anchoring arm 2440 may have a cross-sectional area 3022 which is perpendicular to the portion of the atrial tissue anchoring arm 2440 in which it is located. In some embodiments, the at least one atrial tissue anchoring arm may have a constant cross-sectional area along at least a portion of its length or along its entire length. In some exemplary embodiments, the entire length of the tissue anchoring arm may refer to a portion of the tissue anchoring arm extending between a point of connection with a valve body and a terminal end of the tissue anchoring arm. In some embodiments, the at least one atrial tissue anchoring arm may have a variable cross-sectional area along its length. In some further embodiments, the at least one atrial tissue anchoring arm may have a constant cross-sectional area along a certain portion of its length and a variable cross-sectional area along the remainder of its length. For example, in FIG. 3B, tissue anchoring arm 2440 has a serpentine structure 3406 with a smaller cross-sectional area 3406c compared with a cross-sectional area 3402c of an inflexible portion of the tissue anchoring arm 3402.

In some embodiments, the inner frame may include a strut of the inner frame extending between the at least one atrial tissue anchoring arm and an adjacent atrial tissue anchoring arm (that is, the nearest of the other atrial tissue anchoring arms). In some embodiments, the strut of the inner frame may partly extend between the at least one atrial tissue anchoring arm and the adjacent atrial tissue anchoring arm. For example, at least one additional strut of the inner frame may be situated between the strut of the inner frame and the at least one atrial tissue anchoring arm and/or between the strut of the inner frame and the adjacent atrial tissue anchoring arm. In some exemplary embodiments, the strut of the inner frame may extend for substantially half the distance between the at least one atrial tissue anchoring arm and the adjacent atrial tissue anchoring arm. For example, an inner frame atrial strut 3008a, in FIG. 3A, extends for half the distance between adjacent atrial tissue anchoring arms 2440 (specifically, inner frame atrial strut 3008a extends between arm attachment junction 3202 and atrial end inner frame junction 3002). In some alternative embodiments, the strut of the inner frame may fully extend between the at least one atrial tissue anchoring arm and the adjacent atrial tissue anchoring arm. In some embodiments, the strut of the inner frame may extend from, or be physically connected to, one or more of the at least one atrial tissue anchoring arm and the adjacent atrial tissue anchoring arm.

In some embodiments, the strut of the inner frame extending between the at least one atrial tissue anchoring arm and the adjacent atrial tissue anchoring arm may have a cross-sectional area. The cross-sectional area may be the two-dimensional area of a cross-sectional portion of the strut of the inner frame which is perpendicular to the strut of the inner frame. For example, as depicted in FIG. 3A, inner frame atrial strut 3008a may have a cross-sectional area 3010 which is perpendicular to the portion of the inner frame atrial strut 3008a in which it is located. In some embodiments, the strut of the inner frame may have a constant cross-sectional area along its entire length. In some alternative embodiments, the strut of the inner frame may have a variable cross-sectional area along its entire length. In some further alternative embodiments, the strut of the inner frame may have a constant cross-sectional area along a certain portion of its length and a variable cross-sectional area along the remainder of its length.

In some embodiments, the cross-sectional areas of the at least one atrial tissue anchoring arm and the strut of the inner frame extending between the at least one atrial tissue anchoring arm and the adjacent atrial tissue anchoring arm may be substantially equal. In some alternative embodiments, the cross-sectional area of the at least one atrial tissue anchoring arm may be at least 10% larger than the cross-sectional area of the strut of the inner frame. In some further embodiments, the cross-sectional area of the at least one atrial tissue anchoring arm may be at least 20% larger, at least 30% larger, at least 40% larger, or at least 50% larger than the cross-sectional area of the strut of the inner frame. In some embodiments, the at least one atrial tissue anchoring arm may have a cross-sectional area between 0.25 $mm^2$ and 0.35 $mm^2$. For example, and without limitation, the at least one atrial tissue anchoring arm may have a cross-sectional area of 0.25 mm$^2$, 0.26 mm$^2$, 0.27 mm$^2$, 0.28 mm$^2$, 0.29 mm$^2$, 0.30 mm$^2$, 0.31 mm$^2$, 0.32 mm$^2$, 0.33 mm$^2$, 0.34 mm$^2$, 0.35 mm$^2$, or any other suitable cross-sectional area. Additionally, or alternatively, the strut of the inner frame extending between the at least one atrial tissue anchoring arm and the adjacent atrial tissue anchoring arm may have a cross-sectional area between 0.08 mm$^2$ and 0.15 mm$^2$. For example, and without limitation, the strut of the inner frame extending between the at least one atrial tissue anchoring arm and the adjacent atrial tissue anchoring arm may have a cross-sectional area of 0.08 mm$^2$, 0.085 mm$^2$, 0.09 mm$^2$, 0.095 mm$^2$, 0.10 mm$^2$, 0.105 mm$^2$, 0.11 mm$^2$, 0.115 mm$^2$, 0.12 mm$^2$, 0.121 mm$^2$, 0.122 mm$^2$, 0.123 mm$^2$, 0.124 mm$^2$, 0.125 mm$^2$, 0.126 mm$^2$, 0.127 mm$^2$, 0.128 mm$^2$, 0.129 mm$^2$, 0.13 mm$^2$, 0.135 mm$^2$, 0.14 mm$^2$, 0.145 mm$^2$, 0.15 mm$^2$, or any other suitable cross-sectional area. In some embodiments, the cross-sectional area of the at least one atrial tissue anchoring arm may be larger than the cross-sectional areas of more than one strut of the inner frame. In some embodiments, the cross-sectional areas of at least two, at least three, at least four, or at least five atrial tissue anchoring arms may be larger than the cross-sectional area of a strut. Advantageously, configuring the cross-sectional area of the at least one atrial tissue anchoring arm to be at least 20% larger than the cross-sectional area of the strut of the inner frame extending between the at least one atrial tissue anchoring arm and the adjacent atrial tissue anchoring arm may enhance the force exerted upon tissue by the at least one atrial tissue anchoring arm, while also permitting the strut to remain sufficiently flexible to easily transition between radially-contracted and radially-expanded configurations of the valve body. For example, FIG. 3A depicts the cross-sectional area 3022 of tissue anchoring arms 2440 and the cross-sectional area 3010 of inner frame atrial strut 3008*a*. In some embodiments, the cross-sectional area 3022 of tissue anchoring arms 2440 may be at least 20% larger than the cross-sectional area 3010 of inner frame atrial strut 3008*a*.

In some embodiments, at least one of the atrial tissue anchoring arms may have a cross-sectional area. The cross-sectional area may be the two-dimensional area of a cross-sectional portion of the atrial tissue anchoring arm which is perpendicular to the portion of the atrial tissue anchoring arm in which it is located. In some embodiments, the cross-sectional areas of the at least one atrial tissue anchoring arm and the strut of the outer frame extending between the at least one ventricular tissue anchoring leg and the adjacent ventricular tissue anchoring leg may be substantially equal. In some alternative embodiments, the cross-sectional area of the at least one atrial tissue anchoring arm may be at least 10% larger than the cross-sectional area of the strut of the outer frame. In some further embodiments, the cross-sectional area of the at least one atrial tissue anchoring arm may be at least 20% larger, at least 30% larger, at least 40% larger, or at least 50% larger than the cross-sectional area of the strut of the outer frame. For example, FIG. 3A depicts the cross-sectional area 3022 of tissue anchoring arms 2440 and FIG. 3C shows the cross-sectional area 3610 of outer frame atrial circumferential strut 3608*a*. In some embodiments, the cross-sectional area of the at least one atrial tissue anchoring arm may be larger than the cross-sectional areas of more than one strut of the outer frame.

In some embodiments, the annular outer frame and inner frame may each include respective atrial ends. In some embodiments, the atrial end may refer to respective portions of the annular outer frame and the inner frame configured to be situated at a location within an atrium (e.g., the left atrium) that is furthest from an adjacent ventricle (e.g., the left ventricle) when the prosthetic valve is implanted in a native heart valve. For example, as illustrated in FIGS. 5A-5E, atrial end inner frame junction 3002 of exemplary inner frame 2400 may be situated in an atrial direction (that is, further into the atrium) than atrial end outer frame junction 3602 exemplary annular outer frame 2200. In some embodiments, the atrial ends of the inner and outer frames may be even, with respect to the longitudinal axis of the valve body. That is, the atrial ends of the inner and outer frames may be situated within a plane perpendicular to the longitudinal axis of the valve body. In some alternative embodiments, the atrial end of the inner frame may be positioned in an atrial direction relative to the atrial end of the outer frame. In some further alternative embodiments, the atrial end of the inner frame may be positioned in a ventricular direction relative to the atrial end of the outer frame.

Additionally, or alternatively, the annular outer frame and inner frame may each include respective ventricular ends. In some embodiments, the ventricular end may refer to respective portions of the annular outer frame and the inner frame configured to be situated at a location within a ventricle (e.g., the left ventricle) that is furthest from an adjacent atrium (e.g., the left atrium) when the prosthetic valve is implanted in a native heart valve. In some embodiments, the ventricular ends of the inner and outer frames may be even, with respect to the longitudinal axis of the valve body. That is, the ventricular ends of the inner and outer frames may be situated within a common plane which is perpendicular to the longitudinal axis of the valve body. For example, as illustrated in FIGS. 5A-5E, ventricular end inner frame junction 3004 of exemplary inner frame 2400 may be even with ventricular end outer frame junction 3604 of exemplary annular outer frame 2200, with respect to longitudinal axis 2800. In some alternative embodiments, the ventricular end of the inner frame may be positioned in an atrial direction relative to the ventricular end of the outer frame. In some further alternative embodiments, the ventricular end of the inner frame may be positioned in a ventricular direction relative to the ventricular end of the outer frame.

In some embodiments, the annular outer frame and the inner frame may be secured together by at least one connection. In some embodiments, the annular outer frame and the inner frame may be secured together by known techniques, such as pins, screws, adhesive, welding, clips, or any other suitable connection. In various embodiments, the annular outer frame and the inner frame may be connected by one connection, two connections, three connections, four connections, five connections, six connections, seven connections, eight connections, nine connections, ten connections, eleven connections, twelve connections, thirteen connections, fourteen connections, fifteen connections, or any other suitable number of connections. For example, in FIG. 2A, outer frame 2200 and inner frame 2400 are connected to valve body 2020 by connectors 2040. In some embodiments, the at least one connection between the annular outer frame and the inner frame may be positioned away from the atrial ends of the annular outer frame and the inner frame. For example, the at least one connection may be situated within the intermediate portion of the inner frame or at the ventricular end of the inner frame. Similarly, the at least one connection may be situated within the intermediate portion of the annular outer frame or at the ventricular end of the annular outer frame. For example, in FIGS. 3A and 3C, connectors 2040 are situated within an intermediate portion 3006 of inner frame 2400 and an intermediate portion 3606 of outer frame 2200. In some embodiments, a plurality of connections between the annular outer frame and the inner frame may be positioned away from the atrial ends of the annular outer frame and the inner frame.

In some embodiments, at least one connection between the annular outer frame and the inner frame may be positioned in a ventricular direction relative to at least a portion of the at least one atrial tissue anchoring arm. For example, the at least one connection may be positioned in a ventricular direction relative to the entire length of the at least one atrial tissue anchoring arm, including the location at which the at least one atrial tissue anchoring arm is connected to the inner frame. For example, in FIG. 2A, tissue anchoring arms 2440 are connected to inner frame 2400 at connectors 2040 positioned in a ventricular direction. In some embodiments, a plurality of connections between the inner and outer frames may be positioned in a ventricular direction relative to a portion of or the entire length of the at least one atrial tissue anchoring arm and, in some embodiments, one or more additional atrial tissue anchoring arms. Additionally, or alternatively, the at least one connection between the annular outer frame and the inner frame may be positioned in a ventricular direction relative to at least a portion of the at least one ventricular tissue anchoring leg. For example, the at least one connection may be positioned in a ventricular direction relative to the entire length of the at least one ventricular tissue anchoring leg, including the location at which the at least one ventricular tissue anchoring leg is connected to the annular outer frame. For example, in FIG. 2A, tissue anchoring legs 2240 are connected to outer frame 2200 at connectors 2040 positioned in a ventricular direction. In some embodiments, a plurality of connections between the inner and outer frames may be positioned in a ventricular direction relative to a portion of or the entire length of the at least one ventricular tissue anchoring leg and, in some embodiments, one or more additional ventricular tissue anchoring legs.

In some further alternative embodiments of the present disclosure, a prosthetic valve configured for implantation within a native heart valve, such as a native mitral valve, may be provided. The prosthetic valve may be configured to radially expand between a radially-contracted configuration and a radially-expanded configuration. In some embodiments, the prosthetic valve may include an exemplary valve body. In some embodiments, the valve body may be configured to receive or otherwise support a flow control device, such as one or more leaflets, for regulating flow of blood or other bodily fluids through the prosthetic valve. For example, FIGS. 6D and 6E depict leaflets 6602, 6604, and 6606 within valve body 2020. As a result, when the prosthetic valve is implanted within a native valve (e.g., a mitral valve), the flow control device may regulate fluid passage through the native valve, thus restoring and/or replacing the functionality of the native valve. In some embodiments, the exemplary valve body may be annular or ring-shaped and may be configured to radially expand between a radially-contracted configuration and a radially-expanded configuration. In some embodiments, the exemplary valve body may include a plurality of struts intersecting at junctions to form a wire mesh, stent-like, or cage-like structure of the valve body. For example, FIG. 3A depicts inner frame atrial struts 3008a, inner frame intermediate struts 3008b, and inner frame ventricular struts 3008c intersecting at junctions 3204 in valve body 2020. In some embodiments, the struts of the valve body may be made of metals or alloys, such as Nitinol. In some embodiments, the struts of the valve body may be straight, curved, or may have at least one straight portion and at least one curved portion. In some embodiments, two struts may intersect at a junction of the valve body, three struts may intersect at a junction of the valve body, four struts may intersect at a junction of the valve body, five struts may intersect at a junction of the valve body, or any other suitable number of struts may intersect at a junction of the valve body.

In some embodiments, the exemplary prosthetic valve may include one or a plurality of tissue anchoring legs configured to anchor the prosthetic valve at an implantation site, such as within a native heart valve. In some embodiments, the tissue anchoring legs may be configured to engage tissue of a native heart valve, such as ventricular tissue of a native mitral valve, to anchor the prosthetic valve within the native heart valve. The prosthetic valve may include any suitable number of tissue anchoring legs. For example, exemplary prosthetic valve 6000 may include twelve tissue anchoring legs 2240. In some embodiments, the tissue anchoring legs may extend from junctions of the valve body. In some embodiments, the tissue anchoring legs may be physically connected to the junctions, such as by welding or adhesive. In alternative embodiments, the tissue anchoring legs and junctions may be manufactured as a single unitary structure.

In some embodiments, the prosthetic valve may include a first strut extending from at least one tissue anchoring leg towards an adjacent tissue anchoring leg (that is, the nearest of the other tissue anchoring legs). In some embodiments, the first strut may partly extend between the at least one tissue anchoring leg and the adjacent tissue anchoring leg. For example, at least one additional first strut may be situated between the first strut and the at least one tissue anchoring leg and/or between the first strut and the adjacent tissue anchoring leg. In some exemplary embodiments, the first strut may extend for substantially half the distance between the at least one tissue anchoring leg and the adjacent tissue anchoring leg. For example, outer frame atrial circumferential strut 3608a, in FIG. 3C, extends for half the distance between adjacent tissue anchoring legs (specifically, outer frame atrial circumferential strut 3608a extends between leg attachment junction 3802 and atrial end outer frame junction 3602). In some alternative embodiments, the first strut may fully extend between the at least one tissue anchoring leg and the adjacent tissue anchoring leg. In some embodiments, the first strut may extend from, or be physically connected to, one or more of the at least one tissue anchoring leg and the adjacent tissue anchoring leg.

In some embodiments, the at least one tissue anchoring leg may have a cross-sectional area. A cross-sectional area may refer to the two-dimensional area of a cross-sectional portion of the tissue anchoring leg which is perpendicular to the tissue anchoring leg. For example, as depicted on FIG. 3C, tissue anchoring leg 2240 may have a cross-sectional area 3624 which is perpendicular to the portion of the tissue anchoring leg 2240 in which it is located. In some embodiments, the cross-sectional areas of the at least one tissue anchoring leg and the first strut extending between the at least one tissue anchoring leg and the adjacent tissue anchoring leg may be substantially equal. In some alternative embodiments, the cross-sectional area of the at least one tissue anchoring leg may be at least 10% larger than the cross-sectional area of the first strut. In some further embodiments, the cross-sectional area of the at least one tissue anchoring leg may be at least 20% larger, at least 30% larger, at least 40% larger, or at least 50% larger than the cross-sectional area of the first strut. In some embodiments, the cross-sectional area of the at least one tissue anchoring leg may be larger than the cross-sectional areas of more than one first strut. In some embodiments, the cross-sectional areas of at least two, at least three, at least four, or at least five tissue anchoring legs may be larger than the cross-sectional area of a strut. For example, FIG. 3C depicts the cross-sectional area 3624 of tissue anchoring legs 2240 and the cross-sectional area 3610 of outer frame atrial circumferential strut 3608a.

In some embodiments, the at least one tissue anchoring leg and the adjacent tissue anchoring leg may be angularly separated by a single junction. That is, when considering the struts of the valve body which extend from the at least one tissue anchoring leg to the adjacent tissue anchoring leg, the struts form only a single junction. For example, in FIGS. 2A and 3C, two adjacent tissue anchoring legs 2440 may be separated by a pair of outer frame atrial circumferential struts 3608a, which may form a single atrial end outer frame junction 3602 between the two adjacent legs.

In some embodiments, the at least one tissue anchoring leg may include one or more openings therein. In some embodiments, the one or more openings may be situated in a radial outer half of the at least one tissue anchoring leg or, in some embodiments, at or near the terminal end of the at least one tissue anchoring leg. For example, in FIG. 3D, leg opening 2242 is situated at a leg end 2244 of tissue anchoring leg 2240.

In some embodiments, the valve body may include a second strut that extends from the adjacent tissue anchoring leg. For example, the second strut may extend from the adjacent tissue anchoring leg towards the at least one tissue anchoring leg. In some embodiments, the second strut may partly extend between the at least one tissue anchoring leg and the adjacent tissue anchoring leg, and may intersect with the first strut. In some embodiments, the first strut and the second strut may meet or intersect at the single junction angularly separating the at least one tissue anchoring leg and the adjacent tissue anchoring leg. For example, in FIG. 3C, first strut 2608a and second strut 2608a meet at single junction 2602.

In some embodiments, the at least one tissue anchoring leg may include at least one bent portion. For example, the at least one tissue anchoring leg may include two bent portions. For example, in FIG. 3D, ventricular tissue anchoring leg 2240 may include bent portions 3807 and 3808. In some embodiments, a bent portion may include a sharp curve or a more gradual angle. In some alternative embodiments, the at least one tissue anchoring leg may include at least two, at least three, at least four, or at least five bent portions. In some alternative embodiments, the at least one tissue anchoring leg may not include a bent portion. For example, the shape-memory characteristics of tissue anchoring legs 2240 enable them to maintain a fully contracted configuration when not bent, such as in FIG. 5A.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An expandable prosthetic valve for implantation within a native mitral valve, the prosthetic valve comprising:
   an expandable valve body having an atrial end, a ventricular end opposite the atrial end, and an intermediate portion extending between the atrial end and the ventricular end, the valve body being formed from a plurality of struts intersecting at junctions and including an annular outer frame and an inner frame situated at least partially within the annular outer frame; and
   a plurality of tissue anchoring legs extending from junctions within the intermediate portion of the valve body, wherein at least one of the tissue anchoring legs has a cross-sectional area ranging from 0.45 mm$^2$-0.65 mm$^2$ and a strut extending between the at least one tissue anchoring leg and an adjacent tissue anchoring leg has a cross-sectional area ranging from 0.15 mm$^2$-0.30 mm$^2$; and
   wherein a connector pin is situated at an intersection of the at least one tissue anchoring leg and two adjacent struts of the annular outer frame.

2. The prosthetic valve of claim 1,
   wherein the cross-sectional area of the at least one tissue anchoring leg is perpendicular to a direction of extension of the at least one tissue anchoring leg, and
   wherein the cross-sectional area of the strut extending between the at least one tissue anchoring leg and the adjacent tissue anchoring leg is perpendicular to a direction of extension of the strut.

3. The prosthetic valve of claim 1, wherein the cross-sectional area of the at least one tissue anchoring leg is four times larger than the cross-sectional area of the strut extending between the at least one tissue anchoring leg and the adjacent tissue anchoring leg.

4. The prosthetic valve of claim 1, wherein the at least one tissue anchoring leg is configured to extend radially outward from the valve body and in a non-ventricular direction, the at least one tissue anchoring leg being configured to engage ventricular tissue of the native mitral valve.

5. The prosthetic valve of claim 1, further comprising:
a plurality of atrial tissue anchoring arms extending radially outward from junctions within the intermediate portion of the valve body, wherein at least one atrial tissue anchoring arm is configured to extend from the valve body in an atrial direction.

6. The prosthetic valve of claim 5, wherein the at least one atrial tissue anchoring arm is configured to extend radially outward beyond a terminal end of the at least one tissue anchoring leg.

7. The prosthetic valve of claim 1, wherein a width of a radial outer surface of the at least one tissue anchoring leg is twice as large as a width of a radial outer surface of the strut extending between the at least one tissue anchoring leg and the adjacent tissue anchoring leg.

8. The prosthetic valve of claim 1, further comprising:
a tissue anchoring leg base strut extending between the junction from which the at least one tissue anchoring leg extends and a ventricular end of the valve body, wherein the tissue anchoring leg base strut has a cross-sectional area which is substantially equal to the cross-sectional area of the at least one tissue anchoring leg.

9. The prosthetic valve of claim 1, wherein the cross-sectional area of the at least one tissue anchoring leg is situated within a half of the at least one tissue anchoring leg which is radially closest to a center of the prosthetic valve.

10. The prosthetic valve of claim 9, wherein the half of the at least one tissue anchoring leg which is radially closest to the center of the prosthetic valve has a substantially constant cross-sectional area.

11. The prosthetic valve of claim 1, further comprising:
a second strut extending between the at least one tissue anchoring leg and the adjacent tissue anchoring leg, wherein a junction between the strut and the second strut is situated in an axial direction relative to the junction from which the at least one tissue anchoring leg extends.

12. The prosthetic valve of claim 1, wherein a terminal end of the at least one tissue anchoring leg is configured to be situated in an axial direction relative to the atrial end of the valve body.

13. The prosthetic valve of claim 1, wherein the at least one tissue anchoring leg and the adjacent tissue anchoring leg do not connect to the valve body at a common point of connection.

14. The prosthetic valve of claim 1, wherein the at least one tissue anchoring leg extends from a single junction of the valve body.

15. The prosthetic valve of claim 1, wherein an entire length of the at least one tissue anchoring leg is configured to extend radially outward and toward an atrium upon implantation.

16. An expandable prosthetic valve for implantation within a native mitral valve, the prosthetic valve comprising:
an expandable annular outer frame including a plurality of struts intersecting at junctions to form closed cells, the annular outer frame further including a plurality of ventricular tissue anchoring legs configured to extend radially outward from the junctions of the annular outer frame; and
an inner frame situated at least partially within the annular outer frame, the inner frame including a plurality of struts intersecting at junctions to form closed cells and a plurality of atrial tissue anchoring arms configured to extend radially outward from the junctions of the inner frame,
wherein at least one of the ventricular tissue anchoring legs has a cross-sectional area ranging from 0.45 mm$^2$-0.65 mm$^2$ and a strut extending between the at least one ventricular tissue anchoring leg and an adjacent ventricular tissue anchoring leg has a cross-sectional area ranging from 0.15 mm$^2$-0.30 mm$^2$; and
wherein a connector pin is situated at an intersection of the at least one ventricular tissue anchoring leg and two adjacent struts of the expandable annular outer frame.

17. The prosthetic valve of claim 16, wherein at least one of the atrial tissue anchoring arms has a cross-sectional area which is larger by 20% than a cross-sectional area of a strut extending between the at least one atrial tissue anchoring arm and an adjacent atrial tissue anchoring arm.

18. The prosthetic valve of claim 16, wherein at least one of the atrial tissue anchoring arms has a cross-sectional area which is larger by 20% than the cross-sectional area of the strut extending between the at least one ventricular tissue anchoring leg and the adjacent ventricular tissue anchoring leg.

19. The prosthetic valve of claim 16, wherein at least one connection between the annular outer frame and the inner frame is positioned away from respective atrial ends of the annular outer frame and inner frame.

20. The prosthetic valve of claim 16, wherein at least one connection between the annular outer frame and the inner frame is positioned in a ventricular direction relative to at least one atrial tissue anchoring arm and to the at least one ventricular tissue anchoring leg.

21. An expandable prosthetic valve for implantation within a native mitral valve, the prosthetic valve comprising:
an expandable valve body formed from a plurality of struts intersecting at junctions and including an annular outer frame and an inner frame situated at least partially within the annular outer frame; and
a plurality of tissue anchoring legs extending from the junctions of the valve body,
wherein at least one of the tissue anchoring legs has a cross-sectional area ranging from 0.45 mm$^2$-0.65 mm$^2$ and a first strut extending from the at least one tissue anchoring leg toward an adjacent tissue anchoring leg has a cross-sectional area ranging from 0.15 mm$^2$-0.30 mm$^2$,
wherein the at least one tissue anchoring leg and the adjacent tissue anchoring leg are angularly separated by a single junction; and
wherein a connector pin is situated at an intersection of the at least one tissue anchoring leg and two adjacent struts of the annular outer frame.

22. The prosthetic valve of claim 21, wherein the at least one tissue anchoring leg includes an opening therein.

23. The prosthetic valve of claim 21, further comprising:
a second strut extending from the adjacent tissue anchoring leg, wherein the first strut and second strut meet at the single junction.

24. The prosthetic valve of claim 21, wherein the at least one tissue anchoring leg includes at least one bent portion.

25. The prosthetic valve of claim 1, wherein the at least one tissue anchoring leg has a cross-sectional area of 0.53 mm$^2$.

26. The prosthetic valve of claim 1, wherein the strut extending between the at least one tissue anchoring leg and the adjacent tissue anchoring leg has a cross-sectional area of 0.165 mm$^2$.

27. The prosthetic valve of claim 1, wherein the strut extending between the at least one tissue anchoring leg and the adjacent tissue anchoring leg has a cross-sectional area of 0.2 mm$^2$.

* * * * *